(12) United States Patent
Roberts et al.

(10) Patent No.: US 7,470,426 B1
(45) Date of Patent: Dec. 30, 2008

(54) TREATMENT OF NEOPLASMS WITH VIRUSES

(75) Inventors: Michael S. Roberts, Walkersville, MD (US); Robert M. Lorence, Bethesda, MD (US); William S. Groene, New Market, MD (US); Harvey Rabin, Rockville, MD (US); Reid W. von Borstel, Potomac, MD (US)

(73) Assignee: Wellstat Biologics Corporation, Gaithersburg, MD (US)

( * ) Notice: Subject to any disclaimer, the term of this patent is extended or adjusted under 35 U.S.C. 154(b) by 0 days.

(21) Appl. No.: 09/958,809

(22) PCT Filed: Apr. 17, 2000

(86) PCT No.: PCT/US00/10204

§ 371 (c)(1),
(2), (4) Date: Apr. 19, 2002

(87) PCT Pub. No.: WO00/62735

PCT Pub. Date: Oct. 26, 2000

Related U.S. Application Data

(63) Continuation-in-part of application No. 09/292,376, filed on Apr. 15, 1999, now abandoned, which is a continuation-in-part of application No. 09/168,883, filed on Oct. 9, 1998, now abandoned, which is a continuation-in-part of application No. 08/948,244, filed on Oct. 9, 1997, now abandoned.

(51) Int. Cl.
A61K 48/00 (2006.01)
C12N 7/01 (2006.01)

(52) U.S. Cl. .................. 424/93.2; 435/235.1; 435/456

(58) Field of Classification Search ................ 530/828; 436/64; 435/7.2, 5, 7.1, 7.23, 235.1, 236, 435/237–239; 424/211.1, 214.1, 204.1, 184.1
See application file for complete search history.

(56) References Cited

U.S. PATENT DOCUMENTS

| | | | |
|---|---|---|---|
| 5,124,148 A | 6/1992 | Csatary et al. | |
| 5,198,336 A * | 3/1993 | Knobeloch et al. ............. | 435/4 |
| 5,215,745 A | 6/1993 | Csatary et al. | |
| 5,273,745 A | 12/1993 | Schirrmacher | |
| 5,274,137 A * | 12/1993 | Nicolaou et al. ............. | 549/510 |
| 5,585,096 A | 12/1996 | Martuza et al. | |
| 5,602,023 A | 2/1997 | Csatary | |
| 5,633,274 A * | 5/1997 | Halperin et al. ............. | 514/405 |
| 5,677,178 A | 10/1997 | McCormick | |
| 5,688,773 A | 11/1997 | Chiocca et al. | |
| 5,698,443 A * | 12/1997 | Henderson et al. ........ | 435/320.1 |
| 6,110,461 A | 8/2000 | Lee et al. | |

FOREIGN PATENT DOCUMENTS

| | | |
|---|---|---|
| DE | 39 22 444 C2 | 10/1991 |
| EP | 0 292 293 A2 | 11/1988 |
| EP | 0 292 293 A3 | 11/1988 |
| EP | 0 514 603 A | 11/1992 |
| EP | 0 564 121 A2 | 10/1993 |
| EP | 0 583 142 A2 | 2/1994 |
| EP | 1 314 431 A | 5/2003 |
| GB | 1069144 | 5/1967 |
| JP | A 58-116422 | 7/1983 |
| WO | WO 86/00529 | 1/1986 |
| WO | WO 86/00811 | 2/1986 |
| WO | WO 89/07445 | 8/1989 |
| WO | WO 93/18790 | 9/1993 |
| WO | WO 94/16716 | 8/1994 |
| WO | 94/19022 | 9/1994 |
| WO | WO 94/18992 | 9/1994 |
| WO | WO 94/25627 | 11/1994 |
| WO | WO 95/32706 | 12/1995 |
| WO | WO 96/00007 | 1/1996 |
| WO | WO 96/03997 | 2/1996 |
| WO | 96/26285 | 8/1996 |
| WO | 96/34625 | 11/1996 |
| WO | WO 97/01358 | 1/1997 |
| WO | WO 97/04805 | 2/1997 |
| WO | WO 97/26904 | 7/1997 |
| WO | WO 99/04026 | 1/1999 |
| WO | WO 99/08692 | 2/1999 |
| WO | 99/18799 | 4/1999 |
| WO | WO 99/18799 | 4/1999 |

(Continued)

OTHER PUBLICATIONS

Lorence et al. Complete regression of human neuroblastoma xenografts in athymic mice after local Newcastle disease virus therapy. J Natl Cancer Inst 86 (16): 1228-33, 1994.*
National Cancer Institute. Newcastle Disease virus (PDQ®): Complementary and Alternative Medicine, 47 pages.*
Kirn et al. Replicating viruses as selective cancer therapeutics, Molecular Medicine Today, 1996, vol. 2, 519-527.*
Eck et al. Gene-Based Therapy. Goodman & Gilman's The Pharmacological Basis of Therapeutics, 9th Edition, chapter 5.
Verma et al. Gene Therapy—Promises, Problems, and Prospects. Nature, vol. 389, pp. 239-242.

(Continued)

*Primary Examiner*—Emily M. Le
(74) *Attorney, Agent, or Firm*—Nixon & Vanderhye

(57) ABSTRACT

The subject invention relates to viruses that are able to replicate and thereby kill neoplastic cells with a deficiency in the IFN-mediated antiviral response, and their use in treating neoplastic disease including cancer and large tumors. RNA and DNA viruses are useful in this regard. The invention also relates to methods for the selection, design, purification and use of such viruses for cancer therapy.

58 Claims, 6 Drawing Sheets

FOREIGN PATENT DOCUMENTS

| WO | WO 99/29343 | 6/1999 |
| --- | --- | --- |
| WO | 99/45783 | 9/1999 |
| WO | WO 99/55345 | 11/1999 |
| WO | WO 99/64068 A | 12/1999 |
| WO | WO 00/45853 | 8/2000 |
| WO | WO 00/54795 A | 9/2000 |
| WO | 00/62735 | 10/2000 |

OTHER PUBLICATIONS

Lorence, R.M., et al, *Cancer Research*, 54: 6017-6021, Dec. 1, 1994 "Complete Regression of Human Fibrosarcomaj Xenografts after Local Newcastle Disease Virus Therapy".

Database Caplus, on STN Columbus (OH):chemical abstract service, DN 116: 104333, CN 1054192 A. Zheng, B., "Attenuated new castle disease virus for induction of interferons to combat neoplasm or viral diseases," Abstract, Apr. 9, 1991.

Gresser, et al, "Exogenous Interferon and Inducers of Interferon in the Treatment of Balb/c Mice Inoculated with RC19 Tumor Cells," *Nature*, Aug. 23, 1969, vol. 223, pp. 844-845.

Csatary, L.K., et al, Orvosi Hetilap 131: 2585-2588, 1990, "Virus Vaccines For The Tratment of Cancer".

Kirchner, H.H., et al, World J Urol. (1995) 13:171-173, "Adjuvant treatment of locally advanced renal cancer with autologous virus-modified tumor vaccines".

Murphy, Frederick A., et al, Virology, Second Edition, 1990, Chapter 2, pp. 9-35, "Virus Taxonomy".

Csatary, Laszlo K., The Lancet, Oct. 9, 1971, p. 825, "Viruses in the Treatment of Cancer".

Ahlert, T., et al, Cancer Res. 50 (1990), pp. 5962-5968, "Isolation of a Human Melanoma Adapted Newcastle Disease Virus Mutant with Highly Selective Replication Patterns".

Hashiro, G., et al, *Archives of Virology* 54, 307-315 (1977) "The Preferential Cytotoxicity of Reovirus for Certain Transformed Cell Lines".

Blaese, R.M., et al, European Journal of Cancer, vol. 30A, No. 8, pp. 1190-1193, 1994, "In situ Delivery of Suicide Genes for Cancer Treatment".

Zhang, Jian Feng, et al, Cancer Gene Therapy, vol. 3, No. 1, 1996, pp. 31-38, "Gene therapy with an adeno-associated virus carrying an interferon gene results in tumor growth suppression and regression".

Peplinski, Gary R., et al, Annals of Surgical Oncology, 3(2):15-23, "Prevention of Murine Breast Cancer by Vaccination with Tumor Cells Modified by Cytoline-Producing Recombinant Vaccinia Viruses".

Cotran, Ramzi S., M.D., et al, Robbins Pathologic Basis of Disease, 4th Edition, p. 251, "Kinetics of Tumor Cell Growth".

Schloer, G.M., et al, Journal of Virology, vol. 2, No. 1, Jan. 1968, pp. 40-47, "Relationship of Plaque Size and Virulence for Chickens of 14 Representative Newcastle Disease Virus Strains".

Tait, David L., et al, Clinical Cancer Research, vol. 3, pp. 1959-1968, Nov. 1997, "A Phase I Trial of Retroviral BRCA1sv Gene Therapy in Ovarian Cancer".

Martuza, Robert L., et al, Science, vol. 252, pp. 854-855, May 10, 1991, "Experimental Therapy of Human Glioma by Means of a Genetically Engineered Virus Mutant".

Hanson, R.P., et al, Science, vol. 122, pp. 156-157, Jul. 22, 1955, "Identification of Vaccine Strains of Newcastle Disease Virus".

Chambers, Renee, et al, Proc. Natl. Acad. Sci. USA, vol. 92, pp. 1411-1415, Feb. 1995, "Comparison of genetically engineered herpes simplex viruses for the treatment of brain tumors in a scid mouse model of human malignant glioma".

Asada, Teruo, MD, Cancer, vol. 34, pp. 1907-1928, Dec. 1974, "Treatment of Human Cancer with Mumps Virus".

Sreevalsan, Thazepadath, Biologic Therapy of Cancer: Principles and Practice, pp. 347-364, Chapter 14 Biologic Therapy with Interferon-∀ and ∃: Preclinical Studies.

Stoner, Gary D., et al, Nature, vol. 245, Oct. 12, 1973, pp. 319-320, "Effect of Neuraminidase pretreatment on the Susceptibility of Normal and Transformed Mammalian Cells to Bovine Enterovirus 261".

Joklik, W.K., Virology, Second Edition 1990, pp. 383-410, "Interferons".

Schnell, Matthias, J., et al, Cell, vol. 90, pp. 849-857, Sep. 5, 1997, "Construction of a Novel Virus that Targets HIV-1-Infected Cells and Controls HIV-1 Infection".

Lorence, Robert M., et al, Journal of the National Cancer Institute, vol. 86, No. 16, Aug. 17, 1994, pp. 1228-1233, Complete Regression of Human Neuroblastoma Xenografts in Athymic Mice After Local Newcastle Disease Virus Therapy.

Beattie, Elizabeth, et al, Virus Genes, 12:1, 89-94, 1996, "Host-Range Restriction of Vaccinia Virus E3L-Specific Deletion Mutants".

Howard, Brad, et al, Annals New York Academy of Sciences, Duke University Medical Center, p. 167-187, "Retrovirus-Mediated Gene Transfer of the Human (-IFN Gene: A Therapy for Cancer".

Suskind, R.G., et al, US Dept. of Health, Education, & Welfare, N.I.H., National Institute of Allergy and Infectious Diseases, and National Cancer Inst., Bethesda, Md. Oncolytic Effect of Coxsackie Virus, pp. 309-318, "Viral Agents Oncolytic for Human Tumors in Heterologous Host. Oncolytic Effect of Coxsackie B. Viruses." (22932), Oct. 29, 1956.

Bluming, Avrum Z., et al, The Lancet, Jul. 10, 1971, p. 105-106 "Regression of Burkitt's Lymphoma . . . Association With measles Infection".

Pasquinucci, G., The Lancet, Jan. 16, 1971, i, 136 "Possible Effect of Measles on Leukaemia".

Gross, Samuel, The Lancet, Feb. 20, 1971, p. 397-398, "Measles and Leukaemia".

Shingu, M., Journal of General Virology (1991), 72, 2031-2034, "Therapeutic effects of bovine enterovirus infection on rabbits with experimentally induced adult T cell leukaemia".

Faaberg, Kay S., et al, Journal of Virology, vol. 62, No. 2, p. 586-593, Feb. 1988, "Strain Variation and Nuclear Association of Newcstle Disease Virus Matrix Protein".

Holzaepfel, John H., et al, Cancer, May-Jun. 1957, vol. 10, pp. 577-580, "The Use of APC3 Virus As A Cancericidal Agent".

Smith, Robert R., MD, et al, Cancer, Nov.-Dec. 1956, vol. 9, pp. 1211-1218, "Studies on the Use of Viruses in the Treatment of Carcinoma of the Cervix".

Rukavishnikova, G.E., et al, Acta Virol., 20:387-394, 1976, "Some Immunological Mechanisms of the Influenza Virus Antitumour Effect".

Kalvakolanu, D.V.R., et al, Proc. Natl. Acad. Sci. USA, vol. 90, pp. 3167-3171, Apr. 1993, "Differentiation-dependent activation of interferon-stimulated gene factors and transcription factor NF-kB in mouse embryonal carcinoma cells".

Foy, Teresa M., et al, J. Exp. Med. © The Rockefeller University Press—0022-1007/93/11/1567/09, vol. 178, Nov. 1993, pp. 1567-1575, "In Vivo CD40-gp39 Interactions are Essential for Thymus-dependent Humoral Immunity. II. Prolonged Suppression of the Humoral Immune jResponse by an Antibody to the Ligand for CD40, gp39".

Field, H.J., et al, J. Hyg., Camb., 81, 267-277, (1978) "The pathogenicity of thymidine kinase-deficient mutants of herpes simplex virus in mice".

Spriggs, Dale R., et al, Nature, vol. 297, May 6, 1982, pp. 68-70, "Attenuated reovirus type 3 strains generated by selection of haemagglutinin antigenic variants".

Goldstein, Dvid J., et al, Virology, 166, 41-51 (1988), Factor(s) present in Herpes Simplex Virus Type 1-Infected Cells Can Compensate for the Loss of the Large Subunit of thej Viral Ribonucleotide Reductase: Characterization of an ICP6 Deletion Mutant.

Perkus, Marion E., et al, Virology, 180, 406-410 (1991), "Deletion of 55 Open Reading Frames from the Termini of Vaccinia Virus".

Meignier, Bernard, et al, Journal of Infectious Diseasesb, 162:313-321 (1990), In Vivo Behavior of Genetically Engineered Herpes Simplex Viruses R7017 and R7020. II. Studies in Immunocompetent and Immunosuppressed Owl Monkeys (*Aotus trivirgatus*).

Hughes, Stephen J., et al, Journal of Biological Chemistry, vol. 266, No. 30, Issue of Oct. 25, 1991, pp. 20103-20109, Vaccinia Virus Encodes an Active Thymidylate Kinase That Complements a *cdc8* Mutant of *Saccharomyces cerevisiae*.

Kerr, Shona M., et al, The EMBO Journal, vol. 10, No. 13, pp. 4343-4350, (1991), Vaccinia DNA ligase complements *Saccharomyces cerevisiae* cdc9, localizes in cytoplasmic factories and affects virulence and virus sensitivity to DNA damaging agents.

Clark, H. Fred, et al, Journal of Infectious Diseases, vol. 158, No. 3, Sep. 1988, p. 570-587, "Protective Effect of WC3 Vaccine Against Rotavirus Diarrhea in Infants During a predominantly Serotype 1 Rotavirus Season".

Takafuji, Ernest T., et al, Journal of Infectious Diseases, vol. 140, No. 1, Jul. 1979, pp. 48-53, "Simultaneous Administration of Live, Enteric-Coated Adenovirus Types 4, 7, and 21 Vaccines: Safety and Immunogenicity".

Taylor, M.W., et al, Journal of the National Cancer Institute, vol. 44, No. 3, Mar. 1970, pp. 515-519, "Virus-Induced Regression of Tumor Growth".

Bohle, MD, Wolfran, et al, *Cancer*, vol. 66, No. 7, pp. 1517-1523, Oct. 1, 1990 "Postoperative Active Specific Immunization in Colorectal Cancer Patients With Virus-Modified Autologous Tumor-Cell Vaccine".

Eaton, Monroe D., et al, *Infection and Immunity*, vol. 15, No. 1, Jan. 1977, pp. 322-328, "Autoimmunity Induced by Injection of Virus-Modified Cell Membrane Antigens in Syngeneic Mice".

Wheelock, M.D., E. Frederick, et al, *The New England Journal of Medicine*, vol. 271, No. 13, Sep. 24, 1964, pp. 645-651, "Observations on the Repeated Administration of Viruses to a Patient with Acute Leukemia".

*The Lancet*, Oct. 9, 1971, p. 825, "Viruses in the Treatment of Cancer".

Kenney, Shannon, et al, *JNCL Editorial Issue 16*, Jun. 20, 1997, pp. 1-3, Jun. 20, 1997, "Viruses as Oncolytic Agents: a New Age for 'Therapeutic' Viruses?"

Rodriguez, Ron, et al, *Cancer Research*, 57, 2559-2563, Jul. 1, 1997, "Prostate Attenuated Replication Competent Adenovirus (ARCA) CN706: A Selective3 Cytotoxic for Prostate-specific Antigen-positive Prostate Cancer Cells".

Martuza, MD, Robert, *Examiner*, Oct. 1995, Georgetown University Medical Center, pp. 1-8, "Novel Treatment Approach for Malignant Brain Tumors Developed at Georgetown".

Mineta, Toshihiro, et al, *Nature Medicine*, vol. 1, No. 9, Sep. 1995, 938-943, "Attenuated Multi-Mutated Herpes Simplex Virus-1 for the Treatment of Malignant Gliomas".

Zhenxiang, Huang, et al, *Acta Academiae Medicine Sinicae*, vol. 6, No. 3, Jun. 1984, "Studies on Viral Immunotherapy of Ascitic Tumors in Mice.—I. Results of Treatment on Viruses of Ehrlich and S180 Ascitic Tumor Cells" p. 213-216.

*Abstract*, 1362, Ganly, et al, *Proceedings of ASCO*, vol. 16 (1997), p. 433a "Phase I Trial of Intratumoral Injection with an E1B-Attenuated Adenovirus, ONYX-015, in Patients with Recurrent p53(–) Head and Neck Cancer".

Abstract, 2400, Kirn, et al, *Proceedings for the American Association for Cancer Research*, vol. 37, Mar. 1996, p. 352 "ONYX-015 Selectively Replicates in and Lyses Cells Lacking Functional Small p53."

Schirrmacher, V., et al, *Institut for Immunologic und Genetik am Deutschen Krebsforschungszentrum*, 6900 Heidelberg, Germany, pp. 19-49, Mar. 13, 1986, "Successful application of non-oncogenic viruses for antimetastatic cancer immunotherapy".

Lorence, Robert M., et al, *Journal of the National Cancer Institute*, vol. 80, No. 16, Oct. 19, 1988, pp. 1305-1312, "Newcastle Disease Virus as an Antineoplastic Agent: Induction of Tumor Necrosis Factor-α and Augmentation of Its Cytotoxicity".

Reichard, Kirk W., et al, *Journal of Surgical Research*, 52, 448-453 (1992), "Newcastle Disease Virus Selectively Kills Human Tumor Cells".

Eaton, Monroe D., et al, *Journal of the National Cancer Institute*, vol. 39, No. 6, Dec. 1967, pp. 1089-1097, "Contribution of Antiviral Immunity to Oncolysis by Newcastle Disease Virus in a Murine Lymphoma".

Beverley, P.C., et al, *Int. J. Cancer*, 11, 212-223 (1973), "Immune Responses In Mice To tumour Challenge After Immunization With NewCastle Disease Virus-Infected or X-Irradiated Tumour Cells or Cell Fractions".

Shoham, Jacob, et al, *Nat. Immun. Cell Growth Regul.*, 1990; 9:165-172, "Augmentation of Tumor Cell Immunogenicity by Viruses—An Approach to Specific Immunotherapy of Cancer".

Bart, Robert S., et al, *Nature New Biology*, vol. 245, No. 147, Oct. 24, 1973, pp. 229-230, "Role of Interferon in the Anti-Melanoma Effects of Poly(I).Poly (C) and Newcastle Disease Virus".

Sinkovics, Joseph, et al, *Intervirology*, 1993, 36:193-214, "New Developments in the Virus Therapy of Cancer: A Historical Review".

Murray, Douglas R., et al, *Cancer*, Aug. 1977, vol. 40, No. 2, pp. 680-686, "Viral Oncolysate in the Management of Malignant Melanoma".

Cassel, William A., *Cancer*, 52:856-860, Sep. 1, 1983, "A Phase II Study on the Postsurgical Management of Stag Malignant Melanoma With a Newcastle Disease Virus Oncolysate".

Cassel, William A., *Med. Oncol. & Tumor Pharmacother.*, vol. 9, No. 4, pp. 169-171, 1992, "A Ten-Year Follow-up on Stage II Magignant Melanoma Patients Treated Postsurgically with New Castle Disease Virus Oncolysate".

Haines, G.K., et al, *Virchows Archiv B Cell Pathol*, (1993) 63:289-295, "Correlation of the expression of double-stranded RNA-dependent protein kinase (p68) with differentiation in head and neck squamous cell carcinoma".

James, C. David, et al, *Cancer Research*, 51, pp. 1684-1688, Mar. 15, 1991, "Chromosome 9 Deletion Mapping Reveals Interferon α and Interferon β-1 Gene Deletions in Human Glial Tumors".

Arroyo, Pedro J., et al, *Cancer Immunol Immunother*, (1990) 31:305-311, "Active specific immunotherapy with vaccinia colon oncolysate enhances the immunomodulatory and antitumor effects of interleukin-2 and interferon ∀ in a murine hepatic metastasis model".

Zhang, Wei-Wei, et al, *Cancer Gene Therapy*, vol. 1, No. 1, 1994: pp. 5-13 "High-efficiency gene transfer and high-level expression of wild-type p53 in human lung cancer cells mediated by recombinant adenovirus".

Korth, Marcus, J., et al, *Gene*, 170 (1996) 181-188, "Cloning, expression, and cellular localization of the oncogenic 58-kDa inhibitor of the RNA-activated human and mouse protein kinase".

Barber, Glen N., et al, *Proc. Natl. Acad. Sci. USA*, vol. 91, pp. 4278-4282, May 1994 Biochemistry, "The 58-kilodalton inhibitor of the interferon-induced double-stranded RNA-activated protein kinase is a tetratricopeptide repeat protein with oncogenic properties".

Mathews, Michael B., et al, *Journal of Virology*, vol. 65, No. 11, Nov. 1991, p. 5657-5662, "Adenovirus Virus-Associated RNA and Translation Control".

Imani, Farhad, et al, *Proc. Natl. Acad. Sci. USA*, vol. 85, pp. 7887-7891, Nov. 1988 Biochemistry, "Inhibitory activity for the interferon-induced protein kinase is associated with the reovirus serotype . . . protein".

Tanaka, Nobuyuki, et al, *Journal of Immunotherapy*, vol. 16, No. 4 (1994) pp. 283-293, "Immunotherapy of a Vaccinia Colon Oncolysate Prepared with Interleukin-2 Gene-Encoded Vaccinia Virus and Interferon-∀ Increases the Survival of Mice Bearing Syngeneic Colon Adenocarcinoma".

Csatary M.D., Laszlo K., et al, *Cancer Detection and Prevention*, 17(6):619-627 (1993), "Attenuated Veterinary Virus Vaccine for the Treatment of Cancer".

Cassel Ph.D, William A., et al, *Cancer*, vol. 18, No. 7, pp. 863-868, Jul. 1965, "Newcastle Disease Virus As An Antineoplastic".

Linge, Claire, et al, *Cancer Research 55*, pp. 4099-4104, Sep. 15, 1995, "Interferon System Defects in Human Malignant Melanoma".

Machida, Haruhiko, et al, *Microbiol. Immunol.*, vol. 23 (7), 643-650, 1979, "Effect of Nucleosides on Interferon Production and Development of Antiviral State Induced by Poly I ● Poly C".

Tanaka, Nobuyuki, et al, *Cell*, vol. 77, 829-839, Jun. 17, 1994, Cellular Commitment to Oncogene-Induced Transformation or Apoptosis Is Dependent on the Transcription Factor IRF-1.

*Science*, vol. 274, Oct. 18, 1996, pp. 342-343, "Will a Twist of Viral Fate Lead to a New Cancer Cure?"

Bischoff, James R., et al, *Science*, vol. 274, Oct. 18, 1996, pp. 373-376, "An Adenovirus Mutant That Replicates Selectively in p53-Deficient Human Tumor Cells".

Andreansky, Samita S., et al, *Proc. Natl. Acad. Sci. USA*, vol. 93, pp. 11313-11318, Oct. 1996 Colloquium Paper, "The application of genetically engineered herpes simplex viruses to the treatment of experimental brain tumors".

Gastl, Guenther, et al, *Cancer Research 52*, pp. 6229-6236, Nov. 15, 1992, "Retroviral Vector-mediated Lymphokine Gene Transfer into Human Renal . . . Cells".

Buller, R. Mark L., et al, *Virology 164*, 182-192 (1988), "Cell Proliferative Response to Vaccinia Virus Is Mediated by VGF".

Child, Stephanie J., et al, *Virology*, 174, 625-629 (1990), "Insertional Inactivation of the large Subunit of Ribonucleotide Reductase Encoded by Vaccinia Virus Is Associated with Reduced Virulence In Vivo".

Restifo, Nicholas P., et al, *The Journal of Experimental Medicine*, vol. 175, Jun. 1992, pp. 1423-1431, "A Nonimmunogenic Sarcoma Transduced with the cDNA for Interferon ( Elicits CD8+ T Cells against the Wild-type Tumor . . . Presentation Capability".

Buller, R.M.L., et al, *Nature*, vol. 317, Oct. 31, 1985, pp. 813-815, "Decreased virulence of recombinant vaccinia virus expression vectors is associated with a thymidine kinase-negative phenotype".

Kirn, D.H., et al, *Molecular Medicine Today*, Dec. 1996, p. 519-527, "Replicating Viruses as Selective Cancer Therapeutics".

Heise, C., et al, *Nature Medicine*. vol. 3, No. 6, Jun. 1997, p. 639-645 "Onyx-015, an E1B gene-attenuated adenovirus, causes tumor-specific cytolysis and antitumoral efficacy that can be augmente4d by standard chemotherapeutic agents".

Zhang, Jian-Feng, et al, *Proc. Natl. Acad. Sci*, vol. 93, pp. 4513-4518, Apr. 1996, "Treatment of a human breast cancer xenograft with an adenovirus vector containing an interferon gene results in rapid regression due to viral oncolysis and gene therapy".

Katze, Michael G., *Trends in Microbiology*, vol. 3, No. 2, Feb. 1995, pp. 75-78, "Regulation of the interferon-induced PKR:can viruses cope?"

Maheshwari, Rada K., et al, *Biochemical and Biophysical Research Communications*, vol. 117, No. 1, 1983, Nov. 30, 1983, pp. 161-168, "Low Infectivity of Vesicular Stomatitis Virus (VSV) Particles Released from Interferon-Treated Cells is Related to Glycoprotein Deficiency".

Chou, Joany, et al, *Proc. Natl. Acad. Sci. USA*, vol. 92, pp. 10516-10520, Nov. 1995, "Association of a Mr 90,000 phosphoprotein with protein kinase PKR in cells exhibiting enhanced phosphorylation of translation . . . herpes simplex virus 1".

Xu, Bo, et al, *Blood*, vol. 84, No. 6, Sep. 15, 1994, pp. 1942-1949, "Primary Leukemia Cells Resistant to α-Interferon In Vitro are Defective in the Activation of the DNA-Binding Factor . . . Factor 3".

Petricoin III, Emanuel, et al, *Molecular and Cellular Biology*, vol. 14, No. 2, Feb. 1994, pp. 1477-1486 "Human Cancer Cell Lines Express a Negative Transcriptional Regulator of the Interferon Regulatory Factor Family of DNA Binding Proteins".

Symons, Julian A., et al, *Cell*, vol. 81, pp. 551-560, May 19, 1995, "Vaccinia Virus Encodes a Soluble type 1 Interferon Receptor of Novel Structure and Broad Species Specificity".

Sinkovics et al, "New Developments in the Virus Therapy of Cancer: A Historical Review," Intervirology, vol. 36, pp. 193-214 (1993).

XP-002164069, Horvath et al, "Comparison of oncolytic Newcastle Disease Virus strains," Cancer Institute, St. Joseph's Hospital, Tampa, Florida).

Yu et al, "Antiviral action of interferon-β on . . . ," Med Microbial Immunol, vol. 184, pp. 45-52 (1995).

Nickels et al, "Identification of an amino acid change that affects . . . ," Journal of General Virology, vol. 75, pp. 3591-3595 (1995).

Schubert et al, "Primary Structure of the Vesicular . . . ," Journal of Virology, Aug. 1984, pp. 505-514.

Balachandran et al,"Activation of the dsRNA-dependent protein . . . ," The EMBO Journal, vol. 17, No. 23, pp. 6888-6902 (1998).

Durbin et al, "Targeted Disruption of the Mouse *Stat1* Gene Results . . . ," Cell, vol. 84, pp. 443-450 (1996).

Stojdl et al, "Exploiting tumor-specific defects in the interferon pathway . . . ," Nature Medicine, vol. 6, No. 7, pp. 821-825 (2000).

Balachandran et al. "Vesicular Stomatitis Virus . . . ," Life, vol. 50, pp. 135-138 (2000).

Francoeur et al, "The Isolation of Interferon-Inducing Mutants of . . . ," Virology, vol. 160, pp. 236-245 (1987).
Database Caplus, on STN Columbus (OH): chemical abstract service, DN 116: 104333, CN 1054192 A, Zhang, B. "Attenuated new castle disease virus for induction of interferons to combat neoplasm or viral diaeases." Abstract, Apr. 9, 1991.
Rosenbergova et al, "Purification of Newcastle Disease . . . ," Acta virol, vol. 25, pp. 31-35 (1981).
Maeda et al, "Isolation and Characterization of Defective Interfering . . . ," Microbiol. Immunol., vol. 22, No. 12, pp. 775-784 (1978).
Strube et al, "Sensitivity of ortho- and paramyxovirus replication to human interferon α," Molec. Biol. Rep., vol. 10, pp. 237-243 (1985).
Zhang, B.; "Attenuated newcastle disease virus for induction of interferons to combat neoplasm or viral diseases"; (1992); Chemical Abstracts 116:104333.
Leonard, J.P. et al; "Effects of Single-Dose Interleukin-12 Exposure on Interleukin-12-Associated Toxicity and Interferon-γ Production"; *Blood*; vol. 90, No. 7, Oct. 1, 1997, pp. 2541-2548.
Stiehm, E.R., et al; "Interferon: Immunolobiology and Clinical Significance"; *Annals of Internal Medicine*; 96, pp. 80-93 (1982).
Proceedings of the American Association for Cancer Research Annual, vol. 36, p. 439 (1995).
Okuno, Y. et al; "Studies on the use of mumps virus for treatment of human cancer"; Biken J., 1978, vol. 21, No. 2, pp. 37-49.
Ikeda, H., et al; "Detection of Heterozygous Mutation in the Retinoblastoma Gene in a Human Pituitary Adenoma Using PCR-SSCP Analysis and Direct Sequencing"; Endocr Pathol. 1995, vol. 66, pp. 189-196.
Zhang Bingtuan; "Process for Preparing Inducing Interferon of Human Body"; Sep. 1991; Abstract; (D4).
Gresser et al; "Inhibitory Effect of Interferon on Murine Sarcoma and Leukaemia Virus Infection in Vitro"; Nature, Nature, vol. 223, pp. 844-845; Aug. 1969.
Pecora, et al, J. Clin. Oncol. (2002) 20(9): 2251-2266.
G.S. Reddy et al; "Use of BHK Cell Culture-Adapted Newcastle Disease Virus for Immunization of Chicks"; 1992; XP-002237247 (Abstract).
G.S. Reddy et al; "Comparison of Two Experimental Binary Ethylenimine Bei Inactivated Newcastle Disease Oil-Emulsion Vaccines"; 1991; XP-002237248 (Abstract).
J. Gelg Jr. et al; "Pathogenicity and Cross-Protection of Pigeon Paramyxovirus 1 and Newcastle Disease Virus in Young Chickens"; (1987); XP-002237249 (Abstract).
M.A. Shuaib et al; "Studies on the Development of Pelleted Newcastle Disease Virus Vaccine"; (1985); XP-002237250 (Abstract).
M.A. Al Imadi et al; "The Susceptibility of Domestic Waterfowl to Newcastle Disease Virus and Their Role in its Spread"; (1982); XP-002237251 (Abstract).
B. Rivetz et al; "Enzymatic Changes in Serum and Tissues in Fowl Infected with a Neurotropic Mesogenic Strain of Newcastle Disease Virus"; (1982); XP-002237252 (Abstract).
B. Lomniczi; "Properties of Nonneurovirulent Plaque Forming Mutants of Newcastle Disease Virus"; (1976); XP-002237253 (Abstract).
D.Y. Perey et al; "Host Resistance Mechanisms to Newcastle Disease Virus in Immunodeficient Chickens" (38540); (1975); XP-002237254 (Abstract).
I. Szeri, et al; "Effect of Microbial Immunomodulants on the Course of LCMV Infection in Old Mice with Thymus Involution"; (1992); XP-002237255 (Abstract).
P.B. Spradbrow et al; "Oral Newcastle Disease Vaccination with V4 Virus in Chickens"; Aust. Vet. J., (1991) vol. 68, No. 3, pp. 114-115; XP-002237256; (Abstract).
E.I. Ugochukwu; "Caecal Coccidiosis in Chicks Following Intramuscular Vaccination Against Newcastle Disease"; Bull. Anim. Health Prod. Afr., (1982) vol. 30, No. 4, pp. 353-357; XP-002237257; (Abstract).
W. Leuthgen; "Detection of Antibodies in the Tracheal Exudate of Chicken After Infection with Newcastle Virus"; Immunologie (1972), 144(3), 273-80; XP-002237258 (Abstract).
Hanson et al; "Identification of Vaccine Strains of Newcastle Disease Virus"; Science, vol. 156, 1955, pp. 156-157; XP002237246.

Official Action dated Apr. 16, 2004 in co-pending U.S. Appl. No. 08/260,536, filed Jun. 16, 1994.

Pecora, A.L.; "Phase I Trial of Intravenous Administration of PV701, an Oncolytic Virus, in Patients with Advanced Solid Cancers"; *Journal of Clinical Oncology*; vol. 20, No. 9; pp. 2251-2266 (2002).

Hotte, S.J.; "Slow Intravenous Infusion of PV701, an Oncolytic Virus: Final Results of a Phase I Study"; *Supplement to Journal of Clinical Oncology*; vol. 22, No. 14S (Jul. 15, 2004); 2004 ASCO Annual Meeting Proceedings (Post-Meeting Edition).

Freeman, A.I., et al; "Phase I/II Trial of Intravenous OV001 Oncolytic Virus in Resistant Glioblastoma Multiforme (GBM)"; *Journal of Clinical Oncology*; vol. 22, No. 14S; p. 1515 (Jul. 15, 2004); 2004 ASCO Annual Meeting Proceedings (Post-Meeting Edition).

Nakamura, T. & Russell, S.J.; "Oncolytic Measles Virus for Cancer Therapy"; *Expert Opinion Biol. Ther.*; vol. 4, No. 10; pp. 1685-1692 (2004).

Kinoh, H., et al; "Generation of a Recombinant Sendai Virus that is Selectively Activated and Lyses Human Tumor Cells Expressing Matrix Metalloproteinases"; *Gene Therapy*; vol. 11; pp. 1137-1145 (2004).

Muster, T., et al; "Interferon Resistance Promotes Oncolysis by Influenza Virus NS1-Deletion Mutants"; *Int. J. Cancer*; vol. 110; pp. 15-21 (2004).

Poster (ASCO Meeting); "Slow Intravenous Infusion of PV701, An Oncolytic Virus: Final Results of a Phase I Study"; *2004 Am. Soc. Clin. Oncology (ASCO) Mtg*.

Shafren, D.R., et al; "Systemic Therapy of Malignant Human Melanoma Tumors by a Common Cold-Producing Enterovirus, Coxsackievirus A21"; *Clinical Cancer Research*; vol. 10; pp. 53-60 (2004).

Gromeier, M., et al; "Intergeneric Poliovirus Recombinants for the Treatment of Malignant Glioma"; *Poliovirus: Proc. Natl Acad Sci USA*; vol. 97; pp. 6803-6808 (2000).

Yang, W.Q., et al; "Reovirus as an Experimental Therapeutic for Brain and Leptomeningeal Metastases from Breast Cancer"; *Gene Therapy*; vol. 11; pp. 1579-1589 (2004).

Thorne, S.H., et al; "Future Directions for the Field of Oncolytic Virotherapy: a Perspective on the use of Vaccinia Virus"; *Expert Opin. Biol. Ther.*; vol. 4, No. 8; pp. 1307-1321 (2004).

Catalogue of Animal Viruses and Antisera, Chlamydiae and Rickettsiae; *American Type Culture Collection*; C. Buck & G. Paulino, eds.; Sixth Edition p. 81 (1990).

Malaczewska, J., et al; "Effect of KLP-602 on Virus Replication in Cell Cultures"; *Polish Journal of Veterinary Sciences*; vol. 7, No. 2; pp. 103-108 (2004).

Ballagi-Pordany, A., et al; "Identification and Grouping of Newcastle Disease Virus Strains by Restriction Site Analysis of a Region from the F Gene"; *Arch Virol.*; vol. 141; pp. 243-261 (1996).

Al-Garib, S.O., et al; "Detection of Antibody-Forming Cells Directed Against Newcastle Disease Virus and their Immunoglobulin Class by Double Immunoenzyme Histochemistry"; *Avian Diseases*; vol. 47; pp. 453-457 (2003).

Powell, J.A., et al "Antibodies to Newcastle Disease Virus in Various Human Diseases"; *In Archs. Allergy appl. Immun.*; vol. 76; pp. 331-335 (1985).

Huang, H.J., et al; "Nonspecific Innate Immunity Against *Escherichia coli* Infection in Chickens Induced by Vaccine Strains of Newcastle Disease Virus"; *Avian Diseases*; vol. 44; pp. 790-796 (2000).

Scanlon, D.B., et al; "Pathotyping Isolates of Newcastle Disease Virus Using Antipeptide Antibodies to Pathotype-specific Regions of their Fusion and Hemagglutinin-Neuraminides Proteins"; *Arch. Virol*; vol. 144; pp. 55-72 (1999).
Wise, M.G., et al; "Development of a Real-Time Reverse-Transcription PCR for Detection of Newcastle Disease Virus RNA in Clinical Samples"; *Journal of Clinical Microbiology*; vol. 42, No. 1; pp. 329-338 (2004).
Marino, O.C., et al; "Cellular and Humoral Response of In Ovo-Bursectomized Chickens to Experimental Challenge with Velogenic Newcastle Disease Virus"; *Avian Diseases*; vol. 31, No. 2; pp. 293-301 (1986).
So, Al-Garib; et al; "Detection of Antibody-forming cells directed against Newcastle disease virus and their immunoglobulin class by double immunoenzyme histochemistry"; *PubMed; Avin Dis.*; Apr.-Jun. 2003; 47(2):453-7; (Abstract).
Huang, H.J., et al; "Nonspecific Innate Immunity Against *Escherichia coli* Infection in Chickens Induced by vaccine Strains of Newcastle Disease Virus"; *PubMed; Avian Dis.*; Oct.-Dec. 2000; 44(4):790-6 (Abstract).
Scanlon, D.B., et al; "Pathotyping isolates of Newcastle disease virus using antipeptide antibodies to pathotype-specific regions of their fusion and hemagglutinin-neuraminidase proteins"; *PubMed; Arch. Virol.*; (1999); 144(1):55-72 (Abstract).
Gelb, J., Jr., et al; "Detergent-treated Newcastle disease virus as an agar gel precipitin test antigen"; *PubMed; Poult Sci.*; (1987) 66(5):845-53 (Abstract).
Powell, J. A., et al; "Antibodies to Newcastle disease virus in various human diseases"; *PubMed; Int Arch Allergy Appl Immunol.*; (1985) 76(4):331-5 (Abstract).
Gelb, J., Jr., et al; "Detergent-Treated Newcastle Disease Virus as an Agar Gel Precipitin Test Antigen"; *Delaware Agricultural Experiment Station, Dept. of Animal Science and Agricultural Biochemistry, College of Agricul. Sciences, Univ. of Delaware*, Newark, Delaware; (1986) pp. 845-853.
Seal, B.S., et al; "Phylogenic Relationships among Highly Virulent Newcastle Disease Virus Isolates Obtained form Exotic Birds and Poultry from 1989 to 1996"; *J. of Clinical Microbiology*; vol. 36, No. 4; pp. 1141-1145 (1998).
Berinstein, A., et al; "Use of a Heteroduplex Mobility Assay to Detect Differences in the Fusion Protein Cleavage Site Coding Sequence among Newcastle Disease Virus Isolates"; *J. of Clinical Microbiology*; vol. 32, No. 9; pp. 3171-3178 (2001).
Mendel, D.B., et al; "Oral Administration of a Prodrug of the Influenza Virus Neuraminidase Inhibitor GS 4071 Protects Mice and Ferrets against Influenza Infection"; *Antimicrobial Agents and Chemotherapy*; vol. 42, No. 3; pp. 640-646 (1998).
Lorence, R., et al; "Complete Regression of Human Neurobalstoma Xenografts in Athymic Mice after Local NDV Therapy"; *J. Natl Cancer Inst.*; vol. 86, No. 16 (1994) pp. 1228-1233 (XP-002934125).
Elkin, E.B., et al; "The effect of changes in tumor size on breast carcinoma survival in the U.S.", 1975-1999;*Cancer*; 2006; 106(8): 1863; author reply 1864; PubMed. (1 pg).
Kiesslich, R., et al; "Colonoscopy, Tumors, and Inflammatory Bowel Disease—New Diagnostic Methods"; *Endoscopy 2006*; vol. 38, pp. 5-10.
Wisnivesky, J.P., et al; "The Effect of Tumor size on Curability of Stage 1 Non-Small Cell Lung Cancers"; *Medscape Perspectives on the 2nd Annual Multidisciplinary Prostate Cancer Symposium*; Feb. 24-26, 2006, San Francisco, CA; (2 pgs).
CBS News; Healthwatch; "Cancer Survival Tied to Tumor Size"; Aug. 22, 2006; (2 pgs).
Lorence, R.M., et al; "Systemic Therapy of Human Tumor Xenografts Using PV701, an Oncolytic Strain of Newcastle Disease Virus, in Combination with a Cytotoxic Drug Demonstrates At Least Additive Antitumor Responses"; #5428; *Pro-Virus, Inc.*, Gaithersburg, MD; (4 pgs).
PPMK107 is a Clonal Virus; (1 pg).
Felzmann, T., et al; "Characterization of the antitumor immune response generated by treatment of murine tumors with recombinant adenoviruses expressing HSVtk, IL-2, IL-6 or B7-1."; *Clinical Gene Therapy Branch, NHGRI, NIH*, Bethesda, MD; 1997; 4(12): 1322-9; PubMed (1 pg).
Topf, N., et al; "Regional 'pro-drug' gene therapy: intravenous administration of an adenoviral vector expressing the *E. coli* cytosine deaminase gene and systemic administration of 5-fluorocystosine suppresses growth of hepatic metastasis of colon carcinoma"; *Gene Therapy*; 1998 5(4):507-13; PubMed (1 pg).
Knezic, Z., et al; "Constitutive interferon expression from retroviral vector"; *Antiviral Res.*; 1993; 22(2-3):215-21; PubMed. (1 pg).
Garcia-Sanchez, F., et al; "Cytosine Deaminase Adenoviral Vector and 5-Fluorocytosine Selectivity Reduce Breast Cancer Cells 1 Million-Fold When They Contaminate Hematopoietic Cells: A Potential Purging Method for Autologous Transplantation"; *Blood*; vol. 92, No. 2 (Jul. 15, 1998); pp. 672-682.

Bradshaw Jr., H.D., et al; "Human Thymidine Kinase Gene: Molecular Cloning and Nucleotide Sequence of a cDNA Expressible in Mammalian Cells"; *Molecular and Cellular Biology*; vol. 4, No. 11; Nov. 1984, pp. 2316-2320.

Goeddel, D.V., et al; "Synthesis of human fibroblast interferon by *E. coli*"; *Nucleic Acid Research*; vol. 8, No. 18; (1980); pp. 4057-4074.

Fiola, C., et al; "Tumor selective replication of Newcastle Disease Virus: Association with defects of tumor cells in antiviral defence"; *Int. J. Cancer*; vol. 119; pp. 3289-3338 (2006).

Moriuchi, S., et al; "Double suicide gene therapy using a replication defective herpes simplex virus vector reveals reciprocal interference in a malignant glioma model"; *Gene Therapy*; vol. 9; pp. 584-591 (2002).

Sinkovics, J., et al; D1, "New Developments in the Virus therapy of Cancer: A Historical Review"; *Intervirology*; vol. 36; pp. 193-214 (1993).

D2, *Journal of Preventive Veterinary Medicine*; 3 (general No. 94); pp. 21-24 (1997); (English Language Translation).

Chou, J., et al; "Association of a $M_r$ 90,000 phosphoprotein with protein kinase PKR in cells exhibiting enhanced phosphorylation of translation initiation factor eIF-2α and premature shutoff of protein synthesis after infection with $_{\gamma 1}34.5^-$ mutants of herpes simplex virus 1"; *Proc.Natl. Acad. Sci*; vol. 92; pp. 10516-10520 (1995).

Kubo, T.; Patent Application No. S49-147261; Public Patent Disclosure Bulletin No. JP S51-73117 dated Jun. 24, 1976; Title of Invention "A method for preparing a cancer therapy agent" (6 pgs).

Jia Fenglan et al; ACTA Academiae Medicinae Sinicae; vol. 7, No. 5; Oct. 1985 (4 pgs).

Reichard, K.W., et al; The Association for Academic Surgery; Twenty-Fifth Annual Meeting, Nov. 20-23, 1991, University of Colorado Health Sciences Center, Denver, Colorado (p. 152).

Huang et al ; ACTA Academiae Medicinae Sinicae, vol. 6, No. 3 (1984) (5 pgs).

Schirrmacher, V., et al; "Successful application of non-oncogenic viruses for antimetastatic cancer immunotherapy"; Accepted for publication Mar. 13, 1986 (pp. 19-49).

Partial European Search Report; Application No./Patent No. 07016086.6-2107 dated Apr. 21, 2008.

Spradbrow, P.B., et al; "Oral Newcastle disease vaccination with V4 virus in chickens: Comparison with other routes"; *LifeSci* (1991) XP-002237256 (Abstract).

Nema, S., et al; "Excipients and Their Use in Injectable Products"; *PDA Journal of Pharmaceutical Science and Technology*; vol. 51, No. 4 (1997) pp. 166-171, XP-009041329.

Schloer, G.M., et al; "Relationship of Plaque Size and Virulence for Chickens of 14 Representative Newcastle Disease Virus Strains"; *Journal of Virology*; vol. 2, No. 1 (1968) pp. 40-47, XP-002475731.

Sinkovics, J., et al; "New Developments in the Virus Therapy of Cancer: A Historical Review"; *Intervirology*, vol. 36, No. 4, (1993) pp. 193-214, XP-000982845.

Mer, David C., et al; "Immunological Studies of the Functions of Paramyxovirus Glycoproteins"; *Virology*, vol. 109, No. 1 (1981), pp. 94-105, XP-000647392.

Notice of Opposition to European Patent Application No./Patent No. 98949797.9-2107/1032269 dated Jun. 9, 2008 issued in corresponding Hong Kong Patent Application No. 00107775.6.

Reichard, Kirk W., et al; "Newcastle Disease Virus Selectively Kills Human Tumor Cells"; *Journal of Surgical Research*, vol. 32, No. 5 (1992), pp. 448-453, Appendix A (D3 dated May 29, 2008).

Daniel, M.D., et al; "Isolation and Characterization of Three Plaque-Type Clones of the Hickman Strain of Newcastle Disease Virus"; pp. 434-440, (1968) (D4 dated May 29, 2008).

Csatary, L.K., et al; "Annenuated Veterinary Virus Vaccine for the Treatment of Cancer"; *Cancer Detection and Prevention*; vol. 17, No. 6; pp. 619-627 (1993) (D5 dated May 29, 2008).

Copending U.S. Appl. No. 10/700,143; Publication No. US2004/0131595, Jul. 8, 2004; Pending Claims 157-161, 163-170, 172, 174, 183, 196-219 and 230-232.

\* cited by examiner

Antiviral Effect of IFN in Various Cell Lines

TREATMENT OF NEOPLASMS WITH VIRUSES

This application is a 371 of PCT/US00/10204, filed Apr. 17, 2000, which is a continuation-in-part of Ser. No. 09/292, 376, filed Apr. 15, 1999, now abandoned which is a continuation-in-part of Ser. No. 09/168,883 filed Oct. 9, 1998, now abandoned which is a continuation-in-part of Ser. No. 08/948, 244, filed Oct. 9, 1997, now abandoned.

FIELD OF THE INVENTION

The subject invention relates to viruses that are able to replicate in and cause the death of neoplastic cells with a deficiency in the interferon (IFN)-mediated antiviral response. RNA and DNA viruses are useful in this regard. The invention also relates to the use of these viruses for the treatment of neoplastic diseases including cancer and large tumors.

BACKGROUND OF THE INVENTION

Neoplastic disease which includes cancer is one of the leading causes of death among human beings. There are over 1.3 million new cases of cancer diagnosed in the United States each year and 550,000 deaths. Detecting cancer early, before it has spread to secondary sites in the body, greatly increases a host's chances of survival. However, early detection of cancer is not always possible, and even when it is, treatments are unsatisfactory, especially in cases of highly malignant cancers. Cancer treatments, including chemotherapy and radiation, are much less effective in later stages, especially when neoplastic growths are large and/or constitute a high tumor burden. (See Hillard Stanley, Cancer Treat. Reports, Vol. 61, No. 1, Jan/Feb 1977, p. 29-36, Tannock, Cancer Research, 42, 4921-4926, Dec. 1982).

Tumor regression associated with exposure to various viruses has been reported. Most of the viruses described are pathogenic in humans, and include mumps and measles. The effect of other specific viruses on particular types of cancer cells has also been described. Smith et al, (1956) *Cancer*, 9, 1211 (effect of adenovirus on cervix carcinoma); Holzaepfel et al, (1957) *Cancer*, 10, 557 (effect of adenovirus on epithelial tumor); Taylor et al, (1970) *J. Natl. Cancer Inst.*, 44, 515 (effect of bovine enterovirus-1 on sarcoma-1); Shingu et al, (1991) *J. General Virology*, 72, 2031 (effect of bovine enterovirus MZ-468 on F-647, a leukemia cells); Suskind et al, (1957) *PSEBM*, 94, 309 (effect of coxsackie B3 virus on HeLa tumor cells); Rukavishnikova et al, (1976) *Acta Virol.*, 20, 387 (effect of influenza A strain on ascites tumor).

The earliest references described partial tumor regression in patients treated with live attenuated viral vaccine with the aim to vaccinate them against smallpox or rabies. See DePace, N. G. (1912) *Ginecologia*, 9, 82-88; Salmon, P. & Baix (1922) *Compt. Rend. Soc. Biol.*, 86, 819-820. Partial regression of tumors and regression of leukemias have also been noted during naturally occurring measles infections. See Pasquinucci, G. (1971) *Lancet*, 1, 136; Gross, S. (1971) *Lancet*, 1, 397-398; Bluming, A. Z. and Ziegler, J. L. (1971) *Lancet*, 2, 105-106. In one study of 90 cancer patients intentionally infected with live mumps virus, partial tumor regression was noted in 79 cases. See Asada (1994) *Cancer*, 34, 1907-1928. While the side effects of these viruses were temporary, serious sequela of infection with these human pathogens is of major concern.

Viruses are categorized as follows [see Murphy A. and Kingsbury D W, 1990, In: *Virology*, 2$^{nd}$ Edition (Ed. Fields, B. N.), Raven Press, New York, pp 9-35]:

| Dividing Characteristics | Virus Family Names |
|---|---|
| RNA viruses | |
| ss[a] RNA, positive-sense, nonsegmented, nonenveloped, | Picornaviridae, Calciviridae |
| ssRNA, positive-sense, nonsegmented, enveloped, | Togaviridae, Flaviviridae, Coronaviridae |
| ssRNA, negative-sense, nonsegmented, enveloped, | Rhabdoviridae, Filoviridae, Paramyxoviridae |
| ssRNA, negative-sense, segmented, enveloped | Orthomyxoviridae |
| ssRNA, ambisense, segmented, enveloped | Bunyaviridae, Arenaviridae |
| ds[b] RNA, positive-sense segmented, nonenveloped | Reoviridae, Birnaviridae |
| ssRNA, DNA step in replication, positive-sense, nonsegmented, enveloped | Retroviridae |
| DNA viruses | |
| ss/dsDNA, nonenveloped | Hepadnaviridae |
| ssDNA, nonenveloped | Parvoviridae |
| dsDNA, nonenveloped | Papovaviridae, Adenoviridae |
| dsDNA, enveloped | Herpesviridae, Poxviridae, Iridoviridae |

[a]ss = single stranded
[b]ds = double-stranded

Included among the family Herpesviridae (or Herpesviruses), are the subfamilies Alphaherpesvirus (including Genus Varicellarviurs and Genus Simpexvirus), Betaherpesvirus, and Gammaherpesvirus.

Newcastle disease virus ("NDV") is a member of the Paramyxoviridae (or Paramyxoviruses). The natural hosts for NDV are chickens and other birds. NDV typically binds to certain molecules on the surface of animal host cells, fuses with the cell surface, and injects its genetic material into the host. NDV is a cytocidal virus. Once inside the cell, the viral genes direct the host cell to make copies of the virus leading to death of the host cell, releasing the copies of NDV which infect other cells. Unlike some viruses, NDV is not known to cause any serious human disease. Unlike other kinds of viruses (e.g., HTLV-1, Hepatitis B). Paramyxoviruses are not known to be carcinogenic. Temporary regression of tumors has been reported in a small number of patients exposed to NDV, See, Csatary, L. K. (1971) *Lancet*, 2, 825. Csatary noted the regression of a gastrointestinal cancer in a chicken farmer during an epidemic of Newcastle disease in his chickens. In a similar anecdotal report, Cassel, W. A. and Garrett, R. E. (1965) *Cancer*, 18, 863-868, noted regression of primary cervical cancer, which had spread to the lymph nodes, in a patient following injection of NDV into the cervical tumor. Since the mechanism of tumoricidal activity was thought to be immunologic, no work was carried out to address direct tumor cytotoxicity of the virus. Instead, efforts focused upon the immuno-modulating effects of NDV. See, for example, Murray, D. R., Cassel, W. A., Torbin, A. H., Olkowski, Z. L., & Moore, M. E. (1977) *Cancer*, 40, 680; Cassel, W. A., Murray, D. R., & Phillips, H. S. (1983) *Cancer*, 52, 856; Bohle, W., Schlag, P. J., Liebrich, W., Hohenberger, P., Manasterski, M., Miller, P., and Schirrmacher, V. (1990) *Cancer*, 66, 1517-1523.

The selection of a specific virus for tumor regression was based on serendipity or trail and error in the above citations.

Only recently, have rational, mechanism-based applications for virus use in cancer treatment been developed using DNA viruses. Examples of this type of approach are found in the development of recombinant adenoviral vectors that replicate only in tumors of specific tissue origin (Rodriguez, R. et al, 1997 *Cancer Res.*, 57:2559-2563), or those that lack certain key regulatory proteins (Bischoff, J R, et al, 1996 *Science*, 274:373-376). Another recent approach has been the use of a replication-incompetent recombinant adenoviral vector to restore a critical protein function lost in some tumor cells (Zhang, W W, et al, 1994 *Cancer gene therapy*, 1:5-13). Finally, herpes simplex virus has also been engineered to replicate preferentially in the rapidly dividing cells that characterize tumors (Mineta, T., et al, 1994 *Cancer Res.*, 54:3963-3966).

U.S. application Ser. No. 08/260,536, hereby incorporated by reference in its entirety, discloses the use of NDV or other Paramyxovirus in the treatment of cancer.

Viral IFN transgene expression

One common approach to the treatment of cancer with viral therapeutics has been the use of virus vectors for the delivery of certain genes to the tumor mass.

Recombinant adenovirus, adeno-associated virus, vaccinia virus and retroviruses have all been modified to express an interferon gene alone or in combination with other cytokine genes.

In Zhang et al. ((1996) *Proc. Natl. Acad. Sci.*, USA 93:4513-4518), a recombinant adenovirus expressing a human interferon consensus (i.e., synthetic) gene was used to treat human breast cancer (and other) xenografts in nude mice. The authors concluded ". . . a combination of viral oncolysis with a virus of low pathogenicity, itself resistant to the effects of IFN and IFN gene therapy, might be a fruitful approach to the treatment of a variety of different tumors, in particular breast cancer." In contrast to subject invention which relates to interferon-sensitive viruses, Zhang et al. (1996) teach the use of an interferon-resistant adenovirus in the treatment of tumors.

In Zhang et. al. ((1996) *Cancer Gene Ther.*, 3:31-38), adeno-associated virus (AAV) expressing consensus IFN was used to transduced human tumor cells in vitro followed by injection into nude mice. The transduced tumors either did not form tumors or grew slower than the non-transduced controls. Also, injection of one transduced human tumor cell into the tumor mass of another, non-transduced tumor resulted in a small decrease in size. In Peplinski et al. ((1996) *Ann. Surg. Oncol.*, 3:15-23), IFN gamma (and other cytokines, expressed either alone, or in combination) were tested in a mouse breast cancer model. Mice were immunized with tumor cells virally modified with recombinant vaccinia virus. When re-challenged with tumor cells, the mice immunized with virally modified cells has statistical improvement in the disease-free survival time.

Gastl, et al. ((1992) *Cancer Res.*, 52:6229-6236), used IFN gamma-expressing retroviral vectors to transduce renal carcinoma cells in vitro. These cells were shown to produce higher amounts of a number of proteins important for the function of the immune system.

Restifo et al. ((1992) *J. Exp. Med.*, 175:1423-1431), used IFN gamma-expressing retroviral vector to transduce a murine sarcoma cell line allowing the tumor cell line to more efficiently present viral antigens to CD8+ T cells. Howard, et al. ((1994) *Ann. NY Acad. Sci.*, 716:167-187), used IFN gamma-expressing retroviral vector to transduce murine and human melanoma tumor cells. These cells were observed to increase the expression of proteins important to immune function. These cells were also less tumorigenic in mice as compared to the non-transduced parent line, and resulted in activation of a tumor-specific CTL response in vivo.

Use of Therapeutic Doses of Interferon as an Adjuvant to Viral Cancer Therapy

Because of the known immune-enhancing properties of IFN, several studies have examined the use of IFN protein in combination with other viral cancer vaccine therapies.

In Kirchner et al. ((1995) *World J. Urol.*, 13:171-173), 208 patients were immunized with autologous, NDV-modified, and lethally irradiated renal-cell carcinoma tumor cells, and were co-treated with low dose IL-2 or IFN alpha. The authors stated that this treatment regime results in an improvement over the natural course in patients with locally-advanced renal-cell carcinoma. The dose was approximately $3.3 \times 10^3$ to $2.2 \times 10^5$ PFU/kg. This was a local therapy, as opposed to a systemic approach, with the goal of inducing an anti-tumor immune response.

Tanaka et al. ((1994) *J. Immunother. Emphasis Tumor Immunol.*, 16:283-293), co-administered IFN alpha with a recombinant vaccinia virus as a cancer vaccine therapy model in mice. This study showed a statistical improvement in survivability in mice receiving IFN as compared to those that did not. The authors attributed efficacy of IFN to the induction of CD8-positive T cells in those animals.

Arroyo et al. ((1990) *Cancer Immunol. Immunother.*, 31:305-311) used a mouse model of colon cancer to test the effect of IFN alpha and/or IL-2 co-therapy on the efficacy of a vaccinia virus colon oncolysate (VCO) cancer treatment. They found that the triple treatment of VCO+IL-2+IFN was most efficacious in this murine model. This approach relies on immunization as the mechanism of anti-tumor activity.

IFN was used in these studies to augment the ability of the cancer cells to be recognized by the immune system.

OBJECTS OF THE INVENTION

It is an object of the invention to provide viruses for the treatment of diseases including cancer.

It is a further object of the invention to provide viruses for the treatment of neoplastic diseases including cancer.

It is a further object of the invention to provide a means by which candidate viruses are selected and/or screened for use in the therapy of neoplastic diseases.

It is a further object of the invention to provide guidance in the genetic engineering of viruses in order to enhance their therapeutic utility in the treatment of neoplastic diseases.

It is a further object of this invention to provide a means with which to screen potential target cells for viral therapy with a goal of assessing the sensitivity of the candidate target cells to viral killing.

It is a still further object of this invention to provide guidance in the management of viral therapy.

It is an object of the invention to provide a method for treating large tumors.

It is a further object of the invention to provide purified virus and methods for obtaining same.

SUMMARY OF THE INVENTION

This invention relates to a method of infecting a neoplasm in a mammal with a virus comprising administering an interferon-sensitive, replication-competent clonal virus, selected from the group consisting of RNA viruses and the DNA virus families of Adenovirus, Parvovirus, Papovavirus, Iridovirus, and Herpesvirus, to the mammal.

This invention also relates to a method of infecting a neoplasm in a mammal with a virus comprising systemically administering an interferon-sensitive, replication-competent clonal virus to the mammal.

This invention also relates to a method of treating a neoplasm including cancer in a mammal comprising administering to the mammal a therapeutically effective amount of an interferon-sensitive, replication-competent, clonal virus selected from the group consisting of RNA viruses, and the DNA virus families of Adenovirus, Parvovirus, Papovavirus, Iridovirus, and Herpesvirus.

This invention also relates to a method of infecting a neoplasm in a mammal with a virus comprising administering an interferon-sensitive, replication-competent clonal vaccinia virus, having one or more mutations in one or more viral genes involved with blocking interferon's antiviral activity selected from the group of genes consisting of K3L, E3L and B18R, to the mammal.

The invention also relates to a method of treating a neoplasm including cancer in a mammal administering to the mammal a therapeutically effective amount of an interferon-sensitive, replication-competent vaccinia virus having one or more mutations in one or more viral genes involved with blocking interferon's antiviral activity selected from the group of genes consisting of K3L, E3 L and B18R.

The invention also relates to a method of infecting a neoplasm at least 1 cm in size with a virus in a mammal comprising administering a clonal virus, selected from the group consisting of (1) RNA viruses; (2) Hepadenavirus; (3) Parvovirus; (4) Papovavirus; (5) Herpesvirus; (6) Poxvirus; and (7) Iridovirus, to the mammal.

The invention also relates to a method of treating a neoplasm in a mammal, comprising administering to the mammal a therapeutically effective amount of a clonal virus, selected from the group consisting of (1) RNA viruses; (2) Hepadenavirus; (3) Parvovirus; (4) Papovavirus; (5) Herpesvirus; (6) Poxvirus; and (7) Iridovirus, wherein the neoplasm is at least 1 centimeter in size.

The invention also relates to a method of treating a tumor in a mammal, comprising administering to the mammal a therapeutically effective amount of an RNA virus cytocidal to the tumor, wherein the mammal has a tumor burden comprising at least 1.5% of the total body weight.

The invention also relates to a method of screening tumor cells or tissue freshly removed from the patient to determine the sensitivity of the cells or tissue to killing by a virus comprising subjecting the cells or tissue to a differential cytotoxicity assay using an interferon-sensitive virus.

The invention also relates to a method for identifying a virus with antineoplastic activity in a mammal comprising a) using the test virus to infect i) cells deficient in IFN-mediated antiviral activity, and ii) cells competent in IFN-mediated antiviral activity, and b) determining whether the test virus kills the cells deficient in IFN-mediated antiviral activity preferentially to the cells competent in interferon-mediated antiviral activity.

The invention also relates to a method of making viruses for use in antineoplastic therapy comprising: a) modifying an existing virus by diminishing or ablating a viral mechanism for the inactivation of the antiviral effects of IFN, and optionally b) creating an attenuating mutation that results in lower virulence than said existing virus.

The invention also relates to a method of controlling viral replication in a mammal treated with a virus selected from the group consisting of RNA viruses, Adenoviruses, Poxviruses, Iridoviruses, Parvoviruses, Hepadenaviruses, Varicellaviruses, Betaherpesvirues, and Gammaherpesvirues comprising administering an antiviral compound.

The invention also relates to a method of screening tumor cells, tumor tissue, or tissue sections to determine which tumor cells or tissue allow a virus to bind comprising subjecting the cells, tissues, or tissue sections to an immunoassay or immunostain for the amount of virus receptor present on the tumor cells or tumor tissue.

The invention also relates to a method of infecting a neoplasm in a mammal with a virus comprising systemically administering a desensitizing dose of an interferon-sensitive, replication-competent clonal virus to the mammal before administering at least one subsequent higher dose of a virus.

The invention also relates to a method of infecting a neoplasm in a mammal with a virus comprising administering an interferon-sensitive, replication-competent clonal virus to the mammal over a course of at least 4 minutes.

This invention also relates to a method of infecting a neoplasm in a mammal with a virus comprising administering a replication-competent clonal virus selected from the group consisting of the Newcastle disease virus strain MK107, Newcastle disease virus strain NJ Roakin, Sindbis virus, and Vesicular stomatitis virus.

Included in the invention are:
i) a clonal Paramyxovirus purified by ultracentrifugation without pelleting;
ii) a clonal Paramyxovirus purified to a level of at least $2\times10^9$ PFU per mg of protein;
iii) a clonal Paramyxovirus purified to a level of at least $1\times10^{10}$ PFU per mg of protein;
iv) a clonal Paramyxovirus purified to a level of at least $6\times10^{10}$ PFU per mg of protein;
v) a clonal RNA virus purified to a level of at least $2\times10^9$ PFU per mg of protein;
vi) a clonal RNA virus purified to a level of at least $1\times10^{10}$ PFU per mg of protein;
vii) a clonal RNA virus purified to a level of at least $6\times10^{10}$ PFU per mg of protein;
viii) a clonal cytocidal DNA virus which is interferon-sensitive and purified to a level of at least $2\times10^9$ PFU/mg protein;
ix) a replication-competent vaccinia virus having a) one or more mutations in one or more of the K3L, E3L and B18R genes, and b) an attenuating mutation in one or more of the genes encoding thymidine kinase, rubonucleotide reductase, vaccinia growth factor, thymidylate kinase, DNA ligase, dUTPase;
x) a replication-competent vaccinia virus having one or more mutations in two or more genes selected from the group consisting of K3L, E3L, and B18R;
xi) a Herpesvirus having a modification in the expression of the (2'-5')A analog causing the Herpesvirus to have increased interferon sensitivity; and
xii) a Reovirus having an attenuating mutation at omega 3 causing said virus to become interferon-sensitive.
xiii) a replication competent cytocidal virus which is interferon sensitive and purified to a level of at least $2\times10^9$ PFU/mg protein.
xiv) a reovirus purified to a level of at least $2\times10^9$ PFU/mg protein.

Also included in the invention are the following methods:
i) a method of purifying an RNA virus comprising the steps of a) generating a clonal virus; and b) purifying said clonal virus by ultracentrifugation without pelleting; or c) purifying said clonal virus by tangential flow filtration with or without subsequent gel permeation chromatography, and ii) a method of purifying a Paramyxovirus comprising purifying the virus by ultracentrifugation without pelleting, or by tangential flow filtration with or without subsequent gel permeation chromatography.

The invention also relates to a method of treating a disease in a mammal, in which the diseased cells have defects in an interferon-mediated antiviral response, comprising administering to the mammal a therapeutically effective amount of an interferon-sensitive, replication-competent, clonal virus.

The invention also relates to a method of infecting a neoplasm in a mammal with a virus comprising administering an interferon-responsive, replication-competent clonal RNA virus to the mammal.

The invention a method of treating a disease of viral etiology in a mammal comprising administering to the mammal a therapeutically effective amount of a replication-competent clonal virus.

The invention also relates to a method of infecting a neoplasm in a mammal comprising administering a virus selected from the group of families consisting of Paramyxoviridae, Orthomyxoviridae, Rhabdoviridae, Togaviridae, Flaviviridae, Picornaviridae, Coronaviridae, Reoviridae, Poxviridae, Herpesviridae, and Parvoviridae.

The invention also relates to a method of treating tumor ascites comprising administering an interferon-sensitive, replication-competent clonal virus.

The invention also relates to a method of reducing pain in a mammal comprising administering an interferon-sensitive, replication competent clonal virus.

The invention also relates to a method of treating a neoplasm in a mammal comprising subjecting a sample from said mammal to an immunoassay to detect the amount of virus receptor present, and if the receptor is present, administering an interferon-sensitive, replication competent clonal virus, which bind the receptor, to the mammal.

DETAILED DESCRIPTION OF THE INVENTION

Figure 1:
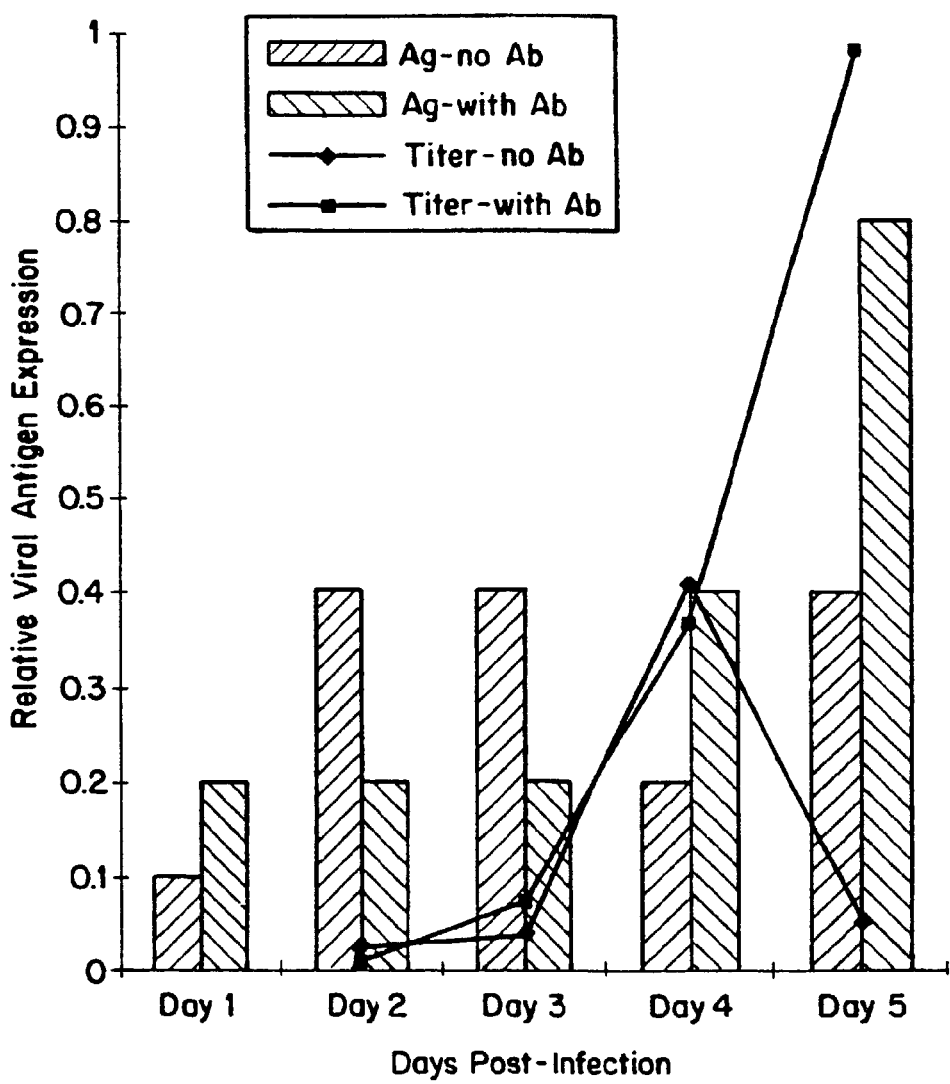
FIG. 1 shows the effect of anti-interferon-beta antibody on viral antigen expression and infectious titer in NHEK (normal human epithelial keratinocytes) cells.

The present invention relates to the discovery of a novel mechanism by which viral replication selectively kills neoplastic cells deficient in an interferon (IFN)-mediated anti-viral response. This invention also provides methods for selection, design, purification, and use of viruses for the treatment of neoplastic diseases including cancer and large tumors. The viruses of the invention selectively replicate in and kill neoplastic cells based on the selective deficiency in these cells of an IFN-mediated anti-viral response. Administration of the appropriate dosage of virus results in neoplastic cell death, whereas normal cells, which possess an intact IFN-mediated anti-viral response, limit the replication of the virus and are not killed. Included in the subject of the invention is the use of paramyxoviruses such as NDV, and other viruses, for use in the treatment of diseases including neoplastic disease such as cancer. The invention also teaches screening and engineering of other viruses suitable for use as therapeutics of neoplastic diseases. Another embodiment of the invention involves a method of identifying tumor tissues that are candidates for viral therapy. Finally, the invention also describes the preparation of highly purified virus.

Rationale for the use of interferon-sensitive viruses including NDV to treat neoplastic disease NDV demonstrates selective killing of tumor cells Newcastle disease virus causes selective cytotoxic effects against many human tumor cells with markedly less effects on most normal human cells. In a differential cytotoxicity assay, human cancer cells derived from renal carcinomas, pancreatic carcinoma, sarcomas, melanomas, breast carcinomas, ovarian carcinomas, bladder carcinomas, colon carcinoma, prostate carcinoma, small cell and non-small cell lung carcinomas, and glioblastomas were discovered to be approximately 3 to 4 orders of magnitude more sensitive to NDV than many normal human cells [renal epithelial cells, fibroblasts, keratinocytes, melanocytes, and endothelial cells (see Example 1)]. The differential cytotoxicity assay can also be applied to fresh isolates from the patient's cells or tumor tissue.

An in vitro assay is used to define the tumoricidal activity of NDV as described in Example 1. The assay measures the amount of virus required to kill 50% of the tested cell culture in a five day time period. Examples 2 and 3 show the results of in vivo experiments in which virus was administered to athymic mice bearing human tumor xenografts by either the intratumoral (Example 2) or intravenous (Example 3) route. These results demonstrate that NDV can cause regression of a variety of human tumor types in a standard animal model for the testing of potential chemotherapeutic agents.

Evidence that NDV is specifically replicating within the tumor was demonstrated by immunohistochemical staining for virus antigen (Example 2). Within 30 minutes of intratumoral virus injection, the tumor tissue was negative for viral antigen. However, by day 2 post treatment, intense immunostaining for viral antigen was seen within the tumor, indicating virus replication within the tumor. Importantly, virus replication was specific for the tumor tissue since the neighboring connective tissue and skin were negative for viral antigen.

Importantly, efficient replication of NDV is crucial for the ability of the virus to kill infected cells, as demonstrated in studies using UV-inactivated non-clonal virus (Lorence, R., et al, 1994, *J. Natl. Cancer Inst.*, 86:1228-1233).

NDV can also cause regression of large tumors after intratumoral and intravenous administration (Examples 4 through 9). Intratumoral NDV treatment of large intradermal A375 human melanoma xenografts ($\geq 10$ mm in maximal dimension; tumor volume of $\geq 300$ mm$^3$) in athymic mice lead to high rates of tumor regression (Examples 4 through 8). Intravenous NDV treatment of large subcutaneous HT1080 human fibrosarcoma xenografts ($\geq 10$ mm in maximal dimension) in athymic mice lead to complete or partial tumor regression in five out of six mice (Example 9).

The class I interferon family of cytokines are important negative modulators of viral infection The class I interferons consist of the IFNα, found primarily in cells of hematopoietic origin, and IFNβ found primarily in fibroblasts and epithelial cells. [Joklik, W. K. 1990. Interferons. pp 383-410, *Virology*, second edition, edited by B. N. Fields, D. M. Knipe et al, Raven Press Ld., New York; and Sreevalsan, T. 1995. Biological Therapy with Interferon-α and β: Preclinical Studies. pp 347-364. *Biologic Therapy of Cancer*, second edition, edited by V. T. DeVita, Jr., S. Hellman, and S. A. Rosenberg; J. B. Lippincott Company, Philadelphia.] Both types of IFN function through an apparently common mechanism of action that includes the degradation of double-stranded RNA intermediates of viral replication, and the inhibition of cellular translation through the activity of a protein kinase activated by double-stranded RNA (Joklik, W. K. 1990. Interferons. pp 383-410, *Virology*. Second Edition, edited by B. N. Fields, D. M. Knipe et al., Raven Press Ltd, New York, and references therein). Several viruses (influenza, EBV, SV40, adenovirus, vaccinia) have evolved mechanisms by which one or more pathways of the IFN system are inactivated, thus allowing the efficient replication of the virus (Katze, M. G. 1995. Trends in Microbiol. 3:75-78).

A wide variety of tumor cells are deficient in the ability to limit viral infection through an IFN-dependent mechanism Human cervical carcinoma cells (HeLa) were over three-hundred-fold less sensitive to the inhibition of vesicular stomatitis virus replication following pre-treatment with IFN than a non-transformed fibroblast control cell line (Maheshwari R. K., 1983. Biochem, Biophys. Res. Comm. 17:161-168). The subject inventors have discovered that infection of a co-culture of tumorigenic human head and neck carcinoma cells (KB) and normal human skin fibroblast cells (CCD922-sk) results in viral replication initially in both cell types, followed by a limiting of the infection in the normal cells versus continued replication and killing of the tumor cells (Example 10). Moreover, although IFN was being secreted by the normal cells into the culture medium, the tumor cells were unable to respond to the IFN at the concentrations being produced to establish an antiviral state. Further evidence for the role of IFN in the differential sensitivity of tumor cells versus normal cells to killing by NDV was obtained in two separate experiments in which normal fibroblast cells (CCD922-sk) or normal epithelial keratinocyte cells (NHEK) were shown to become more sensitive to infection with NDV in the presence of neutralizing antibody of IFN (Examples 11 and 12). Finally, parallel infection of normal fibroblasts (CCD922-sk) and human tumor cells (KB) in the presence of IFN revealed that the normal cells were at least 100-fold more sensitive to the antiviral effects of added IFN than were the tumor cells (Examples 13 and 14). Similar testing of variety tumor cell lines (total of 9) revealed a clear correlation in the relative sensitivity of a cell line to killing by NDV and an inability of the cell line to manifest an interferon-mediated antiviral response (Example 26).

Interferon and Cell Growth

There are several species of interferon (IFN) including natural and recombinant forms of α-IFN, β-IFN, ω-IFN, and γ-IFN as well as synthetic consensus forms (e.g., as described in Zhang et al. (1996) Cancer Gene Therapy, 3:31-38). In addition to the anti-viral activities that lead to its discovery, IFN is now known to play an important role in the normal regulation of cell growth and differentiation. IFN is viewed as a negative growth regulator and several key proteins involved in the function and regulation of IFN activity have been shown to act as tumor-suppresser proteins in normal cells (Tanaka et al, 1994 *Cell* 77:829-839). Moreover, several other proteins known to antagonize the anti-viral activity of IFN have been shown to have oncogenic potential when expressed inappropriately (see below, Barber, G N, 1994, *Proc. Natl. Acad. Sci. USA* 91:4278-4282). Cells derived from a number of human cancers have been shown to be deleted in the genes encoding IFN (James, C D, et al, 1991, *Cancer Res.*, 51:1684-1688), and partial or complete loss of IFN function has been observed in human cervical carcinoma (Petricoin, E, et al, 1994 *Mol. Cell. Bio.*, 14:1477-1486), chronic lymphocytic leukemia (Xu, B., et al, 1994, *Blood*, 84:1942-1949), and malignant melanoma cells, (Linge, C., et al, 1995, *Cancer Res.*, 55:4099-4104).

The IFN-inducible protein kinase (p68, PKR) has been shown to be an important regulator of cellular and viral protein synthesis. A correlation has emerged that links the expression or activity of the p68 kinase to the cellular state of differentiation. Thus, poorly differentiated cells, such as those occurring in many cancers, are deficient in p68 function (Haines, G. K., et al, 1993 *Virchows Arch B Cell Pathol.* 63:289-95). Cells that lack p68 activity are generally sensitive to viral mediated killing because the p68 kinase is an important effector of the IFN-inducible antiviral state. The antiviral activity of p68 can be antagonized through a direct interaction with a cellular protein identified as p58. When cloned and overexpressed in NIH3T3 cells, p58 causes the cells to exhibit a transformed phenotype and anchorage-independent growth (Barber G N et al., 1994 Proc Natl Acad Sci USA 91:4278-4282), and a number of human leukemia cell lines have been shown to overexpress the p58 protein (Korth M J, et al., 1996 Gene 170:181-188). The activity of p68 kinase can also be antagonized by the Ras protein. Cells that express mutant, activated forms of Ras have been shown to be defective in the activation of p68 kinase by double-stranded RNA (Mundshau, L. J., and Faller, D. V., 1992, J. Biol. Chem., 267:23092-23098). Sensitivity of viral killing in undifferentiated cells can be reversed through the induction of a more differentiated phenotype (Kalvakolanu, D V R and Sen, G. C. 1993 *Proc. Natl Acad Sci USA* 90:3167-3171).

DEFINITIONS

Cells competent in an interferon-mediated antiviral response. As used herein, the term "cells competent in an interferon-mediated antiviral response" are cells which respond to low levels (e.g., 10 units per ml) of exogenous interferon by significantly reducing (at least 10-fold, more advantageously at least 100-fold, more advantageously at least 1000-fold, and most advantageously at least 10,000-fold) the replication of an interferon-sensitive virus as compared to in the absence of interferon. The degree of virus replication is determined by measuring the amount of virus (e.g., infectious virus, viral antigen, viral nucleic acid). CCD922 normal fibroblasts are cells competent in an interferon-mediated antiviral response.

Cells deficient in an interferon-mediated antiviral response. As used herein, the term "cells deficient in an interferon-mediated antiviral response" are cells which fail to meet the criteria listed above for a cell competent in an interferon-meditated antiviral response, that is, they fail to respond to low levels (e.g., 10 units per ml) of exogenous interferon by significantly reducing the replication of an interferon-sensitive virus as compared to in the absence of interferon. KB oral carcinoma cells are cells deficient in an interferon-mediated antiviral response.

Clonal. Use of the term "clonal" virus is defined hereafter as virus derived from a single infectious virus particle and for which individual molecular clones have significant nucleic acid sequence homology. For example, the sequence homology is such that at least eight individual molecular clones from the population of virions have sequence homology greater than 95%, more advantageously greater than 97%, more advantageously greater than 99%, and most advantageously 100% over 300 contiguous nucleotides.

Cytocidal. As used herein, the term "cytocidal" virus refers to a virus that infects cells resulting in their death.

Desensitization. As used herein, the phrase desensitization refers to pretreatment with an agent that lessens the side effects caused by virus administration.

Desensitizing Dose. As used herein, the phrase "desensitizing dose" refers to the amount of virus required to lessen the side effects of subsequent doses of virus.

Differential Cytotoxicity Assay. As used herein, the phrase "differential cytotoxicity assay" for screening tumor cells or tissue using a virus refers to the (a) virus infection of the tumor cells and one or more control cells or tissue; (b) a determination of cell survivability or death for each sample (for example, by the use of a dye indicator of cell viability as in detailed in Example 1) after one or more days of infection; and (c) based on the results, an estimation of the sensitivity (for example, by IC50 determination as detailed in Example 1) of the sample to the virus compared to the control(s).

Infecting a Neoplasm. As used herein, the term "infecting a neoplasm" refers to the entry of viral nucleic acid into the neoplastic cells or tissues.

Interferon-sensitive. As used here, the phrase "interferon-sensitive" virus (e.g., NDV) means a virus that replicates significantly less (at least 10-fold less, advantageously at least 100-fold less, more advantageously at least 1000-fold less, and most advantageously at least 10,000-fold less), in the presence of interferon compared to in the absence of interferon. This is determined by measuring the amount of virus (e.g., infectious virus, viral antigen, viral nucleic acid) obtained from cells competent in an interferon-mediated antiviral response in the presence or absence of low levels of exogenous interferon (e.g., 10 units per ml).

Interferon-responsive. As used herein, the phrase "interferon-responsive" virus (e.g., NDV) refers to a virus that following an infection at an moi (multiplicity of infection) of 1.0 at least 50% less viral antigen is expressed in cells pretreated for 24 hours, and maintained with 500 Units/ml of the exogenous interferon-α, than in untreated cells. The measurements are made in cells competent in an interferon-mediated antiviral response at least 24 hours post-infection, and on the first day that would allow a determination of a 50% decrease in viral antigen expression.

Neoplasm and Neoplastic Disease. As used herein, "neoplasma" means new growth of tissue, including tumors, benign growths (e.g., condylomas, papillomas) and malignant growths (e.g., cancer). As used herein, "neoplastic disease" refers to disease manifested by the presence of a neoplasm.

Replication Competent. As used herein, the term "replication-competent" virus refers to a virus that produces infectious progeny in neoplastic cells.

Substantially Free of Contaminating Egg Proteins. The term "substantially free of contaminating egg proteins" refers to a level of virus purity in which ovalbumin is not detectable in a Western blot as performed by one skilled in the art by (1) using $1.7 \times 10^9$ PFU of virus per well (3.3 cm in width) run on an SDS-PAGE (sodium dodecyl sulfate-polyacrylamide gel electrophoresis) gel (1 mm thick); (2) transferring the viral proteins from the gel to a nitrocellulose membrane; and (3) immunostaining for ovalbumin with the use of a rabbit anti-ovalbumin [Rabbit IgG fraction at a 1:200 dilution of a 4 mg/ml antibody concentration (from Cappel, Inc.) or equivalent polyclonal antibody] and, more advantageously, not detectable in an electrochemiluminescence assay with a sensitivity of 2.4 ng/ml.

Therapeutically effective amount. As used herein, the term "therapeutically effective amount" when referring to the treatment of neoplastic disease refers to a quantity of virus which produces the desired effect, e.g., cessation of neoplastic growth, tumor regression, improved clinical conditions, or increased survival.

COMPOUNDS OF THE INVENTION

A diverse group of viruses are used to selectively kill neoplastic cells. Natural or engineered viruses can function as an antineoplastic agent. These viruses i) infect neoplastic cells resulting in their death; ii) are replication-competent in the neoplastic cells; and iii) are limited in killing of normal cells by the antiviral effects of interferon.

In an advantageous embodiment of the invention, the viruses possessing the above three characteristics [(i) they infect neoplastic cells resulting in their death; (ii) they are replications-competent in the neoplastic cells; and (iii) they are limited in killing of normal cells by the antiviral effects of interferon] also induce interferon.

In another advantageous embodiment of the invention, the viruses possessing the above three characteristics also cause regression of human neoplasms; and/or are not neutralized in the target human population because of the presence of pre-existing immunity.

In another advantageous embodiment, the viruses possessing the above three characteristics are cytocidal to tumor cells.

A Paramyxovirus (as used herein "Paramyxovirus" refers to a member of the Paramyxoviridae) can be used according to the present invention to treat a neoplasm including a large tumor or a host having a high tumor burden. The Paramyxoviridae family comprises three genera: (1) paramyxoviruses; (2) measles-like viruses (morbilli viruses); and (3) respiratory syncytial viruses (pneumoviruses). These viruses contain an RNA genome. Use of Paramyxoviridae viruses which are cytocidal, especially paramyxoviruses, e.g., Newcastle disease virus ("NDV") and other avian paramyxoviruses such as avian paramyxovirus type 2, is an advantageous method of practicing the invention. Attenuated strains of these viruses are especially useful for treatment of neoplasms in accordance with the present invention.

NDV is an especially advantageous virus according to the present invention. NDV is categorized into three distinct classes according to its effects on chickens and chicken embryos. "Low virulence" strains are referred to as lentogenic and take 90 to 150 hours to kill chicken embryos at the minimum lethal dose (MLD); "moderate virulence" stains are referred to as mesogenic and take 60 to 90 hours to kill chicken embryos at the MLD; "high virulence" strains are referred to as velogenic and take 40 to 60 hours to kill chicken embryos at the MLD. See, e.g., Hanson and Brandly, 1955 (Science, 122:156-157), and Dardiri et al., 1961 (Am. J. Vet. Res., 918-920). All three classes are useful, advantageously, mesogenic strains of NDV such as strain MK107, strain N. J. Roakin, and strain Connecticut-70726. (see Examples 21-23). See, e.g., Schloer and Hanson, 1968 (J. Virol., 2:40-47) for a listing of other mesogenic strains.

For certain purposes, it is desirable to obtain a clonal virus to ensure or increase the genetic homogeneity of a particular virus strain and to remove defective interfering particles. Removal of defective interfering particles by cloning allows for increased purity in the final product as assessed by the number of total virus particles per infectious particle (e.g., the number of particle per PFU).

Clonal virus can be produced according to any method available to the skilled worker. For example, plaque purification is routinely utilized to obtain clonal virus. See, e.g., Maassab et al., In: Plotkin and Mortimer, eds. *Vaccines. Philadelphia*: W. B. Saunders Co., 1994, pages 781-801. Triple plaque purification is especially desirable, where a plaque is selected at each round of purification having the desired characteristics, such as a preferred size, shape, appearance, or representative of the parental strain. Another means of generating clonal virus is by recombinant DNA techniques applicable by one skilled in the art. Another means of obtaining a clonal virus applies the technique of limiting dilution (e.g., by adding dilutions of the virus samples to give an average of one or less infectious virus particles per well containing a monolayer of a susceptible cell).

In an advantageous embodiment of the invention, purified virus is used to treat neoplastic diseases. An advantageous method for purification of egg derived viruses are as follows (virus is not pelleted at any step in these methods):

Purification Method A
 a) generating a clonal virus (e.g., plaque purification)
 b) inoculating eggs with the clonal virus
 c) incubating the eggs
 d) chilling the eggs
 e) harvesting the allantoic fluid from the eggs
 f) removing cell debris from the allantoic fluid
 h) ultracentrifugation of the allantoic fluid without pelleting (e.g., using a discontinuous sucrose gradient)

In another embodiment of the invention, additional steps, added after the removal of the cell debris (from the allantoic fluid) and before ultracentrifugation, consist of:
 freezing then thawing the allantoic fluid
 removing contaminating material from the virus suspension (e.g., by means of centrifugation)

In another embodiment of the invention, ultracentrifugation is accomplished by means of a continuous flow ultracentrifuge.

One embodiment of the invention relates to a method of purifying a replication-competent RNA virus comprising the steps of:
 a) generating a clonal virus, and b) purifying said clonal virus by ultracentrifugation without pelleting.

Another embodiment of the invention involves a method of purifying a paramyxovirus (e.g., NDV) comprising purifying the virus by ultracentrifugation without pelleting. Optionally, the purifying step additionally comprises prior to the ultracentrifugation:
 a) plaque purifying to generate a clonal virus,
 b) inoculating eggs with the clonal virus,
 c) incubating the eggs,
 d) chilling the eggs,
 e) harvesting allantoic fluid from the eggs and,
 f) removing cell debris from the allantoic fluid.

Another embodiment of the invention involves a method of purifying a replication-competent clonal virus from eggs or cell culture comprising the step of ultracentrifugation without a step in which the virus is pelleted (see Example 31).

Another embodiment of the invention involves a method of the purifying a paramyxovirus (e.g., NDV) comprising purifying the virus by sequential tangential flow filtration (TFF). Optionally, the virus can be additionally purified by gel permeation chromatography, where each of these steps occurs in the presence of a stabilizing buffer (Example 15):
 a) plaque purifying to generate a clonal virus,
 b) inoculating eggs with the clonal virus,
 c) incubating the eggs,
 d) chilling the eggs,
 e) harvesting allantoic fluid from the eggs and dilution of allantoic fluid with buffer,
 f) removing cell debris from the allantoic fluid by TFF
 g) purification of the virus by TFF
 h) purification of the virus by gel permeation chromatography Optionally, the virus obtained from the gel permeation step can be concentrated using TFF.

Another embodiment of the invention involves a method of purifying a replication-competent clonal virus from eggs or cell culture comprising the step purifying the virus by sequential tangential flow filtration (TFF), and optionally followed by gel permeation chromatography, which can optionally be followed by TFF to concentrate the virus.

Clonal virus

Use of these methods permits purification of a clonal virus [including Paramyxovirus (e.g., NDV)] to at least $2 \times 10^9$ PFU/mg protein, advantageously to at least $3 \times 10^9$ PFU/mg protein, more advantageously to at least $5 \times 10^9$ PFU/mg protein, more advantageously to at least $1.0 \times 10^{10}$ PFU/mg protein, more advantageously to at least $2.0 \times 10^{10}$ PFU/mg protein, more advantageously to at least $3 \times 10^{10}$ PFU/mg protein, more advantageously to at least $4 \times 10^{10}$ PFU/mg protein, more advantageously to at least $5 \times 10^{10}$ PFU/mg protein, and most advantageously at least $6 \times 10^{10}$ PFU/mg. Use of these methods permits purification of a clonal virus [inducing Paramyxovirus (e.g., NDV)] to level in which the number of virus particles per PFU is less than 10, more advantageously less than 5, more advantageously less than 3, more advantageously less than 2, and most advantageously less than 1.2. (Lower numbers of virus particles per PFU indicating a higher degree of purity.)

RNA viruses

In another embodiment, these methods permit purification (to the levels cited above for clonal viruses) of an RNA virus [including (a) a cytocidal RNA virus; (b) a single-stranded RNA non-segmented, nonenveloepd virus; (c) a single-stranded RNA segmented, enveloped virus; (d) a double-stranded RNA segmented, nonenveloped virus; (e) and a single-stranded RNA non-segmented, enveloped virus (e.g., Paramyxovirus (e.g., NDV) and e.g., Retroviruses].

DNA viruses

In another embodiment, these methods permit purification (to the levels cited above for clonal viruses) of an interferon-sensitive cytocidal virus selected from the group consisting of (a) enveloped, double-stranded DNA viruses (including poxviruses); (b) nonenveloped, single-stranded DNA viruses; and (c) nonenveloped, double-stranded DNA viruses.

Egg derived viruses

In another embodiment, these methods permit purification of egg derived viruses to a level-substantially free of contaminating egg proteins. It is preferred to limit the amount of egg proteins in virus preparation for human therapeutic use since major egg proteins like ovalbumin are allergens.

Viruses useful in the treatment of neoplastic diseases including cancer are shown in Table 1. Additional examples of virus family members can be found in "Murphy A and Kingsbury D. W., 1990, In: *Virology*, $2^{nd}$ Edition (Ed. Fields, B. N.), Raven Press, New York" hereby incorporated in its entirety These viruses are optionally screened for naturally occurring variations (certain strains or isolates) that result in altered IFN production relative to the parental strain.

In another embodiment of this invention, candidate viruses, whether naturally occurring or engineered, are tested for the ability to provide therapeutic utility in the treatment of neoplasms. In one embodiment, the amount of candidate virus required to kill 50% of cells deficient in an interferon-mediated antiviral response, e.g., KB head and neck carcinoma cells, is compared to the amount of virus required to kill 50% of a similar number of cells competent in an interferon-mediate antiviral response, for example normal skin fibroblasts. The amount of killing is quantified by any number of means including trypan blue exclusion or MTT assay (see Example 1). A significant reduction (e.g., at least 5-fold) in the amount of virus required to kill cells deficient in an interferon-mediated antiviral response relative to the amount needed to kill cells competent in an interferon-mediated antiviral response indicates that the virus being tested exhibits activity required for therapeutic utility in the treatment of neoplasms. Other NDV viruses and Sindbis virus are such natural occurring viruses that display tumor-selective killing (see Examples 21-23, and 25).

TABLE 1

Naturally Occurring Viruses for Use in Cancer Therapy

| Virus Class | Virus Family | Virus Example |
|---|---|---|
| RNA, negative stranded | Paramyxoviridae | Newcastle Disease Virus<br>Avian Paramyxovirus Type 2<br>Measles<br>Mumps<br>Human Parainfluenza |
| | Orthomyxoviridae | Influenza Virus |
| | Rhabdoviridae | Vesicular Stomatitis Virus |
| RNA, positive stranded | Togaviridae | Sindbis Virus<br>Semliki Forest Virus |
| | Flaviviridae | Yellow fever (attenuated) |
| | Picornaviridae | Rhinovirus<br>Bovine enterovirus |
| | Coronaviridae | Avian infectious bronchitis virus<br>Human coronaviruses |
| RNA, double stranded | Reoviridae | Reovirus<br>Rotavirus |
| DNA | Poxviridae | Vaccinia virus |
| | Herpesviridae | Herpes Simplex Virus, type I |

An understanding of the factors involved in the establishment of an antiviral state allows for the creation of a screening assay for tumors that are likely to respond to viral therapy. In principle, patient derived tumor tissue obtained from biopsy is screened for the expression of p68 kinase, p58, or other factors involved in the regulation of an antiviral state or cellular differentiation. Other factors include, but are not limited to, interferon response factor-1 (IRF-1), interferon stipulatory gene factor-3 (ISGF-3), c-Myc, c-Myb, and IFN receptors. In the case of c-Myc, c-Myb or p58, high level expression indicates that the tumor tissue or cells are treatment candidates for virus therapy. In the case of p68, IRF-1, ISGF-3, and IFN receptors, low level expression indicates that the tumor tissue or cells are treatment candidates for virus therapy.

At least 30% of human tumors are characterized by an activated Ras phenotype (Bos, J. L., 1989, Cancer res., 49:4682). An activated Ras phenotype can occur as a result of i) expression of Ras proteins with activating mutations, ii) overexpression of wild-type Ras protein or, iii) expression of unregulated tyrosine kinase receptors or other members of the Ras signaling pathway such as Grb2 or Sos. Cells with activated Ras phenotype have been shown to more sensitive to killing by NDV (Lorence, R. M., et al., 1994, Cancer Res., 54:6017-6021) and by reovirus (Strong, J. E. S., et al., 1998, EMBO, 17:3351-3362) than the same cells without an activated Ras phenotype. Activated Ras has been shown to inhibit the induction of responsive genes by interferon (Zullo, J. N., and Faller, D. V., 1988, Mol. Cell. Biol., 8:5080-5085) and the activation of PKR by dsRNA (Mundschau, L. J., and Faller, D. V., 1992, J. Biol. Chem., 267:23092-23098). Given the key role that PKR plays in the induction of the interferon-mediated antiviral response, the increased sensitivity of cells with an activated Ras phenotype of killing by NDV and reovirus provides even more evidence for the selective killing of cells deficient in an interferon-mediated antiviral response by viruses of the present invention.

Patient derived tumor tissue obtained from biopsy can be screened for the expression of i) activated Ras protein, ii) the GTP-bound fraction of Ras (active form), iii) activated form of MAPK (e.g., ERK1 or ERK2), or other indices of an activated Ras pathway. The presence of an activated RAs phenotype in the patient specimen indicates that tumor tissue is a treatment candidate for virus therapy.

In another embodiment of this invention, primary tumor tissue or cells obtained from patient biopsies are expanded in culture and tested for sensitivity to killing by a suitable viral therapy. In one embodiment, the amount of virus required to kill 50% of the tumor tissue culture is compared to the amount required to kill 50% of a culture of normal cells as described above for the screening of candidate viruses. An increase of ten-fold or greater in the sensitivity of the tumor cells relative to normal cells to killing by the viral agent indicates that the tumor cells are specifically sensitive to the cytocidal effects of the viral treatment. In a further embodiment of the invention, the ability of the targeted tumor cells to respond to endogenously or exogenously supplied IFN is determined by conducting the above screen in the presence of IFN (alpha or beta form, using e.g., 10 units per ml, see Example 27).

An understanding of the cellular receptors required for virus attachment or entry will allow additional screening for tumors that have high receptor expression and hence enhanced sensitivity to the interferon-sensitive virus. This is an additional level screening for patients that are likely to respond to virus therapy. Advantageously for therapy with an interferon-sensitive virus, the patient's tumor would be both resistant to interferon as well as having high expression of the cellular receptor for the virus. In principle, patient derived serum, tumor cells, tissues, or tissue sections are screened by immunoassay or immunostain for the amount of virus receptors present in the serum or on the tumor cells or tumor tissue. For example, Sindbis virus utilizes the high affinity laminin receptor to infect mammalian cells (Wang et al., 1992, J. Virol., 66, 4992-5001). This same receptor is known to be expressed in higher amounts in many diverse types of metastatic cancer. The Panc-1 pancreatic cancer cell line, and the colon adenocarcinoma cell line SW620 are known to express a high level of high affinity laminin receptor mRNA (Campo et al, 1992, Am J Pathol 141:107301983; Yow et al., (1988) Proc. Natl Acad Sci. 85, 6394-6398) and are highly sensitive to Sindbis virus (Example 25). In contrast, the rectal adenocarcinoma cell line SW1463 is known to express very low levels of high affinity laminin receptor mRNA (Yow et al., (1988) Proc. Natl Acad Sci, 85, 6394-6398), and is more than 4 orders of magnitude more resistant to killing by PPSINDBIS-Ar339 than SW620 cells.

Existing strains of NDV, or other viruses including RNA and DNA viruses, are screened or engineered for altered IFN responses (e.g., advantageously increased IFN responses) in normal cells. In addition to the ability to elicit a strong IFN response, other viral characteristics are screened for or engineered into the virus. Viruses with altered receptor specificity (e.g., Sindbis virus PPSINDBIS-Ar339, see Example 25), or low neurovirulence are included in the subject invention (e.g., NDV virus PPNJROAKIN, see Example 24). Advantageously, viruses of the invention have the capacity to spread through direct cell to cell contact.

The invention described herein includes a broad group of viruses (see Table 1) that are useful for treatment of neoplasms in a manner analogous to the indication for NDV. In addition, viruses that naturally would not be candidates for use, due to the presence of a mechanism(s) to inactivate the IFN response to normal cells, are optionally engineered to circumvent the above restrictions. If left unmodified, viruses with mechanisms to inactivate the interferon response would be more toxic to normal cells than viruses with such mechanism removed. The subject invention provides (1) the development of a vector that can be easily manipulated; and (2) the creation of a set of therapeutic viruses. Manipulations include the addition of an IFN gene to permit the viral expression of a transgene expressing IFN, or other activators of the IFN response pathway. Additional permutations include the engineered expression of pro-drug activating enzymes such as the Herpesvirus thymidine kinase or cytosine deaminase (Blaese R M et al., 1994, Eur. J. Cancer 30A: 1190-1193) and the expression of suitable marker antigen to allow targeting of tumor cells by the immune system. An additional permutation include the engineered expression of receptor ligands to target cells with those receptors [e.g., expression of receptors to other viruses to target cells infected with those viruses (see Mebastsion et al., 1997, Cell 90:841-847; and Schnell M J et al., 1997, Cell 90:849-857].

Several Newcastle Disease virus strains in addition to the one cited above demonstrate selective killing of tumor cells. In a differential cytotoxicity assay using a second strain of mesogenic Newcastle Disease virus, tumor cells were found to be 3 orders of magnitude more sensitive than normal cells to killing by the virus (Example 21). Additionally, when a third mesogenic Newcastle Disease virus stain was used in a differential cytotoxicity assay, tumor cells were found to be 80 to 5000-fold more sensitive than normal cells to killing by the virus (Example 22). Both of these mesogenic Newcastle Disease virus stains also caused tumor growth regression following intratumoral administration to athymic mice bearing human tumor xenografts (Example 23).

In separate experiments, the safety of three distinct Newcastle Disease virus strains were studied following intracerebral inoculation in athymic and immune-competent mice. The results of this study showed that all three virus strains were well tolerated in mice with an intact immune system. Intracerebral inoculation into the brains of athymic mice revealed that one of the viruses was tolerated significantly better than the other two (Example 24). These results demonstrate that within a single virus family important differences in viral properties can occur and be can be exploited therapeutically for greater efficacy or increased safety.

Another means by which increased efficacy and lower toxicity following treatment with oncolytic viruses can be achieved is through the use of interferon-sensitive viruses that require specific cell surface receptor that are preferentially expressed on tumor cells. Sindbis virus provides an example of this type of restriction. Sindbis virus infects mammalian cells using the high affinity laminin receptor (Wang et al., (1992) J. Virol. 66, 4992-5001). When normal and tumor cells were infected with Sindbis virus in a differential cytotoxicity assay, cells which both were tumorigenic and expressed the high affinity laminin receptor were found to be more sensitive to killing by this virus than other cells (Example 25). Normal keratinocytes express the high affinity laminin receptor (Hand et al., (1985) Cancer Res., 45, 2713-2719), but were resistant to killing by Sindbis in this assay. Moreover, analysis of the interferon sensitivity and laminin receptor expression levels of normal keratinocytes and two different tumor cell lines demonstrate that PPSINDBIS-Ar339 selectively kills tumor cells that i) are deficient in an interferon-mediate antiviral response, and ii) express the high affinity laminin receptor.

PPSINDBIS-Ar339 also has potent tumor growth inhibitory properties when tested in vivo in athymic mice bearing subcutaneous SW620 adenocarcinoma tumors cells (Example 32).

Vesicular Stomatitis Virus (VSV) provides evidence for the generalized hypothesis of tumor-selective killing of by oncolytic viruses, i.e., an inherent deficiency in interferon responsiveness in tumor cells renders these cells sensitive to killing by interferon-sensitive replication-competent viruses. When VSV was used to infect non-tumorigenic human WISH cells and tumorigenic HT1080 or KB cells in the presence of exogenous interferon the tumorigenic cells were selectively killed (Example 26). Additional evidence is provided in Example 33. In this example, two unrelated viruses are shown to exhibit nearly identical behavior upon infection of a tumor cell line. The similar responsiveness of this cell line to each of these viruses demonstrates that the growth of the two unrelated viruses is controlled by similar mechanisms in this tumor cell line.

Below is a list of viruses that when modified to remove naturally-occurring anti-interferon activities, are useful for viral cancer therapy (see Table 2). Modified viruses (advantageously, but not necessarily, attenuated in addition to the anti-interferon modification, see Table 3) that have had endogenous anti-interferon activities destroyed or reduced, are useful for cancer therapy. This list includes, but is not be limited to, the viruses described below. Because of the similarity between viruses of a common class, the identified mechanisms for each of the specific viruses listed below, are also present in other members of that class of virus as identical or functionally analogous mechanisms. The broader group of viruses is added in parenthesis. Viruses, such as those below, that have a functional loss of anti-interferon activity, through any means, including natural occurring mutations, as well as engineered deletion or point mutations, are useful in the methods of the subject invention.

Viruses that exercise more than one mechanism are optionally modified to contain mutations in one, some, or all of the activities. Mutations for some of the described activities are available in the general scientific community.

Isolates of naturally occurring or engineered virus that are slower growing, compared to the growth rate of wild-type virus, are particularly advantageous because a slower virus growth rate will allow a cell or population of cells competent in an interferon response to establish an efficient antiviral state before viral replication can kill the cell or cell population.

The disabling of viral anti-interferon activities as a specific alteration of viral character that results in the augmentation of the interferon response in an infected cell, but still allows viral replication in neoplastic cells is included in the subject invention.

Table 2 shows existing viruses engineered to remove anti-interferon activity.

Table 3 lists viruses engineered to be attenuated in virulence.

TABLE 2

Extant Viruses Engineered to Remove Anti-IFN Activity

| Virus Class | Virus Family | Virus | Anti-IFN Activity | Reference |
|---|---|---|---|---|
| RNA | Reoviridae | reovirus | Omega-3 | Imani and Jacobs (1988) Proc Natl Acad Sci USA 85:7887-7891. |
| DNA | Poxviridae | Vaccinia | K3L | Beattle et al (1991) Virology 183-419 |
| | | | E3L | Beattle et al (1996) Virus Genes 12:89-94 |
| | | | B18R | Symons et al (1995) Cell 81:551-560 |
| | Adenoviridae | Various subtypes | VA-1 transcripts | Mathews and Shenk (1991) J Virol 64: 5657-5662 |
| | Alphaherpesviridae | HSV-1 | Gamma 34.5 gene product | Cho et al (1996) Proc Natl Acad Sci USA 92:10516-10520 |

TABLE 3

Known Attenuating Mutations in Selected Viruses

| Virus Class | Virus Family | Virus | Attenuation | Reference |
|---|---|---|---|---|
| RNA | Reoviridae | reovirus | Omega-1 | Springs and Fields (1982) Nature 297: 68-70 |
| | | rotavirus | Bovine strains (WC3) | Clark (1988) J Infect Dis 158:570-587 |
| | Togaviridae | Sindbis | Attenuating mutations in the E1 and E2 coding regions | Polo and Johnston (1990) J Virol 64: 4438-4444. |
| DNA | Poxviridae | Vaccinia | Vaccinia growth factor | Buller et al (1985) Virology 164:182 |
| | | | Thymidine kinase | Buller et al (1985) Nature 317:813-815 |
| | | | Thymidylate kinase | Hughes SJ et al (1991) J Biol Chem 266:20103-20109 |
| | | | DNA ligase | Kerr et al (1991) EMBO J 10:4343-4350 |
| | | | Ribonucleotide reductase | Child et al (1990) Virology 174:625-629 |
| | | | dUTPase | Perkus et al (1991) Virology 180:406-410 |
| | Adenoviridae | Various subtypes | Ad-4, Ad-7 and Ad-21 | Takafugi et al (1979) J Infect Dis 140:48-53 |
| | Alphaherpesviridae | HSV-1 | Thymidine kinase | Field and Wildy (1978) J Hyg 81: 267-277 |
| | | | Ribonucleotide Reductase | Goldstein and Weller (1988) Virology 166:41-51 |
| | | | Gamma 34.5 gene product | Chou et al (1995) Proc Natl Acad Sci USA 92:10516-10520 |
| | | | b'a'c' inverted repeats | Meigner et al (1988) J Infect Dis 162: 313-322 |

Treatment of Neoplasms

The present invention relates to viral therapy of neoplasms, especially in animals having cancer. In an advantageous embodiment, the invention relates to the treatment of tumors which are 1 centimeter (cm) or more in size as measured in the greatest dimension. As used herein, "a 1 cm tumor" indicates that at least one dimension of the tumor is 1 cm in length. Such tumors are more sensitive than expected to viral therapy, often at least as sensitive to virus, if not more sensitive, than tumors which are smaller in size. In a more advantageous aspect of the invention, tumors greater than 1 cm. are treated, e.g., tumors which are 2 cm or greater, from about 2 cm to about 5 cm, and greater than 5 cm.

The present invention can also be employed to treat hosts having a high tumor burden. As used herein, the phrase "tumor burden" refers to the total amount of tumor within the body expressed as a percentage as body weight. Viral therapy of hosts having a tumor burden, e.g., from about 1% to about 2% of total body weight is surprisingly effective, e.g., producing tumor regression and a reduction in the overall tumor load. This is especially unexpected since a tumor burden of approximately 2% of the total body weight (e.g., a 1 kg tumor in a 60 kg human) is approximately the maximum cancer mass compatible with life. See, e.g., Cotran et al., In *Robbins Pathological Basis of Diseases,* 4th Edition, W B Saunders, 1989, page 252. In the Examples, volumes up to 397 $mm^3$ for a melanoma cancer (e.g., A375) in a mouse host showed complete regression in response to treatment with a Newcastle disease virus (e.g., a triple-plaque purified virus). Assuming that for tissue 1000 $mm^3$ equals 1 gram, a tumor having a volume of 397 $mm^3$ comprises approximately 2% of the total body weight for a 20 gram mouse.

As shown in Examples 4 to 9 below, tumor regression was achieved with tumors at least 1 cm in size, while untreated, control animals began dying from tumor burden within several weeks. Thus, such diseased animals were successfully treated despite being within two weeks of death. Thus, in accordance with the present invention, an animal which is near terminal from its tumor burden can be treated effectively with viral therapy. Consequently, the present invention can be used to treat patients who have not responded to conventional therapy, e.g., chemotherapy such as methotrexate, 5-fluorouracil, and radiation therapy.

The efficacy of NDV for the treatment of cancer following administration through the intraperitoneal route has also been examined. Using an ascites prevention model of ovarian cancer, intraperitoneal injection of NDV in mice harboring ES-2 human ovarian tumors resulted in increased survival compared to mice treated with saline (Example 16). When ES-2 cells were used in an apparent ascites model, ascites fluid production was markedly decreased in virus-treated animals compared to saline controls (Example 17).

In another embodiment of the invention, the administration of virus results in 1) the relief of tumor related symptoms, such as but not limited to decreased rate of ascites fluid production, relief of pain, and relief of obstructive disease, and 2) the prolongation of life.

Fifty-two patients have receive the plaque purified NDV isolate by the intravenous route. Treatment responses include: regressions of individual tumors in 5 patients; stabilization of disease in 2 patients for 7 months, in 2 patients for 5 months and in 1 more patient that is ongoing at 3 months; and a reduction in pain medication (Example 20).

Administration and Formulation

In one embodiment of the invention, tumor cells or tissue are screened in vitro to determine those patients with tumors sensitive to the virus. Tumor cells removed from the patient (by methods such as fine needle aspiration for solid tumors or by parenthesis for ovarian ascites tumors) are grown in vitro and incubated with virus. In this embodiment of the invention, patients are selected for therapy if the virus has a high activity against their tumor cells.

In an advantageous embodiment of the invention, the amount of virus administered results in regression of the tumor or tumors. As used herein, the term "regression" means that the tumor shrinks, e.g., in size, mass, or volume. Shrinkage in tumor size is demonstrated by various methods, including physical examination, chest film or other x-ray, sonography, CT scan, MRI, or a radionucleotide scanning procedure.

Various types of neoplasms including cancers are treatable in accordance with the invention. The viruses of the present invention are useful to treat a variety of cancers, including but not limited to lung carcinoma, breast carcinoma, prostate carcinoma, colon adenocarcinoma, cervical carcinoma, endometrial carcinoma, ovarian carcinoma, bladder carcinoma, Wilm's tumor, fibrosarcoma, osteosarcoma, melanoma, synoviral sarcoma, neuroblastoma, lymphoma, leukemia, brain cancer including glioblastoma, neuroendocrine carcinoma, renal carcinoma, head and neck carcinoma, stomach carcinoma, esophageal carcinoma, vulvular carcinoma, sarcoma, skin cancer, thyroid pancreatic cancer, and mesothelioma. The viruses of the present invention are also useful to treat a variety of benign tumors, including but not limited to condylomas, papillomas, meningiomas, and adenomas.

A therapeutically effective amount of virus is administered to a host having a neoplasm. It is understood by those skilled in the art that the dose of virus administered will vary depending on the virus selected, type of neoplasm, the extent of neoplastic cell growth or metastasis, the biological site of body compartment of the neoplasm(s), the strain of virus, the route of administration, the schedule of administration, the mode of administration, and the identity of any other drugs or treatment being administered to the mammal, such as radiation, chemotherapy, or surgical treatment. These parameters are defined through maximum tolerated dose (MTD) determination in animal models and scaling to human dosage as a function of relative body surface area or body mass. It is also understood that under certain circumstances, more than one dose of the virus is given. The optimal interval between such multiple doses of the virus can be determined empirically and is within the skill of the art. NDV is generally administered from about $3 \times 10^6$ to about $5 \times 10^{12}$ PFU of virus. For local administration (e.g., directly into a tumor), total amounts of at least $3 \times 10^6$ PFU, more advantageously at least $3 \times 10^7$ PFU, more advantageously at least $3 \times 10^8$ PFU, more advantageously at least $3 \times 10^9$ PFU, more advantageously at least $3 \times 10^{10}$ PFU, more advantageously at least $3 \times 10^{11}$ PFU, and most advantageously at least $5 \times 10^{12}$ PFU are typically used. For systemic administration, amounts of at least $1 \times 10^8$ PFU of virus per square meter of body surface area, more advantageously at least $1 \times 10^9$ PFU of virus per square meter of body surface area, more advantageously at least $5.9 \times 10^9$ PFU of virus per square meter of body surface area, more advantageously at least $1.2 \times 10^{10}$ PFU of virus per square meter of body surface area, more advantageously at least $4.8 \times 10^{10}$ PFU of virus per square meter of body surface area, more advantageously at least $7.2 \times 10^{10}$ PFU of virus per square meter of body surface area, and more advantageously at least $9.6 \times 10^{10}$ PFU of virus per square meter of body surface area, and most advantageously at least $3.0 \times 10^{11}$ PFU of virus per square meter of body surface area are used.

For intravenous administration, dosing schedules of once per week, two times per week and three times per week are used. A virus in accordance with the present invention, optionally with a chemotherapeutic agent, can be administered by various routes, e.g., enteral, parenteral, oral, nasal, rectal, intrathecal, intravenous (e.g., using a catheter), subcutaneous, intratumor (e.g., directly into its tissue or into vessels which perfuse it), peritumoral, local, sublingual, buccal, topical, intramuscular, by inhalation, percutaneous, vaginal, intra-arterial, intra-cranial, intradermal, epidural, systemically, topical, intraperitoneal, intrapleural, intravesicular (for bladder tumors), etc. For lung tumors, a bronchial route (e.g., bronchial administration), a percutaneous routes, or an endoscopic route can be used. Endoscopic injections of gastrointestinal tumors, as well as suppository treatments of rectal tumors are also used where appropriate.

Murine toxicity studies with NDV have indicated that the acute toxicity following intravenous virus administration is likely to be caused by cytokine mediated reactions. Cytokine responses to repeated stimuli are known to be desensitized, or down-regulated, following the initial induction event (Takahashi et al., (1991) Cancer Res. 51, 2366-2372). Mice receiving a desensitizing dose of virus tolerate subsequent administration of higher doses better than saline treated controls (Example 18). Mice intravenously injected with a desensitizing dose of virus were able to tolerate approximately 10-fold more virus on an second intravenous dose than mice receiving vehicle alone for the first injection.

The rate of virus administration by the intravenous route can significantly affect toxicity. Two groups of athymic mice were intravenously treated with identical doses of NDV which was administered either slowly (0.2 ml over 4 minutes) or rapidly (0.2 mol over 30 seconds). Comparison of the maximal weight lose in each group revealed 50% less weight loss in the group receiving slow injection versus a rapid injection (Example 19).

In the clinical trail, patients received three injections of the plaque purified NDV isolate over the course of one week. Under these conditions, a desensitizing effect of the initial doses lessened the toxicity associated with the second and third doses, even when the second and third doses are two to eight times higher than the first dose (Example 20). These data parallel those obtained with the animal studies shown in Examples 18 and 28. Furthermore in the clinical trial, higher rates of tumor regression were noted when higher doses were achievable using a smaller desensitizing dose (see Table 19, Example 20). This again paralleled the data obtained in animal model testing (Example 29).

One concern related to the use of oncolytic viruses in the treatment of cancer is the potential inhibitory effect the humoral immune response can exert on the therapy. In the clinical study, patients displaying stable disease after 1 month are eligible for a second course of treatment. The second, and subsequent course of treatment are therefore administered in the presence of neutralizing antibodies to NDV. Nevertheless, infectious virus could be found in patients' urine after dosing for the second course and tumor regression was observed after a second course, providing evidence that administration of high doses of virus can overcome the effect of neutralizing antibodies and establish an infection within the patient (Example 20). In an advantageous embodiment of the invention, multiple courses of virus therapy are administered. Examples of a course include: administering virus 3× per week for 1 week, followed by a 3 week rest period; administering virus 3× per week for 4 weeks, followed by a 2 week rest period; administering one dose of virus, followed a 4 week rest period; administering 3× per week for 6 weeks, followed by a 2 week rest period. In another embodiment, virus is the administered more than 2 weeks after administration of the initial dose of virus.

In an advantageous embodiment of the invention, a desensitizing dose is given before higher subsequent doses. The desensitizing dose level is determined from clinical indicators of toxicity such as hypotension, fatigue, liver transaminase elevation or other appropriate indices, where the desensitizing dose level is equal to or below the maximum tolerated dose (MTD) for a single administration. Following desensitization, additional virus doses exceeding the desensitizing dose are given. In an advantageous embodiment, the subsequent virus doses are equal to or greater than the single dose MTD. For example, desensitizing virus doses of at least $1\times10^8$ PFU/m$^2$, more advantageously at least $3\times10^8$ PFU/m$^2$, more advantageously at least $1\times10^9$ PFU/m$^2$, more advantageously at least $5.9\times10^9$ PFU/m$^2$, and most advantageously at least $1.2\times10^{10}$ PFU/m$^2$ are used. After desensitization, additional virus doses at least $1\times10^8$ PFU/m$^2$, more advantageously at least $3\times10^8$ PFU/m$^2$, more advantageously at least $1\times10^9$ PFU/m$^2$, more advantageously at least $5.9\times10^9$ PFU/m$^2$, more advantageously at least $2.4\times10^{10}$ PFU/m$^2$, more advantageously at least $4.8\times10^{10}$ PFU/m$^2$, and more advantageously at least $9.6\times10^{10}$ PFU/m$^2$, and most advantageously at least $3.0\times10^{11}$ PFU/m$^2$ are used. In another embodiment, TNFα, IL-2, or other cytokines are administered, alone or in combination, for desensitization.

The time frame between doses including the time frame between desensitizing dose and the next dose is 1 to 14 days, advantageously 1 to 7 days. The desensitizing dose can be administered by various routes, e.g., intravenous, enteral, parenteral, oral, nasal, rectal, intrathecal, intravenous, subcutaneous, intratumor, peritumoral, local, sublingual, buccal, topical, intramuscular, by inhalation, percutaneous, vaginal, intra-arterial, intracranial, intradermal, epidural, systemically, topical, intraperitoneal, intrapleural, endoscopic, intrabronchial, etc. The subsequent doses can be administered by the same route as the desensitizing dose or by another route, e.g., intravenous, enteral, parenteral, oral, nasal, rectal, intrathecal, intravenous, subcutaneous, intratumor, peritumoral, local, sublingual, buccal, topical, intramuscular, by inhalation, percutaneous, vaginal, intra-arterial, intracranial, intradermal, epidural, systemically, topical, intraperitoneal, intrapleural, endoscopic, intrabronchial, etc. The usefulness of IV desensitization for subsequent dosing by another route is demonstrated in Example 28. Mice intravenously injected with a desensitizing doses of virus were able to tolerate approximately 5-fold more virus on an intraperitoneal second dose than mice receiving vehicle alone for the first injection.

In preclinical testing, the increase in the maximum tolerated dose achievable using desensitization allowed for increased antitumor efficacy as described in Example 29.

Optionally, more than one routes of administration can be used in either a sequential or concurrent mode. Routes for either concurrent or sequential administration include but are not limited to intravenous, enteral, parenteral, oral, nasal, rectal, intrathecal, intravenous, subcutaneous, intratumor, peritumoral, local, sublingual, buccal, topical, intramuscular, by inhalation, percutaneous, vaginal, intra-arterial, intracranial, intradermal, epidural, systemically, topical, intraperitoneal, intrapleural, endoscopic, intrabronchial, etc. An example would be the administration of a intravenous desensitizing dose followed by an intraperitoneal dose.

In another advantageous embodiment of the invention, the virus is administered by slow infusion including using an intravenous pump, syringe pump, intravenous drip or slow injection over the course of 4 minutes to 24 hours, advantageously between 20 and 60 minutes.

A virus, and optionally one or more chemotherapeutic agents, is administered by a single injection, by multiple injections, or continuously. The virus is administered before, at the same time, or after the administration of chemotherapeutic agents (such as but not limited to: busulfan, cyclophosphamide, methotrexate, cytarabine, bleomycin, platinum coordination complex such as carboplatin or cisplatin, doxorubicin, dacarbazine, gemcitabine, melphalan, mercaptopurine, vinblastine, 5-fluorouracil, taxol, and retinoic acid). Viral therapy in accordance with the present invention is optionally combined with other treatments, including, surgery, radiation, chemotherapy (see, e.g., *Current Medical Diagnosis and Treatment*, Ed. Tierney et al., Appleton & Lange, 1997, especially pages 78-94), and biological therapy. The virus is administered before, at the same time, or after the administration of biological agents such as (1) other oncolytic agents [such as but not limited to: adenovirus with one of its genes under transcriptional control of a prostate cell specific response element (see Rodriques, R. et al, 1997, *Cancer Res.* 57:2559-2563; adenoviruses which do not encode a Elb polypeptide capable of binding p53 (see Bischoff, J. R., et al, 1996, *Science* 274:373-376); a herpes simplex virus that is incapable of expressing a functional gamma 34.5 gene product (see Mineta, T. et al, 1995, *Nature Medicine*, 1:938-943)]; (2) cytokines (such as but not limited to: colony stimulating factors such as GM-CSF; tumor necrosis factor, and interleukins such as IL-1, IL-2, IL-6 and IL-10); (3) viral vectors [such as but not limited to adenovirus encoding p53 (see Zhang, W. W. et al, 1994, Cancer Gene Therapy, 1:5-13)]; and (4) cancer vaccines.

In one embodiment of the invention, therapy consists of the serial treatment with antigenically distinct viruses which are cytotoxic and tumor selective via the IFN mechanism. This embodiment allows viral therapy over an extended period without immunological interference.

Another embodiment involves the treatment of patients with IFN (e.g., αIFN, βIFN or γIFN) prior to, concurrent with, or following administration of NDV (or other virus). The IFN is selected from the group class I (alpha, beta and omega) and class II (gamma), and recombinant version and analogs thereof as discussed in, for example, Sreevalsoun, T., 1995 (In: *Biologic Therapy of Cancer*, second edition, edited by V. T. DeVita, Jr., S. Hellman, and S. A. Rosenberg, J. B. Lippincott Company, Philadelphia, pp347-364). Normal cells respond to the IFN pre-treatment with an augmented IFN response to viral infection affording even greater safety to these cells. Tumor cells deficient in the IFN signaling pathway remain sensitive to killing by the virus. This allows even higher doses of viral therapy to be used. The IFN is administered in accordance with standard clinical guidelines for doses and regimens known to be effective for treating viral infections.

In another embodiment of the invention, other drugs, known to affect the IFN response pathway are also optionally used to increase the sensitivity of tumor cells, or increase the resistance of normal cells to the cytocidal effects of viral infection. This class of durgs includes, but is not limited to tyrosine kinase inhibitors, cimetidine, and mitochondrial inhibitors. One strategy for enhancing oncolytic activity of therapeutic viruses of the invention involves disruption of mitochondrial oxidative phosphorylation. Preferred agents are clinically acceptable drugs that inhibit respiratory chain function or mitochondrial protein synthesis. 4-quinolone antibiotics, menadione, chloramphenicol, chloroquine, and tetracylcines are useful for potentiating oncolytic activity of anticancer viruses. Such agents are administrated in clinically tolerated doses 0 to 24 hours prior to administration of an oncolytic virus. Mitochondrial inhibitors are also optionally administered after the virus to further sensitize tumors supporting viral replication.

Hypoxia and hyperthermia are also known to modulate interferon responsiveness. Therefore, in one embodiment of the invention, hypoxic regions of tumors are oxygenated prior to or during exposure of tumors to a therapeutic oncolytic virus. Methods for accomplishing this include, but are not limited to, systemic administration of oxygenated fluorocarbon blood hemoglobin substitutes, erythropoietin, or vasodilators. Tumor oxygenation is also accomplished by delivering oxygen at supranormal concentrations in air via the lungs.

In another embodiment of the invention, immunosuppressants such as cyclosporin A, azathiaprime, leflunomide, anti-CD-40 ligand antibodies (Foy, T. M., et al., 1993, J. Exp. Med. 178:1567-1575) and various corticosteroid preparations such as, cortisol, predisone, prednisolone, 6α-methylprednisolone, fludrocortisone, corticosterone, triamcinolone, paramethasone, betamethasoneand, and dexamethasone are administered before, during, or after administration of the virus. Alternatively, immunostimulatory compound, e.g., lipopeptides, can be administered with the virus.

In another embodiment of the invention, agents which inhibit TNF-alpha activity such as antibodies against TNF-alpha (see Example 30), soluble TNF-alpha receptors, corticosteroids, or other compounds, are administered before, during or after the virus.

An independent mechanism by which the amount of interferon produced in response to viral infection is increased through the use of nucleosides (Machida, H., 1979. Microbiol. Immunol. 23:643-650), nucleoside precursors, or drugs that increase the cellular concentration of one or more nucleosides, are optionally used as an adjunct to viral therapy.

Certain purine nucleoside analogs, e.g., 2-chlorodeoxyadenosine and 2'-deoxycoformycin, reduce interferon production in vivo. Such compounds are used to further effect differences in interferon sensitivities of tumor cells versus normal cells and are optionally used as an adjunct to viral therapy.

In one aspect, an effective amount of virus can be subdivided into smaller dose units and injected at the same time into different locations of the same tumor. For continuous administration, the desired agent(s) is administered via an implanted minipump or it is impregnated into a desired polymer and then transplanted into a desired location (e.g., directly into the tumor) for slow or delayed release.

A virus of the present invention is formulated as a pharmaceutical preparation by bringing it into a suitable dose form, together with at least one excipient or auxiliary, and, if desired, with one or more further active compounds. The preparation are utilized in both human and veterinary medicine. Suitable excipient include, e.g., organic and inorganic substances which are appropriate for enteral or parenteral administration, e.g., water, saline, tissue culture media, buffers, lysine, citrate, glycerol triacetate and other fatty acid glycerides, gelatin, soya lecithin carbohydrates such as, mannitol, sucrose, lactose or starch, magnesium stearate, talc, cellulose or protein carriers, or a combination of the preceding compounds, such as mannitol/lysine, or mannitol/lysine/sucrose. The preparations are sterilized and/or contain additives, such as preservatives or stabilizers. For parenteral administration, e.g., systemic or local injection, a virus preparation is formulated, e.g., as an aqueous suspension or emulsion.

The invention also relates to a method of treating a disease in a mammal, in which the diseased cells have defects in an interferon-mediated antiviral response, comprising administering to the mammal a therapeutically effective amount of an interferon-sensitive, replication-competent, clonal virus. For example, many viruses have evolved mechanisms to ablate the interferon-mediated antiviral response of the host cell. The hepatitis B and hepatitis C viruses are leading cause of liver dysfunction worldwide. These viruses are associated with progressive liver damage, cirrhosis, and hepatocelluar carcinoma. Treatment with interferons is the current standard therapy for these diseases, but large segments of the population fail to respond to treatment, or suffer relapses following termination of therapy. The terminal protein of the hepatitis B virus (HBV) has been shown to inhibit the cellular responses to interferon, and double-stranded RNA, a known activator of PKR (Foster, G. R., et al., 1991, Proc. Natl. Acad. Sci., USA, 88:2888-2892). Additionally, the core antigen of HBV has been shown to inhibit the expression of the beta interferon gene (Whitten, T. M., et al., 1991, J. Virol., 65:4699-4704), and the HBV-associated delta agent has been shown to block the activity of PKR in rabbit reticulolysates (Robertson, H. D., et al., 1996, J Virol., 70:5611-5617). The hepatitis C virus (HCV) also possesses an activity that represses the PKR protein kinase. The NS5A protein of HCV has been shown to directly inhibit PKR protein kinase activity (Gale, M. J., et al., 1998, Clin. Diagn. Virol., 10:157-162). Patients failing initial interferon therapy for HBV or HCV infection are candidates for treatment with viruses of the current invention. The therapeutic virus, or viruses, are administered by any of the means described above, but would be advantageously administered intravenously or through the intrahepatic artery.

There is evidence that human immunodeficiency virus (HIV) infected cells are also resistant to the effects of interferon, and that resistance is correlated with the presence of AIDS (Kunzi, M. S., et al., 1995, J. Infect. Dis., 171:822-828; Edlin B. R., et al., 1992, Ann. Intern. Med., 117:457-460). Mechanistically, the TAR RNA region of HIV has been shown to interact with PKR and either activate or inhibit the activity of the kinase dependent on the concentration of TAR RNA (Maitra, R. K., et al., 1994, Virology, 204:823-827). Additionally, the cellular TRBP and the viral Tat proteins are known to bind to the HIV TAR RNA region and inhibit the activity of PKR (Davies, P. H., et al., 1994, Proc. Natl. Acad. Sci., 91:4713-4717; Brand, S. R., et al., 1997, J. Biol. Chem., 272:8388-8395). Cells infected with HIV and resistant to the effects of interferon are targets for killing by the viruses of this invention.

A number of other human viral pathogens are known to inhibit one or more components of the interferon-mediated antiviral state. Adenovirus and Epstein-Barr virus are all known to express abundant, small RNA species that block the activation of PKR in infected cells (for a review see Clemens, M. J., et al., 1994, Biochimie, 76:770-778). Epstein-Barr virus is nearly 100% associated with endemic Burkitt's lymphoma, in addition to poorly and undifferentiated nasopharyngeal carcinoma, and is the causative agent of infectious mononucleosis. Vaccinia virus has been shown to encode proteins, E3L and K3L, that block the activation of PKR and serve as false substrate for activated PKR kinase, respectively (Davies, M. V., 1993, J. Virol., 67:1688-1692). The E3L protein has also been shown to inhibit the 2'-5' synthetase component of the cellular antiviral response (Rivas, C., et al., 1998, Virology, 243:406-414).

A homolog of the vaccinia virus E3L protein has also been described in a human orf parapoxvirus (McInnes, C. J., 1998, Virus Genes, 17:107-115). Vaccinia virus also encodes a soluble form of the type I interferon receptor that inhibits the induction of an antiviral state by interferon (Symons, J. A., 1995, Cell, 81:551-560). A cellular inhibitor of the PKR kinase is inducted in cells infected with influenza virus (Lee, T. G., et Al., 1990, Proc. Natl. Acad. Sci. USA, 87:6208-6212) or poliovirus (Black, T. L., et al., 1989, J. Virol., 63:2244-2251). Herpes simplex I virus also encodes a protein (gamma 34.5) that antagonizes the PKR mediated shut-off of protein synthesis in infected cells (Chou, J. et al., 1995, Proc. Natl. Acad. Sci. USA, 92:10516-10520). The NS1 protein of influenza virus and the sigma 3 protein of reovirus have been shown to inhibit the activation of PKR by double-stranded RNA (Lu, Y., et al., 1995, Virology, 214:222-228; Imani, F. and Jacobs, B. L., 1988, Proc. Natl. Acad. Sci. USA, 85:7887-7891). In each of the above examples of viral interference with the cellular establishment of an antiviral state, treatment of infected cells with the viruses of the present invention leads to the selective killing of the infected cells.

Unless indicated otherwise herein, details and conditions of viral therapy of this invention are in accordance with U.S. application Ser. No. 08/260,536 whose disclosure is incorporated herein by reference in its entirety. The entire disclosure of all applications, patents and publications, cited above and in the figures are hereby incorporated by reference.

The following examples are illustrative, but not limiting of the methods and compositions of the present invention. Other suitable modifications and adaptations of a variety of conditions and parameters normally encountered in clinical therapy which are obvious to those skilled in the art are within the spirit and scope of this invention.

EXAMPLE 1

PPMK107, (a Triple Plaque Purified Isolate of the NDV Strain MK107) Demonstrates a Selective Cytotoxic Activity Toward Many Human Cancer Cells Compared to Normal Human Cells Human tumor cells and normal cells were grown to approximately 80% confluence in 24 well tissue culture dishes. Growth medium was removed and PPMK107 was added in 10 fold dilutions ranging from $10^6$ plaque forming units (PFU)/well to $10^{-1}$ PFU/well. Controls wells with no virus added were included on each plate. Virus was absorbed for 90 minutes on a rocking platform at 37° C. At the end of the incubation period, the viral dilution were removed and replaced by 1 ml of growth medium. Plates were then incubated for 5 days at 37° C. in 5% CO2, then assessed qualitatively for the amount of cytopathic effect (CPE). Cytotoxicity was quantified by using a colorimetric MTT (2-[4,5-dimethylthiazol-2-yl]-2,5-diphenyl tetrazolium bromide) assay (Cell Titer 96, catalog #G4000, Promega Corporation, Madison Wis. 53711) monitored at 570 nm, that detects mitochondrial enzyme activity (Mosman, T., 1983, J. Immunol. Methods 65:55). The viability in the virus treated wells was expressed as a percent of the activity in untreated control wells. The data was plotted graphically as PFU/well vs. viability as a percent of control. The IC50 was calculated as the amount of virus in PFU/well causing a 50% reduction in the amount of viable cells.

The results are given in Tables 4, 5 and 6. PPMMK107 demonstrated a high degree of cytotoxic activity against a diverse set of human cancer cells with 30 out of 39 malignant lines having an IC50 value less than 1000 compared to the relative insensitivity of normal human cell types. The majority of human cancer cells has IC50 values that were 2 to 3 orders of magnitude lower than most normal human cell types.

TABLE 4

Summary of Cytotoxicity Results

| TUMOR TYPE | CELL LINE | IC-50 (PFU/ml) |
|---|---|---|
| FIBROSARCOMA | HT1080 | 2 |
| PANCREATIC CARCINOMA | PANC-1 | 3 |
| RENAL CARCINOMA | CAKI-1 | 8 |
|  | CAKI-2 | 11 |
|  | A498 | 15 |
| LUNG CARCINOMA (Non-small cell) | H-1299 (low passage) | 26 |
|  | A427 | 2 |
|  | A549 | 13 |
| MELANOMA | SKMEL2 | 8 |
|  | SKMEL3 | 2 |
|  | SKMEL5 | 4 |
|  | A375 | 37 |
|  | MALME-3M | 778 |
|  | HT144 | 28 |
| BREAST CARCINOMA | SKBR3 | 10 |
|  | MDA-MB-468 | 44 |
|  | ZR75-1 | 78 |
| OVARIAN CARCINOMA | SW626 | 4 |
|  | PA-1 | 4 |
|  | ES-2 | 13 |
|  | SKOV-3 | 24 |
|  | OVCAR3 | 34 |
| GLIOBLASTOMA | U87MG | 25 |
|  | U373MG | 765 |
|  | U138 | 38 |
|  | A172 | 207 |
| BLADDER CARCINOMA | HT1197 | 3 |
|  | UM-UC-3 | 54 |
|  | HT1376 | 422 |
| NEUROBLASTOMA | IMR-32 | 41 |
| CERVICAL CARCINOMA | HeLa | 4 |
| PROSTATE CARCINOMA | DU-145 | 31 |
|  | PC3 | 3.1 E+03 |
| COLON CARCINOMA | SW620 | 55 |
|  | HT29 | >1.0 E+06 |
| HEAD AND NECK CARCINOMA | KB | 4 |
|  | A253 | 2.7 E+03 |
|  | FaDu | 2.9 E+03 |
|  | Hep-2 | 1.5 E+04 |
| NEUROEPITHELIOMA | SK-N-MC | 20 |
| SMALL CELL CARCINOMA (Lung) | DMS-114 | 48 |
|  | DMS-153 | 1.1 E+05 |
|  | NCI-H345 | 1.2 E+06 |
| SMALL CELL CARCINOMA (Prostate) | NCI-H660 | 1.0 E+05 |
| LEUKEMIA (AML) | K562 | 5.4 E+04 |
| LYMPHOMA (Burkitt's) | Ramos | >1.0 E+06 |
|  | Daudi | >1.0 E+06 |

TABLE 5

Summary of Cytotoxicity Assay Results Using Normal Human Cells.

| Cell Type | Cell | $IC_{50}$ (PFU/well) |
|---|---|---|
| Keratinocyte | NHEK | $9.0 \times 10^6$ |
| Fibroblast | CCD-922 | $1.4 \times 10^5$ |
|  | NHDF | $8.1 \times 10^3$ |
| Endothelial | HPAEC | $5.2 \times 10^4$ |
| Renal | RPTEC | $2.7 \times 10^4$ |
| Melanocyte | NHEM | $5.1 \times 10^4$ |
| Astrocyte | NHA | $3.8 \times 10^3$ |

TABLE 6

Summary of Cytotoxicity Assay Results Using Rapidly Proliferating Normal Human Cells.

| Cell Type | Rate of Proliferation In vitro | Rate of Proliferation In vivo | $IC_{50}$ (PFU/well) |
|---|---|---|---|
| Bone Marrow Cells, CD34+ Enriched to 50% | Moderate to High | High | $6.2 \times 10^3$ |
| Breast Epithelial Cells | Very low[a] | High[a] | 30 |

[a] Human breast epithelial cells tested (HMEC) had a high rate of proliferation after stimulation with bovine pituitary extract and human epidermal growth factor. In marked contrast, normal breast epithelial cells almost always have a very low degree of proliferation in adult women with cancer.

EXAMPLE 2

Use of PPMK107 for the Intratumoral Treatment of Human Tumor Xenografts (<10 mm and >5 mm) in Athymic Mice Athymic mice were injected intradermally with 10 million human tumor cells. After tumors reached a size range from between 5 and 10 mm, a single injection of PPMK107 (at a dose of $3\times10^8$ PFU) or saline was given. Almost all tumor types exhibited a rate of complete or partial regression of 50% to 100% (see Table 7) in mice treated with PPMK107. The one exception is the case of the U87MG experiment (experiment I): Although only one of 9 tumors treated with PPMK107 completely regressed, two more virus-treated tumors showed regression of 32% and 20% and two more virus-treated tumors had slower growth than all 8 tumors treated with saline control. Tumor regression was virtually absent in the saline control treated tumors: In all of these experiments (A through I listed in Table 7) only one of 73 control tumors showed regression. These results indicate that diverse tumor types showed responses to intratumoral PPMK107 treatment.

To examine virus replication within the tumor, immunohistochemical staining for viral antigen (using a monoclonal antibody against the NDV P protein) was performed using the subcutaneous HT1080 fibrosarcoma model. Within 30 minutes of intratumoral injection of $3\times10^8$ PFU of PPMK107, the tumor tissue was negative for viral antigen. However, by day 2 post treatment, intense immunostaining for viral antigen was seen within the tumor, indicating virus replication within the tumor. Importantly, virus replication was specific for the tumor tissue since the neighboring connective tissue and skin was negative for viral antigen.

TABLE 8

PPMK107 Intravenous Treatment of Subcutaneous Human HT1080 Fibrosarcoma Xenografts (<8.5 mm and >\5.5 mm) in Athymic Mice.

| Dose | Schedule | N | Complete Regression | Complete + Partial Regression | % Regression |
| --- | --- | --- | --- | --- | --- |
| 1.00E+09 | One Injection | 7 | 7 | 7 | 100% |
| 3.00E+08 | One Injection | 10 | 9 | 10 | 100% |
| 6.00E+07 | One Injection | 11 | 10 | 10 | 91% |
| 2.00E+07 | One Injection | 11 | 5 | 6 | 55% |
| 2.00E+07 | Three Injections every other day | 7 | 5 | 7 | 100% |
| Saline | One Injection | 10 | 0 | 0 | 0% |
| Saline | Three Injections Every Other Day | 6 | 0 | 0 | 0% |

TABLE 7

PPMK107 Intratumoral Treatment of Subcutaneous Human Tumor Xenografts (<10 mm and >5 mm) in Athymic Mice.

| Tumor | Tumor Type | Expt # | Dose | N | Complete Regression | Complete + Partial Regression |
| --- | --- | --- | --- | --- | --- | --- |
| HT1080 | Fibrosarcoma | A | 3.00E + 08 | 12 | 11 | 11 |
| | | B | 3.00E + 08 | 9 | 8 | 8 |
| | | B | 3.00E + 08 | 8 | 8 | 8 |
| PA-1 | Ovarian Carcinoma | D | 3.00E + 08 | 9 | 9 | 9 |
| KB | Oral Carcinoma | E | 3.00E + 08 | 12 | 7 | 10 |
| SKMEL5 | Melanoma | F | 3.00E + 08 | 8 | 5 | 7 |
| A375 | Melanoma | G | 3.00E + 08 | 8 | 5 | 7 |
| | | H | 3.00E + 08 | 1 | 1 | 4 |
| U87Mg | Glioblastoma | I | 3.00E + 08 | 9 | 1 | 1 |

EXAMPLE 3

Use of PPMK107 for the Intravenous Treatment of Human Tumor Xenografts (<8.5 mm and >5.5 mm) in Athymic Mice Athymic mice were injected intradermally with 10 million human HT1080 fibrosarcoma cells. After tumors reached a size range from between 5 and 8 mm, a intravenous injection(s) of PPMK107 or saline were made. As shown in Table 8, at the highest virus dose level ($1\times10^9$ PFU) complete tumor regression was seen in all seven mice. Single injections of $3\times10^8$ and $6\times10^7$ resulted in regression rates of over 90%. While a singe IV injection of $3\times10^8$ gave only a 55% rate of tumor regression, three IV injections at this dose level yielded a 100% rate of response. Mice treated with IV saline exhibited no evidence of tumor regression. These results indicate that subcutaneous HT1080 tumors are very responsive to IV treatment with PPMK107.

EXAMPLE 4

First Experiment Using PPMK107 for Intratumoral Treatment of Large A375 Melanoma Xenografts in Athymic Mice Athymic mice were injected intradermally with 10 million A375 human melanoma cells. Ten days later, tumors of various sizes were treated with a single injection PPMK107 (doses of $3\times10^8$, $9\times10^8$, and $1.5\times10^9$ PFU) or saline. For those tumor with a single largest dimension of 10 to 11 mm, all nine completely regressed in response to intratumoral treatment with these doses of PPMK107, while of those tumors with a single largest dimension of 8 to 9.5 mm, twelve out of 24 completely regressed in response to virus therapy (P<0.008; Table 9, section A). No tumor regression was seen in any mouse treated with saline.

These same tumors when sorted by tumor volume also indicated a high percentage of complete regression in those of larger tumor volume. In response to these doses PPMK107, complete regression occurred in 14 out of 17 tumors with volumes >300 mm$^3$ (range of 304 to 397 mm$^3$) and in 7 out of 16 tumors with volumes <300 mm$^3$ (range of 144 to 295; P<0.023; Table 9, section B).

These results indicate that tumors at least 1 cm in length or 300 mm$^3$ in volume were at least as sensitive, if not more sensitive, to intratumoral PPMK107 treatment than smaller tumors.

TABLE 9

Intratumoral PPMK107 Treatment of Intradermal A375 Melanoma Xenografts.

A. Tumors Sorted Based on the Single Largest Dimension

| Treatment | Dosage | Tumor Dimension: 8 to 9.5 mm | | | Tumor Dimension: 10 to 11 mm | | |
|---|---|---|---|---|---|---|---|
| | | N | Complete Regression | % | N | Complete Regression | % |
| PPMK107 | 1.5 × 10$^9$ | 8 | 2 | 25% | 3 | 3 | 100% |
| PPMK107 | 9.0 × 10$^8$ | 8 | 7 | 88% | 3 | 3 | 100% |
| PPMK107 | 3.0 × 10$^8$ | 8 | 3 | 38% | 3 | 3 | 100% |
| Total | | 24 | 12 | 50% | 9 | 9 | 100%[a] |
| Saline | | 6 | 0 | 0% | 0 | | 0% |

B. Tumors sorted Based on the Tumor Volume

| Treatment | Dosage | Tumor Volume: <300 mm$^3$ | | | Tumor Volume: >300 mm$^3$ | | |
|---|---|---|---|---|---|---|---|
| | | N | Complete Regression | % | N | Complete Regression | % |
| PPMK107 | 1.5 × 10$^9$ | 6 | 2 | 33% | 5 | 3 | 60% |
| PPMK107 | 9.0 × 10$^8$ | 4 | 3 | 75% | 7 | 7 | 100% |
| PPMK107 | 3.0 × 10$^8$ | 6 | 2 | 33% | 5 | 4 | 80% |
| Total | | 16 | 7 | 44% | 17 | 14 | 82%[b] |
| Saline | | 8 | 0 | 0% | 1 | 0 | 0% |

[a] P < 0.008 for complete regression in the PPMK107 10 to 11 mm group versus the PPMK107 8 to 9.5 mm treated group.
[b] P < 0.023 for complete regression in the PPMK107-teeated >300 mm$^3$ group versus the PPMK107-treated <300 mm$^3$ PPMK107-treated group

EXAMPLE 5

Second Experiment Using PPMK107 for Intratumoral Treatment of Large A375 Melanoma Xenografts in Athymic Mice Tumors were established as in Example 4 ten days after tumor cell inoculation. Treatment consisted of various doses of PPMK107 (3×10$^6$ PFU, 3×10$^7$, 3×10$^8$, and 1.5×10$^9$) or saline. For tumors 10 to 11.5 mm in single largest dimension, complete or partial (at least 50%) regression occurred in all 28 tumors treated with PPMK107 using these doses in contrast to no regression in any of the saline-treated mice (Table 10, section A).

When these same tumors were sorted by tumor volume, all 26 tumors greater than 300 mm$^3$ (range: 309 to 525 mm$^3$) regressed completely or partially (at least 50%) in response to PPMK107 in contrast to none of the saline treated mice (Table 10, section B).

These results confirm that tumors at least 1 cm in length or 300 mm$^3$ in volume are sensitive to intratumoral PPMK107 treatment.

TABLE 10

Intratumoral PPMK107 Treatment of Intradermal A375 Melanoma Xenografts.

A. Tumors 10 to 11.5 mm (sorted Based on the Single Largest Dimension)

| Tx | Dose | N | Complete | % | Complete + Partial | % |
|---|---|---|---|---|---|---|
| | 1.5 × 10$^9$ | 7 | 7 | 100% | 7 | 100% |
| | 3.0 × 10$^8$ | 7 | 6 | 86% | 7 | 100% |
| | 3.0 × 10$^7$ | 7 | 5 | 71% | 7 | 100% |
| | 3.0 × 10$^6$ | 7 | 5 | 71% | 7 | 100% |
| All PPMK107 Groups | | 28 | 23 | 82% | 28 | 100% |
| Saline | | 6 | 0 | 0% | 0 | 0% |

B. Tumors >300 mm$^3$ (sorted Based on the Tumor Volume)

| Tx | Dose | N | Complete | % | Complete + Partial | % |
|---|---|---|---|---|---|---|
| | 1.5 × 10$^9$ | 7 | 7 | 100% | 7 | 100% |
| | 3.0 × 10$^8$ | 7 | 6 | 86% | 7 | 100% |
| | 3.0 × 10$^7$ | 6 | 4 | 67% | 6 | 100% |
| | 3.0 × 10$^6$ | 6 | 4 | 67% | 6 | 100% |
| All PPMK107 Groups | | 26 | 21 | 81% | 26 | 100% |
| Saline | | 5 | 0 | 0% | 0 | 0% |

EXAMPLE 6

Third Experiment Using PPMK107 for Intratumoral Treatment of Large A375 Melanoma Xenografts in Athymic Mice Tumors were established as in Example 4 nineteen days after tumor cell inoculation. Intratumoral treatment consisted of various doses of PPMK107 (3×10$^8$, 3×10$^6$, 3×10$^5$, 3×10$^4$, 3×10$^3$, 3×10$^2$ PFU) or saline. For tumors 12.5 to 14 mm in single largest dimension (volume range: 632 to 787 mm$^3$; average volume 698 mm$^3$), tumor regressions of at least 50% occurred in two out of three mice treated with 3×10$^8$ PFU in contrast to no regression in both saline-treated mice (Table 11). Using the same dose of PPMK107 (3×10$^8$ PFU) to treat tumors with a single largest dimension of 10 to 12 mm (volume range: 320 to 600 mm$^3$; average volume: 411 mm$^3$), seven of 8 mice exhibited regression of at least 25% (P<0.001 for regression of at least 25% compared to the saline treated mice which exhibited no regressions, Table 11). Regression of at least 25% for tumors of length 10 to 12 mm tumors were also seen in mice treated with 3×10$^6$ PFU, 3×10$^5$ PFU, 3×10$^4$ PFU, and 3×10$^3$ PFU, but not for mice treated with 3×10$^2$ PFU or saline (Table 11).

These results confirm that tumors at least 1 cm in length or 300 mm$^3$ in volume are sensitive to intratumoral PPMK107 treatment.

TABLE 11

Third Experiment Using PPMK107 for the Intratumoral Treatment of
A375 Melanoma Xenografts (at least 10 mm in Size)

| Treatment | N | Avg Volume | Complete Regression | Partial[a] | >25% and 50%[b] | Total Number of Regression[c] | % Regressions[c] | |
|---|---|---|---|---|---|---|---|---|
| | | 12.5 to 14 mm Tumors Volume Range | | | | | | |
| 3.0E+08 | 3 | 632 to 787 | 698 | 1 | 1 | 0 | 2 | 67 |
| 3.0E+08 | 2 | 717 to 860 | 788 | 0 | 0 | 0 | 0 | 0 |
| | | 10 to 12 mm Tumors Volume Range | | | | | | |
| 3.0E+08 | 8 | 320 to 600 | 411 | 0 | 3 | 4 | 7 | 088 d |
| 3.0E+06 | 8 | 425 to 662 | 502 | 0 | 0 | 2 | 2 | 025 |
| 3.0E+05 | 8 | 245 to 600 | 421 | 0 | 0 | 1 | 1 | 013 |
| 3.0E+04 | 8 | 336 to 600 | 477 | 0 | 0 | 1 | 1 | 013 |
| 3.0E+03 | 8 | 281 to 542 | 349 | 2 | 0 | 0 | 2 | 25 |
| 3.0E+02 | 8 | 281 to 662 | 372 | 0 | 0 | 0 | 0 | 0 |
| Saline | 8 | 379 to 666 | 518 | 0 | 0 | 0 | 0 | 0 |

[a]Partial regression is defined as regression less 100% and equal to or greater than 50%.
[b]"Regression ">25% and <50% " is defined as tumor regression greater than 25% and less than 50%.
[c]Includes all tumor regressions that are at least 25%
d-P < 0.0001 for regression greater than 25% in the 3E+08 group versus the saline group.

EXAMPLE 7

Fourth Experiment Using PPMK107 for Intratumoral Treatment of Large A375 Melanoma Xenografts in Athymic Mice Tumors of largest dimension 10 to 12 mm were established as in Example 4 thirteen days after tumor cell inoculation. Intratumoral treatment consisted of a single injection of $3\times10^8$ PFU of PPMK107 or saline. Volumes of those tumors treated with PPMK107 ranged from 295 to 600 mm³ (average tumor volume of 437 mm³). Groups of mice in each treatment group were euthanized on days 0, 2, 3, 4, 7, and 14 for tumor histology. For those mice observed for a minimum of 4 days, eleven out of 12 mice treated with PPMK107 exhibited regression of at least 25% compared to none of 8 in the saline group (P<0.0001, Table 12). At 2 days after PPMK107 treatment, two tumors already exhibited signs of regression but the degree of regression was less than 25%.

EXAMPLE 8

Fifth Experiment Using PPMK107 for Intratumoral Treatment of Large A375 Melanoma Xenografts in Athymic Mice Tumors of largest dimension 10 to 12 mm were established as in Example 4 twenty days after tumor cell inoculation. Intratumoral treatment consisted of a single injection of $3\times10^8$ PFU of PPMK107 or saline. Volumes of those tumors treated with PPMK107 ranged from 361 to 756 mm³ (average tumor volume of 551 mm³). Nine out of 10 mice treated with PPMK107 exhibited a regression of at least 25% compared to none of 10 in the saline group (P<0.0001, Table 13).

EXAMPLE 9

First Experiment Using PPMK107 for Intravenous Treatment of Large HT1080 Fibrosarcoma Xenografts Athymic mice were injected subcutaneously with 10 million HT1080 human fibrosarcoma cells. Six days later, tumors were treated with a single injection PPMK107 (at a dose of $1.5\times10^9$ PFU) or saline. For those tumors 10 to 11 mm in single largest dimension, five out of six tumors completely or partially regressed in response to a single intravenous injection of PPMK107 compared to none of the saline treated tumors (Table 14, P<0.025). These results indicate that tumors at least 1 cm in length are sensitive to intravenous PPMK107 treatment.

TABLE 12

Fourth Experiment Using PPMK107 for the Intratumoral Treatment of A375
Melanoma Xenografts (at least 10 mm in Size)

| Treatment | Day Euthanized Post Treatment | N | Complete Regression | Partial[a] | >25% and 50%[b] | Total Number of Regressions[c] | % Regressions[c] |
|---|---|---|---|---|---|---|---|
| 3.0E+08 | 14 days | 3 | 0 | 2 | 1 | 3 | 100 |
| 3.0E+08 | 7 days | 3 | 0 | 2 | 1 | 3 | 100 |

TABLE 12-continued

Fourth Experiment Using PPMK107 for the Intratumoral Treatment of A375 Melanoma Xenografts (at least 10 mm in Size)

| Treatment | Day Euthanized Post Treatment | N | Regressions Complete Regression | Partial[a] | >25% and 50%[b] | Total Number of Regressions[c] | % Regressions[c] | |
|---|---|---|---|---|---|---|---|---|
| 3.0E+08 | 4 days | 3 | 0 | 2 | 1 | 3 | 100 | |
| 3.0E+08 | 3 days | 3 | 0 | 0 | 2 | 3 | 67 | |
| 3.0E+08 | All PPMK107 Groups | 12 | 0 | 6 | 5 | 11 | 92 | d, e |
| Saline | 14 days | 2 | 0 | 0 | 0 | 0 | 0 | |
| Saline | 7 days | 2 | 0 | 0 | 0 | 0 | 0 | |
| Saline | 4 days | 2 | 0 | 0 | 0 | 0 | 0 | |
| Saline | 3 days | 2 | 0 | 0 | 0 | 0 | 0 | |
| Saline | All Saline Groups | 8 | 0 | 0 | 0 | 0 | 0 | |

[a]Partial regression is defined as regression less 100% and equal to or greater than 50%.
[b]"Regression ">25% and <50%" is defined as tumor regression greater than 25% and less than 50%.
[c]Includes all tumor regressions that are at least 25%
d-P < 0.03 for Complete or Partial Regression in the PPMK107 group of 12 mice versus the saline group of 8 mice.
e-P < 0.0001 for all tumor regression at least 25% in the PPMK107 group of 12 mice versus the saline group of 8 mice.

TABLE 13

Fifth Experiment Using PPMK107 for the Intratumoral Treatment of A375 Melanoma Xenografts (at least 10 mm in Size)

| Treatment | N | Regressions Complete Regression | Partial[a] | >25% and 50%[b] | Total Number of Regressions[c] | % Regrensions[c] | |
|---|---|---|---|---|---|---|---|
| 3.0E+08 | 10 | 0 | 4 | 5 | 9 | 90 | d, e |
| Saline | 10 | 0 | 0 | 0 | 0 | 0 | |

[a]Partial regression is defined as regression less 100% and equal to or greater than 50%.
[b]"Regression ">25% and <50%" is defined as tumor regression greater than 25% and less than 50%.
[c]Includes all tumor regressions that are at least 25%
d-P < 0.05 for Complete or Partial Regression in the PPMK107 group versus the saline group.
e-P < 0.0001 for all tumor regression at least 25% in the PPMK107 group versus the saline group.

TABLE 14

Intravenous Treatment of Subcutaneous HT1080 Human Fibrosarcoma Xenografts in Athymic Mice. Tumor Size = 10-11 mm.

| Treatment | Dose | N | Complete Regression | % | Complete + Partial Regression | % |
|---|---|---|---|---|---|---|
| PPMK107 | 1.5E+09 | 6 | 4 | 67[a] | 5 | 83[a] |
| Saline | | 4 | 0 | 0 | 0 | 0 |

[a]P <0.025 (by Fisher's exact test) for complete or partial regression (at least 50% regression) in the PPMK107 treated group compared to saline group.

EXAMPLE 10

Specific Clearing of PPMK107 Infection from Normal but Not Tumor Cells

In order to examine the mechanism of tumor-specific killing by NDV strain PPMK107, representative tumor cells were chosen based on the following criteria: a) ability to form tumors as xenografts in athymic mice; b) the tumor xenografts are specifically killed in vivo following administration of PPMK107; c) the tumors cells exhibit killing by PPMK107 in vitro at virus concentration that are several logs below the concentration to kill resistant, normal cells; and d) tumor cells must be easily distinguished from the normal cells when present as a co-culture.

Xenograft tumors comprised of KB head and neck carcinoma cells exhibit 83% complete or partial regression in response to a single intratumoral injection of PPMK107, and more than four logs more sensitive to killing by PPMK107 in vitro than are normal primary skin fibroblasts (CCD922-sk), and are easily distinguished from CCD922-sk cells when present as a co-culture.

Accordingly, co-cultures of KB and CCD922-sk cells were infected at a multiplicity of infection (m.o.i., the ratio of virus added per cell) of 0.0005 and the course of the infection followed for 5 days by immunohistochemical staining for a viral antigen (NDV P protein). Infection of normal cells peaked at 2 days with little or no apparent cell death as determined by visual inspection of the cell monolayer. On the third day post-infection the amount of viral expression in the normal cells decreased significantly, while infection of the tumor cells was clearly apparent. The amount of viral antigen virtually disappeared in the normal cells on days 4 and 5, while the infection in the tumor cells progressed rapidly through the tumor cell population resulting in destruction of the majority of the tumor cells present in the co-culture.

Thus, normal cells were infected and easily cleared the infection in a manner consistent with the anti-viral effects of IFN. The tumor cells were unable to establish an anti-viral state in response and were killed by the unabated viral growth, despite the presence of physiologically effective concentrations of IFN secreted into the media by the normal cells.

EXAMPLE 11

Demonstration that Interferon is an Important Component of Viral Clearing in Normal CCD922-sk Cells The hypothesis that interferon was mediating the ability of CCD922-sk cells to clear the infection of PPMK107 was tested. Polyclonal neutralizing antibodies to human interferon-α or human interferon-β, used alone or in combination, were added daily to cultures of CCD922-sk cells infected with PPMK107 at an moi of 0.0005 and the progress of the infection followed for three days. The amount of viral antigen present in the cells increased in proportion to the concentration of neutralizing antibody, with the effect of the anti-interferon-β antibody being more marked than that of the ant-interferon-α antibody; consistent with reports that fibroblasts produce predominantly the beta form of interferon.

The ability to make the normally insensitive cells more susceptible to infection with PPMK107 through the addition of neutralizing antibody to interferon supports the hypothesis that a key difference between the sensitivity of normal and tumor cells to killing by PPMK107 lies in the ability of normal cells, but not tumor cells, to establish an interferon-mediated anti-viral response.

EXAMPLE 12

Demonstration that Interferon-β is an Important Component of Viral Clearing in Other Normal Cells In this experiment, it was determined that another normal cell (NHEK, normal human epithelial cells) known to be quite resistant to killing by PPMK107, was made more sensitive through the addition of polyclonal anti-interferon-β antibody to a culture of infected cells. NHEK (normal human epithelial keratinocytes) cells were infected at an moi of either 0.0005 or 0.05 and had antibody added daily over five days.

In the cultures infected at the low moi (0.0005), antibody dependent augmentation of viral antigen expression was clear at five days post-infection, but was less clear earlier in the experiment. Antibody addition to cultures infected with PPMK107 at an moi of 0.05 resulted in a marked increase in viral antigen at 4 and 5 days post-infection. At 2 and 3 days post-infection the addition of neutralizing antibody resulted in less accumulation of viral antigen (FIG. 1).

The culture supernatants from the high moi samples were also titrated for the amount of infectious virus present by plaque assay or human HT1080 fibrosarcoma tumor cells; the standard assay system in our laboratory. Results from this analysis demonstrated that at five days post-infection there was 19-fold increase in the amount of infectious virus in the antibody-treated cultures relative to mock-treated controls (FIG. 1).

These results suggest a general mechanism by which normal cells are protected from killing by PPMK107 through an interferon-related mechanism.

EXAMPLE 13

Figure 2:
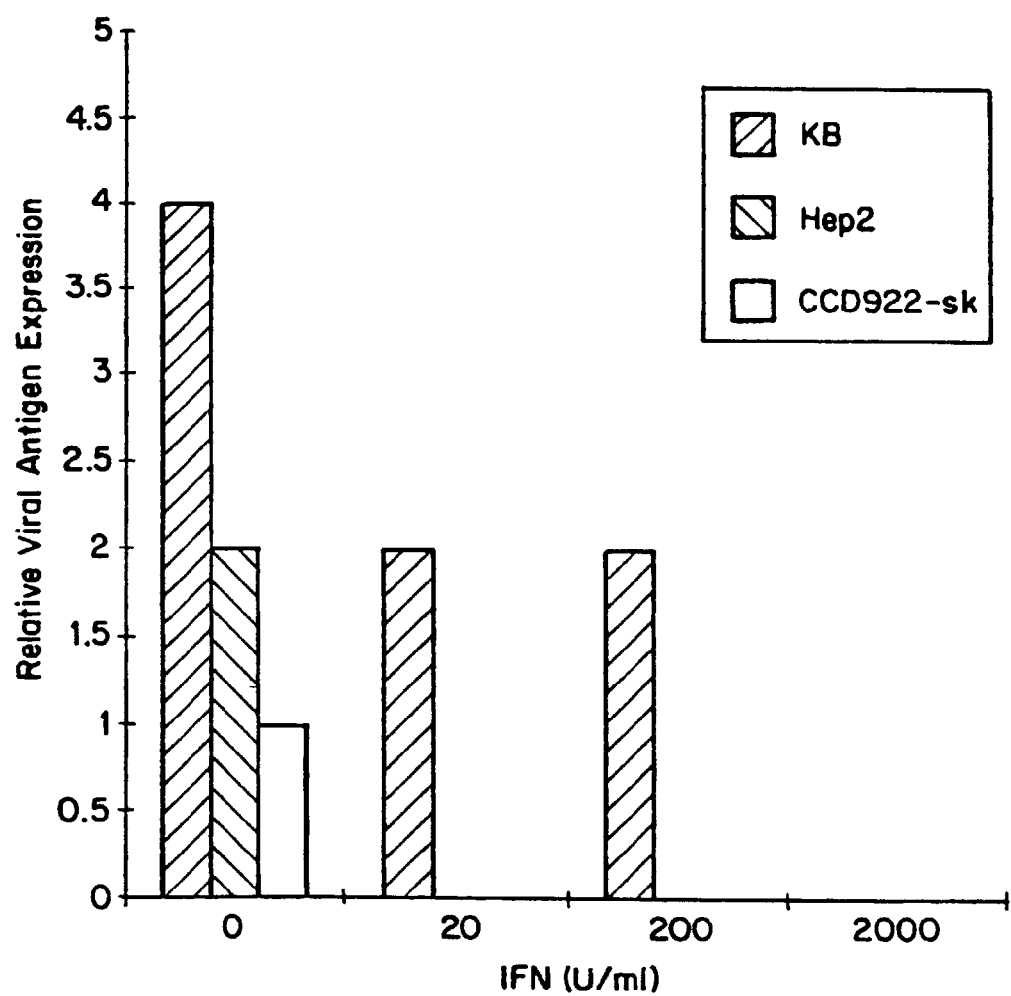
FIG. 2 shows the effect of interferon-beta on viral antigen expression in different cells (normal human skin fibroblasts CCD922-sk and two types of head and neck carcinoma cells (KB and Hep2 cells).

Comparison of the Effect of Interferon-β on PPMK107 Infection in Tumor and Normal Cells A comparison of the effect of exogenously added interferon-β on the infection of normal (CCD922-sk) and tumor cells of high (KB) or intermediate (HEp2) sensitivity PPMK107 was performed. Separate cultures of the three cells were treated with interferon-β at 20, 200, or 2000 units/ml 1 day pre- and 2 days post-infection at an moi of 0.0005. At 3 days post-infection the low level of viral antigen expression present in the normal cells was eliminated at all doses of interferon used. Conversely, the addition of interferon to the highly sensitive KB tumor cells at concentration of 2 or 200 units/ml decreased relative levels of viral antigen expression 2-fold, with complete suppression at 1000 units/ml interferon. The intermediately sensitive HEp-2 cells responded to the exogenous interferon by clearing viral antigen expression at all of the interferon doses used (FIG. 2).

The pattern of sensitivity in the KB and CCD922-sk cells to the anti-viral effects of exogenously added interferon-β was inversely proportional to the sensitivity of these cells to killing by PPMK107. The ability of the HEp-2 cells to response to the effects of interferon indicates that these cells are able to efficiently utilize the concentrations of interferon used in this experiment. Similarly, the response of the KB cells to the high doses of interferon suggests that the inability of establish an interferon-mediated anti-viral response does not result from an absolute defect in the interferon pathway, but rather a relative insensitivity compared to normal cells.

EXAMPLE 14

Effect of Low Concentrations of Interferon-β on the Infection of Normal and Tumor Cells by PPMK107

In this experiment normal (CCD922-sk) and tumor (KB) cells were treated with low concentrations of interferon-β (0.2, 2, and 20 units/ml) 1 day before and 2 days post-infection with PPMK107 at an moi of 0.05.

Figure 3A:
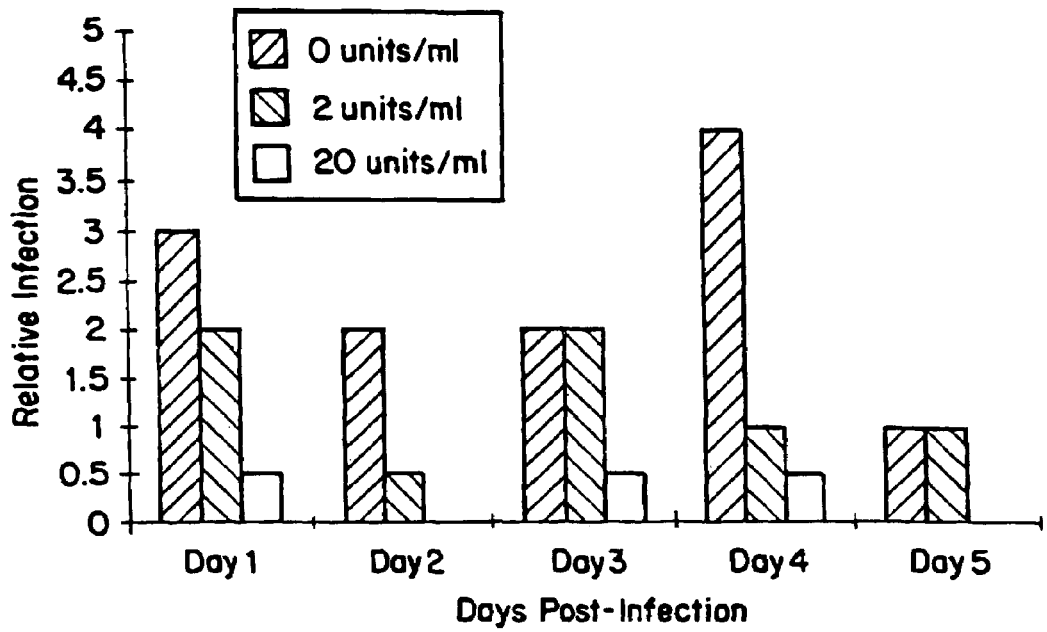
FIG. 3A shows the effect of interferon on viral antigen expression in CCD922-sk cells.
Figure 3B:
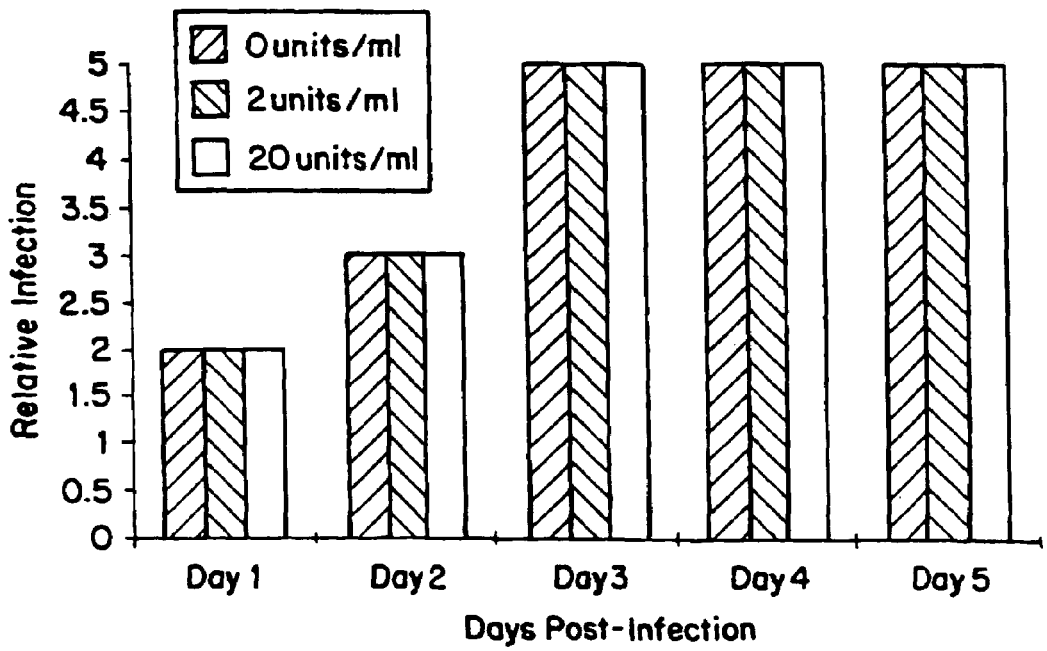
FIG. 3B shows the effect of interferon on viral antigen expression in KB cells.
Figure 4:
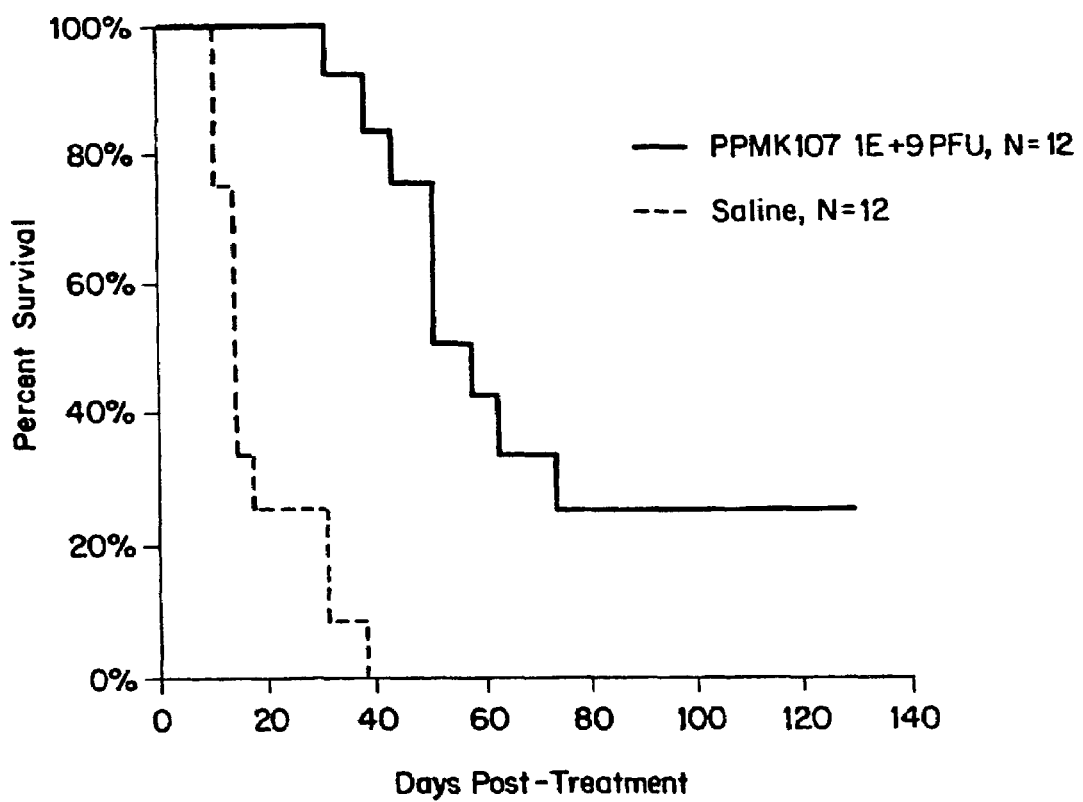
FIG. 4 shows the survival curves for athymic mice bearing human ovarian ES-2 tumors and treated with either saline or NDV.

Under these conditions the normal cells experienced a dose-dependent decreased in the amount of viral antigen, while the relative levels of viral antigen in the tumor cells was unaffected by the addition of exogenous interferon (FIG. 3).

EXAMPLE 15

PPMK107 Purification

Method A

PPMK107 was derived from the mesogenic Newcastle disease virus strain Mass-MK107 by triple plaque purification. Approximately 1000 PFUs (plaque forming units) of live PPMK107 were inoculated into the allantoic fluid cavity of each 10 day old embryonated chicken egg. After incubation at 36° C. for 46 hours, the eggs were chilled and then the allantoic fluid was harvested. Cells and cell debris were removed from the allantoic fluid by centrifugation at 1750×g for 30 minutes. The clarified allantoic fluid (supernatant containing virus) was then layered over a 20%/55% discontinuous sucrose gradient) and centrifuged at approximately 100, 000×g for 30 minutes. The purified virus was harvested from the 20%/55% interface and dialyzed against saline to remove the sucrose.

Method B

In another advantageous embodiment, the clarified allantoic fluid was frozen at −70° C. After thawing, the fluid was maintained at 1 to 4° C. overnight and then the contaminating material was removed from the virus suspension by means of centrifugation (1750×g for 30 minutes). This material was further processed using the discontinuous sucrose gradient on the ultracentrifuge as above.

Method C

In another advantageous embodiment, ultracentrifugation on the discontinuous sucrose gradient was accomplished by means of a continuous flow ultracentrifuge.

Method D

In another advantageous embodiment, harvested allantoic fluid is diluted with a buffer containing 5% mannitol and 1.0% 1-lysine, pH 8.0 (ML buffer) and is clarified and exchanged with ML buffer by tangential flow filtration (TFF) through filters with a nominal pore size of 0.45 μ. The permeate containing the clarified virus in ML buffer is collected and virus is purified by TFF through filters with a nominal cut-off of 300,000 daltons in ML buffer. The concentrated, purified virus in ML buffer is collected as the retentate from this step and is again diluted with ML buffer before being applied to a Sephacryl S500 (Pharmacia) gel permeation column equilbrated with ML buffer. Fractions containing purified virus are collected, pooled and can be reconcentrated by TFF through filters with a nominal cut-off of 300,000 daltons with ML buffer.

Results

Clonal Virus

After generation of PPMK107 by plaque purification, eight individual molecular clones from the population of virions were found to have an identical sequence (e.g., a homology of 100%) of over 300 contiguous nucleotides within the fusion protein gene of NDV. PPMK107 is a clonal virus with a high degree of genetic homogeneity.

PFU/mg protein

One quantitative means of measuring purity is by determination of a PFU/mg protein. The activity of the virus preparation was determined by the plaque assay method using HT1080 and the protein content of the virus preparations was determined using the Modified Lowrey Assay (Bio-Rad, Hercules, Calif.) with bovine serum as the protein standards. Higher values indicate a greater level of purity. Using Method A, PFU/mg values of at least $4.8\times10^{10}$ were achieved (see Table 15). Using Method C, PFU/mg protein values of at least $2.0\times10^{10}$ were achieved. For a mesogenic strain of NDV, a literature value for this measurement of purity has not been found. The best estimate for a mesogenic strain of NDV is the virus preparation (NDV MassMK107, lot RU2, prepared as in Faaberg K S and Peeples, M E, 1988, J Virol 62:586; and Bratt, M A and Rubin, H. 1967, Virology 33:598-608). This RU2 lot was found to have a PFU/mg of $1.3\times10^9$ PFU/mg of protein. The purity values achieved by Method A are approximately 40 times better than what the Peeples method achieved (see Table 15).

Particle per PFU Ratio

Another quantitative means of measuring purity is by determination of a ratio of particles per PFU. Lower values indicate a greater level of purity. Particle counts were done by electron microscopy using standard methods. Using either Method A or Method B, particles per PFU values near one were achieved (Table 15).

TABLE 15

Virus Purity

| Virus Preparation Method | Virus | Lot # | PFU per mg protein | Particle per PFU |
|---|---|---|---|---|
| Preferred Method A | PPMK107 | L2 | $4.8 \times 10^{10}$ | 0.80 |
| | | L4 | $6.9 \times 10^{10}$ | NT[a] |
| | | L5 | $6.6 \times 10^{10}$ | NT |
| | | L6 | $7.7 \times 10^{10}$ | 0.55 |
| | | L7 | $6.1 \times 10^{10}$ | NT |
| Preferred Method C | PPMK107 | D004 | $2.0 \times 10^{10}$ | 0.32 |
| | | D005 | $4.5 \times 10^{10}$ | 0.52 |
| | | D010 | $4.4 \times 10^{10}$ | NT |
| Preferred Method D | PPMK107 | RD2 | $5.6 \times 10^{10}$ | NT |
| | | RD3 | $5.0 \times 10^{10}$ | NT |

[a]NT, Not Tested

Virus preparations using Methods A and C also permitted purification of NDV to a level substantially free of contaminating egg proteins. For the PPMK107 lot 7 preparation using Method A ovalbumin, was not detectable in a Western blot using (1) $1.7\times10^9$ PFU of purified virus per well (3.3 cm in width) run on an SDS-PAGE (sodium dodecyl sulfate-polyacrylamide gel electrophoresis) gel (1 mm thick); (2) a nitrocellulose membrane for transfer; and (3) rabbit anti-ovalbumin (Cappel rabbit IgG fraction at a 1:200 dilution of a 4 mg/ml antibody concentration). For PPMK107 preparations using Method D and analyzed by SDS-PAGE followed by silver staining, no band corresponding to ovalbumin was observed.

EXAMPLE 16

PPMK107 Treatment of Ascites-Forming ES-2 Ovarian Carcinoma in Athymic Mice

In this experiment, all of the athymic mice (female, NCR nu/nu, 8 weeks old) were given an intraperitoneal injection of $10^6$ ES-2 cells. Seven days later before ascites had developed, they were treated intraperitoneally with saline or PPMK107 (at $1\times10^9$ PFU). As shown in FIG. 4, there was a markedly improved survival in the animals treated with PPMK107 compared to saline. The majority of the mice in the saline treated group has developed ascites by seven days post-treatment and by day 38, all of these animals had died. In marked contrast, 92% of the mice treated with PPMK107 were still alive by day 38 and 25% of these animals were long term survivors (>120 day survival).

EXAMPLE 17

PPMK107 Treatment of ES-2 Ovarian Carcinoma in Athymic Mice When Ascites is Present In this experiment, all of the athymic mice (female, NCR nu/nu, 8 weeks old) were given an intraperitoneal injection of $10^6$ ES-2 cells. Fourteen days later when the majority of mice had developed ascites, the mice without ascites were excluded and the mice with ascites were randomized into 7 intraperitoneal treatment groups (PPMK-107—one treatment on day 0; PPMK107—two treatments for the first week; PPMK107—one treatment per week; PPMK107—two treatments per week; saline—one treatment on day 0; saline—two treatments for the first week; saline—two treatments per week). A dose of $1\times10^9$ PFU/mouse was used for each virus treatment. All of the mice before the first treatment and any additional treatments were drained of the ascites fluid.

The degree of ascites was quantified and noted as follows:

| Ascites Score | Degree of Ascites |
|---|---|
| 1.0 | Animal appears normal- little or no ascites present |
| 2.0 | Abdomen slightly distended; animal is capable of normal functions |
| 3.0 | Abdomen distended; animal is slow-moving, hunched with a staggered gait. |
| 4.0 | Abdomen completely distended; animal moribund |
| 5.0 | Death after ascites development |

As shown in Table 16, all of the saline-treated animals had more advanced ascites than the PPMK107-treated animals on both days 7 and 10. On day 7 post initial treatment, each the saline group had ascites scores above 3.5 while all of the PPMK107-treated animals had ascites scores at 3.0 or below. Similarly on day 10 post initial treatment, each the saline group had ascites scores above 4.5 while all of the PPMK107-treated animals had ascites scores at 4.1 or below. These results indicate that ascites fluid production was markedly decreased in virus-treated animals compared to saline controls.

TABLE 16

PPMK107 Treatment of ES-2 Ovarian Carcinoma in Athymic Mice When Ascites is Present.

| Treatment | # of Mice | Ascites Score, Day 7 | Ascites Score, Day 10 |
|---|---|---|---|
| Saline ×1 | 12 | 4.3 | 4.7 |
| Saline ×2 | 12 | 3.7 | 4.6 |
| Saline ×2 per wk | 12 | 4.3 | 4.8 |
| PPMK107 × 1 | 17 | 3.0 | 4.1 |
| PPMK107 × 2 | 17 | 2.3 | 3.6 |
| PPMK107 ×1 per wk | 17 | 2.6 | 2.6 |
| PPMK107 ×2 per wk | 17 | 2.2 | 3.6 |

EXAMPLE 18

Use of a Desensitizing Dose of PPMK107 to Reduce the Lethality of a Subsequent Dose of PPMK107

C57BL/6 mice (seven weeks old) were injected intravenously on day 0 with either saline or a desensitizing dose of PPMK107 ($3\times10^8$ PFU/mouse). Two days later each set of mice were further subdivided into groups for intravenous dosing with saline or PPMK107 (at doses of $1\times10^9$, $2.5\times10^9$, $5\times10^9$, and $1\times10^{10}$ PFU/mouse). As shown in Table 16 below, when saline was used to pretreat the mice, deaths were recorded in the mice subsequently dosed with $2.5\times10^9$, $5\times10^9$, and $1\times10^{10}$ PFU. The doses of $5\times10^9$ and $1\times10^{10}$ PFU were 100% lethal to the mice pretreated with saline. In contrast, no deaths were seen in any group of mice given a desensitizing dose of PPMK107 on day 0 followed by PPMK107 injection two days later at dose levels up to $1\times10^{10}$ PFU. These data indicate that PPMK107 can be used to desensitize the lethality of subsequent dosing with this same agent. Furthermore, the maximal tolerated dose of PPMK107 can be raised by an approximate order of magnitude when using this virus as a desensitizing agent.

TABLE 17

Use of a Desensitizing Dose of PPMK107 to Reduce the Lethality of a Subsequent Dose of PPMK107.

| Group | Injection on Day 0 | Dose on Day 2 | # of Mice | # of Deaths | % Lethality |
|---|---|---|---|---|---|
| 1 | Saline | Saline | 8 | 0 | 0 |
| 2 | Saline | PPMK107, 1.0E+09 | 8 | 0 | 0 |
| 3 | Saline | PPMK107, 2.5E+09 | 8 | 3 | 38 |
| 4 | Saline | PPMK107, 5.0E+09 | 8 | 8 | 100 |
| 5 | Saline | PPMK107, 1.0E+10 | 8 | 8 | 100 |
| 6 | PPMK107, 3E+08 | Saline | 8 | 0 | 0 |
| 7 | PPMK107, 3E+08 | PPMK107, 1.0E+09 | 8 | 0 | 0 |
| 8 | PPMK107, 3E+08 | PPMK107, 2.5E+09 | 8 | 0 | 0 |
| 9 | PPMK107, 3E+08 | PPMK107, 5.0E+09 | 8 | 0 | 0 |
| 10 | PPMK107, 3E+08 | PPMK107, 1.0E+10 | 8 | 0 | 0 |

EXAMPLE 19

Slower Intravenous Injection Rate Reduces the Toxicity of PPMK107

Twenty two athymic mice (8 weeks old) were anesthetized with a combination of ketamine/xylazine and placed into a restrainer to help inhibit their movement during the injection process to allow for either a slow or rapid injection of PPMK107. For the slow injection group, 0.2 mL of $4\times10^9$ PFU of PPMK107 in saline was injected intravenously over a 4 minute period with 0.01 mL given every 10 to 15 seconds. The rapid injection group received the same dose and volume but over a 30 second period. As shown in Table 18, the animals receiving their dose of PPMK107 over 4 minutes had half as much maximal weight loss (recorded on day 2 after dosing) as the animals receiving the same IV dose over 30 seconds. These results indicate that PPMK107 has less toxicity and is safer for intravenous administration when injected at such slower rates.

TABLE 18

Slower IV Injection of PPMK107 Results in Reduced Toxicity.

| Group | Length of Time That Dose was Administered | # of Mice | Maximal Percent Weight Loss |
|---|---|---|---|
| Rapid Injection of 4E+09 | 30 seconds | 11 | 12% |
| Slow Injection of 4E+09 | 4 minutes | 11 | 6% |

EXAMPLE 20

Use of PPMK107 in the Treatment of Patients with Advanced Cancer

PPMK107 is currently being tested in a phase I clinical trail in the U.S.A. by the intravenous route. To date, a total of 52 patients with advanced solid tumors, no longer amenable to established therapies, have been treated with PPMK107. Seventeen of these patients have received a single dose for the initial treatment course. Thirteen other patients have received three of the same doses per week for one week for the initial treatment course. Twenty-two more patients have received three doses per week for one week for the initial treatment course with the first dose a desensitizing dose of 12 billion PFU/m$^2$ and the two subsequent higher doses of between 24 to 96 billion PFU/m$^2$. The sizes of each patient's tumors were followed once per month. Patients with at least stable disease (less than 25% increase and less than 50% decrease in the sum of the products of all measurable tumors in the absence of any new lesions) were eligible for additional treatment courses each month.

Regressions of Individual Tumors in Cancer Patients

Regressions of individual tumors were observed in 5 patients (one in the single dose regimen, one patient in the repeat same dose regimen and three patients in the desensitizing dose regimen; Table 19). A higher rate of tumor regression (16% of patients) was noted in those receiving higher second and third doses as part of the desensitizing regimen than when patients received three of the same doses in the repeat same dose regimen (8% tumor regression).

TABLE 19

Regression of Individual Tumors in Patients with Advanced Cancer using PPMK107.

| Regimen | # of Patients Treated at this Dose Level | # of Patients with Tumor Regressions | % of patients with Tumor Regression | Types of Cancer with Tumor Regression |
|---|---|---|---|---|
| Single Dose | 17 | 1 of 17 | 6% | Colon Cancer |
| Repeat Same Dose | 13 | 1 of 13 | 8% | Breast Cancer |
| Desensitizing Dose followed by Two Higher Doses | 22 (19 evaluated) | 3 of 19 | 16% | Mesothelioma Melanoma Colon Cancer |
| Total | 52 (49 evaluated) | 5 of 49 | 10% | As noted above |

These cases are summarized below:

(A) Tumor Regression of a Palpable Colon Metastasis

A 68 year old woman with colon carcinoma has a palpable abdominal tumor among her widespread metastases. After a single IV treatment with PPMK107 at 12 billion PFU/m$^2$, this patient experienced a 91% regression of this single abdominal wall tumor over the course of two weeks (Table 20 below). Measurements of the tumor one day after dosing (3.75×3 cm) were similar to the baseline measurements of 4×3 cm. However, by day 7 post dosing, the tumor had decreased in size to 2×2 cm and continued to decrease in size to 1.5×1.5 cm by day 14 after PPMK107 dosing. Previous to PPMK107 treatment, this tumor mass had been rapidly growing with a 1065% increase in tumor volume in the two weeks before PPMK107 dosing. This patient was taken off study because of increased growth of the tumor elsewhere.

TABLE 20

Size of Palpable Abdominal Wall Tumor in Patient #123 (68 year old Female with Metastatic Colon Carcinoma) After a Single IV PPMK107 Dose or 12 Billion PFU/m$^2$.

| Date | Time After Dosing | Tumor Dimensions (L × W, cm$^3$) | Tumor Volume (0.5 × L × W × W, cm$^3$) | % Reduction in Tumor Volume |
|---|---|---|---|---|
| Jul. 23, 1998 | Day 0 | 4 × 3 | 18. | — |
| Jul. 24, 1998 | Day 1 | 3.75 × 3 | 16.9 | 6% |
| Jul. 30, 1998 | Day 7 | 2 × 2 | 4.0 | 78% |
| Aug. 6, 1998 | Day 14 | 1.5 × 1.5 | 1.7 | 91% |

B) Regression of a Chest Wall Tumor in a Woman with Breast Cancer

A 58 year old woman with breast carcinoma had a palpable chest wall mass apparent to visual inspection. During her second course of PPMK107 treatment with three doses of 5.9 billion PFU/m$^2$, her chest wall tumor mass by visual and palpable inspection decreased ~90%. This patient was taken off study after her third course of therapy because of increased growth of the cancer elsewhere.

C) Regression of Abdominal Tumors in a Patient with Peritoneal Mesothelioma

A 46 year old man with peritoneal mesothelioma has three large (8 to 10 cm) masses regress 50%, 42% and 10%, respectively, after his first course of PPMK107 treatment consisting of a desensitizing dose of 12 billion PFU/m$^2$ followed by two doses at 48 billion PFU/m2. His other remaining large tumor mass (9.8 cm in size) remained stable after this first course of treatment. This patient is currently still on study. His most recent CT scan still indicated significant tumor regression of at least 30 to 36% from baseline for two of his metastases and overall disease stabilization.

D) Regression of Metastatic Tumors in a Patient with Melanoma

A 57 year old man with melanoma had two tumor masses completely regress after his first course of PPMK107 treatment consisting of a desensitizing does of 12 billion PFU/m$^2$ followed by two doses at 48 billion PFU/m2. The two tumors which disappeared after PPMK107 treatment were a palpable groin mass of 1 cm in size and a small lung metastasis. This patient was taken off study because of increased growth of the tumor elsewhere.

E) Continued Regression of a Liver Metastasis in a Patient with Colon Cancer

A liver metastasis in the caudate lobe of a 79 year old man with colon carcinoma regressed 59% after his first course of PPMK107 and regressed 97% after his second course. Treatment consisting of a desensitizing dose of 12 billion PFU/m$^2$ followed by two doses at 72 billion PFU/m$^2$. At baseline before treatment, this tumor measured 3×3 cm (tumor volume of 13.5 cm$^3$ based on a ½×L×W$^2$ fomula). After his first course of PPMK107, it decreased 59% to 2.8×2 cm (tumor volume of 5.6 cm$^3$). Three weeks after his second course of PPMK107, this same tumor mass in the caudate lobe was reported as measuring 3×0.5 cm (tumor volume of 0.38 cm$^3$), a 97% decrease from baseline.

Stabilization of Cancer

Twenty one other patients, all of whom previously has tumor progression with conventional cancer therapies, have experienced benefit in the form of stabilization of their advanced cancer after PPMK107 dosing. These patients with stable disease represent those with diverse types of cancer including renal cancer, pancreatic cancer, breast cancer, bladder cancer, cholangiocarcinoma of the gallbladder, and lung cancer. Included among these cases are the following: (1) seven month stable disease in a patient with renal cancer; (2) seven month stable disease in a patient with lung cancer; (3) five month stable disease in a patient with pancreatic cancer; (4) five month stable disease in another patient with pancreatic cancer; (5) ongoing 3 month stable disease in a patient with renal cancer; (6) ongoing 2 month stable disease in a patient with cholangiocarcinoma of the gallbladder.

Reduction in Pain Medication

One patient at the single dose 5.9 billion PFU/m$^2$ dose level has benefited from PPMK107 treatment in the form of symptomatic relief of cancer pain as denoted by a reduction in narcotic pain medication.

Desensitization

In the desensitizing regimen, a clear desensitizing effect from the first dose (at 12 billion PFU/m$^2$) is seen on subsequent doses within that same week. In general, the reported side effects from second and third doses have been of lower incidence and milder, even when these doses are 2 to 8 times higher (at between 24 to 96 billion PFU/m$^2$) than the first dose. For example, while fever has been reported in 68% of patients (including 9% with a grade 3 fever spike) after the first dose, it was only reported in 32% of patients (none with grade 3 fever) after the second dose and was reported in only 5% of patients after the third dose. As another example, chills were seen in 50% of the patients after the first dose, 18% of the patients after the second dose, and in only 14% of the patients after the third dose.

As another example, in the repeat same dose study, the first 4 patients in this multidose treatment regimen (three doses of 5.9 billion PFU/m2 per week for one week) had fever after the first dose in spite of receiving prophylactic antipyretic treatment with acetaminophen and ibuprofen. The majority of these patients had no fever after receiving the second and third doses, even in cases in which they did not receive antipyretics. There is therefore strong evidence that administration of the first dose in the three times per week schedule reduces the toxicity for the second and third doses.

Dosing Through Neutralizing Antibodies in Serum

Using the dose range in this phase I study ($\geq$5.9 billion PFU/m$^2$), there is also clear indication that one can effectively deliver virus to patients even if they have generated neutralizing antibodies. A 72 year old woman with pancreatic cancer at the 12 billion PFU/m$^2$ single dose level has had stable disease for 2 months since beginning PPMK107 treatment. A second course (consisting of a single IV dose of PPMK107) was administered one month after the first dose when the patient has produced neutralizing antibodies in her serum. Seven days after this second course, her urine was positive for PPMK107 at a titer of at least 40 PFU per mL.

Additional evidence indicating that antitumor efficacy is achievable using the dose ranges in this trial ($\geq$5.9 billion PFU/m$^2$) in spite of the presence of neutralizing antibody is taken from a 58 year old woman with breast cancer that had spread to her chest wall. As noted in the section discussing tumor regression, her chest wall tumor mass regressed ~90% during her second course of therapy. This effect occurred between weeks 5 to 6 after her initial course, at a time in which her antibody had a titer of 1:256 (at the beginning of week 5) and rose to >1:2560 (by the beginning of week 6). Further evidence that virus can be delivered effectively to this patient in spite of the presence of neutralizing antibody is indicated by the positive urine sample (20 to 40 PFU/ml) seen at the end of week 5 (when her baseline urine at the beginning of week 5 had been negative).

These results indicate that the neutralizing antibodies to PPMK107 in these patients' serum was not able to completely inhibit the virus nor the virus's antitumor efficacy with a second treatment course.

EXAMPLE 21

Summary of Cytotoxicity Assay Results with Newcastle Disease Virus PPNJROAKIN

Human tumor cells and normal cells were grown to approximately 80% confluence in 24 well tissue culture dishes. Growth medium was remove and PPNJROAKIN, a plaque purified clone of the mesogenic Newcastle disease virus strain New Jersey Roakin-1946, was added in 10 fold dilutions ranging from 10$^7$ plaque forming units (PFU)/well to 1 PFU/well. Controls wells with no virus added were included on each plate. Virus was adsrobed for 90 minutes on a rocking platform at 37° C. At the end of the incubation period, the viral dilutions were removed and replaced by 1 ml of growth medium. Plates were then incubated for 5 days at 37° C. in 5% CO2. Cytotoxicity was quantified by using a colorimetric MTT (2-[4,5-dimethylthiazol-2-yl]-2,5-diphenyl tetrazolium bromide) assay (Cell Titer 96, catalog #G4000, Promega Corporation, Madison Wis. 53711) monitored at 570 nm, that detects mitochondrial enzyme activity (Mosman, T., 1983, J. Immunol. Methods 65:55). The viability in the virus treated wells was expressed as a percent of the activity in untreated control wells. The data was plotted graphically as PFU/well vs. viability as a percent of control. The IC50 was calculated as the amount of virus in PFU/well causing a 50% reduction in the amount of viable cells.

TABLE 21

Summary of Cytotoxicity Assay Results with PPNJROAKIN.

| Cell Type | Cell Line | IC$_{50}$ (PFU/well) |
| --- | --- | --- |
| Fibrosarcoma | HT1080 | 13.8 |
| Head and Neck Carcinoma | KB | 2.4 |
| Normal Fibroblast | CCD922sk | $1.2 \times 10^4$ |

These results show that PPNJROAKIN demonstrates tumor-selective killing of at least two different human tumor cells (HT1080 and KB) relative to normal skin fibroblasts. The IC50 values for the two tumor cell lines are between 800 and 5000-fold lower than that for normal cells.

EXAMPLE 22

Summary of Cytotoxicity Assay Results with Newcastle Disease Virus PPCONN70726

Human tumor cells and normal cells were grown to approximately 80% confluence in 24 well tissue culture dishes. Growth medium was removed and PPCONN70726, a plaque purified clone of the mesogenic Newcastle disease virus strain Connecticut 70726-1946, was added in 10 fold dilutions ranging from 10$^7$ plaque forming units (PFU)/well to 1 PFU/well. Controls wells with no virus added were included on each plate. Virus was absorbed for 90 minutes on a rocking platform at 37° C. At the end of the incubation period, the viral dilutions were removed and replaced by 1 ml of growth medium. Plates were then incubated for 5 days at 37° C. in 5% CO2. Cytotoxicity was quantified by using a colorimetric MTT (2-[4,5-dimethylthiazol-2-yl]-2,5-diphenyl tetrazolium bromide) assay (Cell Titer 96, catalog #G4000, Promega Corporation, Madisoin Wis. 53711) monitored at 570 nm, that detects mitochondrial enzyme activity (Mosman, T., 1983, J. Immunol. Methods 65:55). The viability in the virus treated wells was expressed as a percent of the activity in untreated control wells. The data was plotted graphically as PFU/well vs. viability as a percent of control. The IC50 was calculated as the amount of virus in PFU/well causing a 50% reduction in the amount of viable cells.

TABLE 22

Summary of Cytotoxicity Assay Results with PPCONN70726.

| Cell Type | Cell Line | $IC_{50}$ (PFU/well) |
|---|---|---|
| Head and Neck Carcinoma | KB | 18.1 |
| Glioblastoma | U87MG | 12.7 |
| Glioblastoma | U373MG | 879 |
| Normal Fibroblast | CCD922sk | $7.3 \times 10^4$ |

These results show that PPCONN70726 demonstrates tumor-selective killing of at least three different human tumor cells (KB, U87MG, and U373MG) relative to normal skin fibroblasts. The IC50 values for the two tumor cell lines are between 80 and 5000-fold lower than that for normal cells.

EXAMPLE 23

Intratumoral Treatment of HT1080 Fibrosarcoma Xenografts in Athymic Mice Using PPMK107, PPNJROAKIN, or PPCONN70726

In this experiment, athymic mice (female, NCR nu/nu, 5 to 6 weeks old) received a subcutaneous injection of $10^7$ HT1080 tumor cells. Four days later when tumors reached a size range of 6 to 8.5 mm, mice were treated intratumoarlly with saline, PPMK107 (at $1\times10^8$ PFU), PPNJROAKIN (at $1\times10^8$ PFU), or PPCONN70726 (at $1\times10^8$ PFU). As shown in Table 23 below, tumor regression was noted in mice treated with these three viruses (PPMK107, PPNJROAKIN, and PPCONN70726). After PPMK107 treatment of 12 mice, four experienced complete tumor regression and six experienced partial regression. After PPNJROAKIN treatment of 12 mice, one mouse experienced complete tumor regression and two experienced partial regression. After PPCONN70726 treatment of 12 mice, three experienced complete tumor regression and two experienced partial regression. No tumor regression was noted in any of the animals treated with saline.

TABLE 23

Regression of HT1080 Fibrosarcoma Tumors in Athymic Mice After Treatment with One of Three Viruses (PPMK107, PPNJROAKIN and PPCONN70726) Each at a Dose of $1 \times 10^8$ PFU.

| | | Regression | | |
|---|---|---|---|---|
| Treatment | # of Mice | Partial (PR) | Complete (CR) | PR + CR (%) |
| PPMX107 | 12 | 6 | 4 | 10 (83%) |
| PPNJROAKIN | 12 | 2 | 1 | 3 (25%) |
| PPCONN70726 | 12 | 2 | 3 | 5 (42%) |
| Saline | 11 | 0 | 0 | 0 (0%) |

EXAMPLE 24

Effects of PPMK107, PPNJROAKIN, PPCONN70726 After Intracerebral Injection in Immunodeficient Athymic (nu/nu) and Immunocompetent Heterozygote (nu/+) Mice Fifty-six athymic mice (nu/nu) and 56 immunocompetent heteroxygote (nu/+) mice were given stereotaxic intracerebral injections with either saline, PPMK107, PPNJROAKIN, or PPCONN70726. Eight additional mice of each type were used as untreated controls. Viruses were used at one of two dose levels ($2\times10^4$ or $3.5\times10^6$ PFU/mouse). As shown in Table 24 below, all of the heterozygote nu/+ mice treated with each of the three viruses at the two dose levels survived through day 39 with the exception of one mouse at the lower PPCONN70726 dose level that was euthanized for non-neurological symptoms. Athymic nu/nu animals treated with either PPMK107 or PPCONN70726 had significantly less survival than the heterozygotes. This was especially true for the highest PPMK107 or PPCONN70726 virus dose of $3.5\times10^6$ PFU/mouse where only 13% (1 of 8) of the athymic animals in each virus group survived through day 39. In contrast, there was 75% survival of the PPNJROAKIN-treated athymic mice at this same dose level ($3.5\times10^6$ PFU/mouse). These data indicate that PPNJROAKIN is better tolerated in the brains of athymic mice than the other two virus strains.

TABLE 24

Survival of Mice Following Intracerebral Injection of PPMK107, PPCONN70726, and PPNJROAKIN

| | Intracranial Injection | # of Mice | % Survival at Day 39 |
|---|---|---|---|
| nu/+ | Untreated | 8 | 100 |
| nu/+ | Saline | 8 | 100 |
| nu/+ | PPMK107, 2E+04 | 8 | 100 |
| nu/+ | PPMK107, 3.5E+06 | 8 | 100 |
| nu/+ | PPCONN70726, 2E+04 | 8 | 88* |
| nu/+ | PPCONN70726, 3.5E+06 | 8 | 100 |
| nu/+ | PPNJROAKIN, 2E+04 | 8 | 100 |
| nu/+ | PPNJROAKIN, 3.5E+06 | 8 | 100 |
| nu/nu | Untreated | 8 | 100 |
| nu/nu | Saline | 8 | 100 |
| nu/nu | PPMK107, 2E+04 | 8 | 75 |
| nu/nu | PPMK107, 3.5E+06 | 8 | 13 |
| nu/nu | PPCONN70726, 2E+04 | 8 | 75 |
| nu/nu | PPCONN70726, 3.5E+06 | 8 | 13 |
| nu/nu | PPNJROAKIN, 2E+04 | 8 | 100 |
| nu/nu | PPNJROAKIN, 3.5E+06 | 8 | 75 |

*The one non-surviving mouse in this treatment group was euthanized for non-neurological symptoms.

EXAMPLE 25

Summary of Cytotoxicity Assay Results with Sindbis Virus PPSINDBIS-Ar339

Human tumor cells and normal cells were grown to approximately 80% confluence in 24 well tissue culture dishes. Growth medium was removed and PPSINDBIS-Ar339, a plaque purified clone of Sindbis Ar-339 was added in 10 fold dilutions ranging from $10^7$ plaque forming units (PFU)/well to 1 PFU/well. Control wells with no virus added were included on each plate. Virus was adsorbed for 90 minutes on a rocking platform at 37° C. At the end of the incubation period, the viral dilutions were removed and replaced by 1 ml of growth medium. Plates were then incubated for 5 days at 37° C. in 5% CO2. Cytotoxicity was quantified by using a colorimetric MTT (2-[4,5-dimethylthiazol-2-yl]-2,5-diphenyl tetrazolium bromide) assay (Cell Titer 96, catalog #G4000, Promega Corporation, Madison Wis. 53711) monitored at 570 nm, that detects mitochondrial enzyme activity (Mosman, T., 1983, J. Immunol. Methods 65:55). The viability in the virus treated wells was expressed as a percent of the activity in untreated control wells. The data was plotted graphically as PFU/well vs. viability as a percent of control. The IC50 was calculated as the amount of virus in PFU/well causing a 50% reduction in the amount of viable cells.

TABLE 25

Summary of Cytotoxicity Assay Results with PPSINDBIS-Ar339

| Cell Type | Cell Line | $IC_{50}$ (PFU/well) |
|---|---|---|
| Pancreatic Carcinoma | Panc-1* | 69 |
| Colorectal Carcinoma | SW620* | 13 |
| Colorectal Carcinoma | SW1463 | $1.8 \times 10^5$ |
| Non-small cell Lung carcinoma | A427 | $>1 \times 10^6$ |
| Non-small cell Lung carcinoma | A549 | $5.2 \times 10^4$ |
| Renal carcinoma | A498 | $2.4 \times 10^4$ |
| Renal carcinoma | Caki-1 | $3.4 \times 10^4$ |
| Fibrosarcoma | HT1080 | $7.4 \times 10^5$ |
| Normal Keratinocyte | NHEK | $2.0 \times 10^5$ |
| Normal Fibroblast | CCD922sk | $1.6 \times 10^5$ |

*Cells known to overexpress the mRNA for the high affinity laminin receptor.

The cellular receptor for Sindbis virus on mammalian cells is the high affinity laminin receptor, that is expressed mainly on cells of epithelial lineage, but is often overexpressed in many metastatic cancer cells like the Panc-1 pancreatic carcinoma line, and the SW620 colon adenocarcinoma cell line (Campo et al., (1992) *Am. J. Pathol.* 141, 1073-1083; Yow et al., (1988) *Proc. Natl Acad Sci,* 85, 6394-6398). In contrast, the rectal adenocarcinoma cell line SW1463 is known to express very low levels of high affinity laminin receptor mRNA (Yow et al., (1988) *Proc. Natl Acad Sci,* 85, 6394-6398), and is more than 4 order of magnitude more resistant to killing by PPSINDBIS-Ar339 than SW620 cells. These results demonstrate that cells that are tumorigenic and express high levels of the high affinity laminin receptor are more sensitive to killing by Sindbis Clone PPSINDBIS-Ar339 than other tumor or normal cells.

EXAMPLE 26

VSV Killing of Tumorigenic and Non-Tumorigenic Cells in the Presence of Interferon In 96 well plates, tumorigenic KB and HT1080 cells ($3 \times 10^4$ cells per well) and non-tumorigenic WISH cells ($2.5 \times 10^4$ cells per well) were seeded in the presence of serially diluted interferon-α ranging from 2800 to 22 Units/ml and allowed to incubate for 24 hours at 37° C. The cells were then infected with vesicular stomatitis virus (VSV, Indiana strain) at an moi of 10. Controls were included for cells without interferon, and cells without interferon or virus. The cells were incubated at 37° for 24 hours. Cytotoxicity was quantified by using a colorimetric MTT (2-[4,5-dimetylthiazol-2-yl]-2,5-diphenyl tetrazolium bromide) assay (Cell Titer 96, catalog #G4000, Promega Corporation, Madison Wis. 53711) monitored at 570 nm, that detects mitochondrial enzyme activity (Mosman, T., 1983, J. Immunol. Methods 65:55). The visibility in the virus treated wells was expressed as a percent of the activity in control wells not receiving virus.

TABLE 26

Comparison of the Cell Killing Activity of VSV in Cells Treated with Exogenous Interferon.

| | Percent Viable Cells | | |
|---|---|---|---|
| | WISH | HT1080 | KB |
| 0 U/ml IFN | 0 | 0 | 0 |
| 100 U/ml IFN | 50 | 6 | 0 |
| 1000 U/ml IFN | 95 | 20 | 12 |

These results demonstrate that VSV is able to selectively kill tumor cells deficient in interferon responsiveness (see Example 27). WISH cells (human amnion cells) are a well established cell line for the use in interferon bioassays because of their ability to respond efficiently to interferons.

EXAMPLE 27

Interferon Responsiveness in Cells Sensitive or Resistant to Killing by PPMK107

Figure 5:
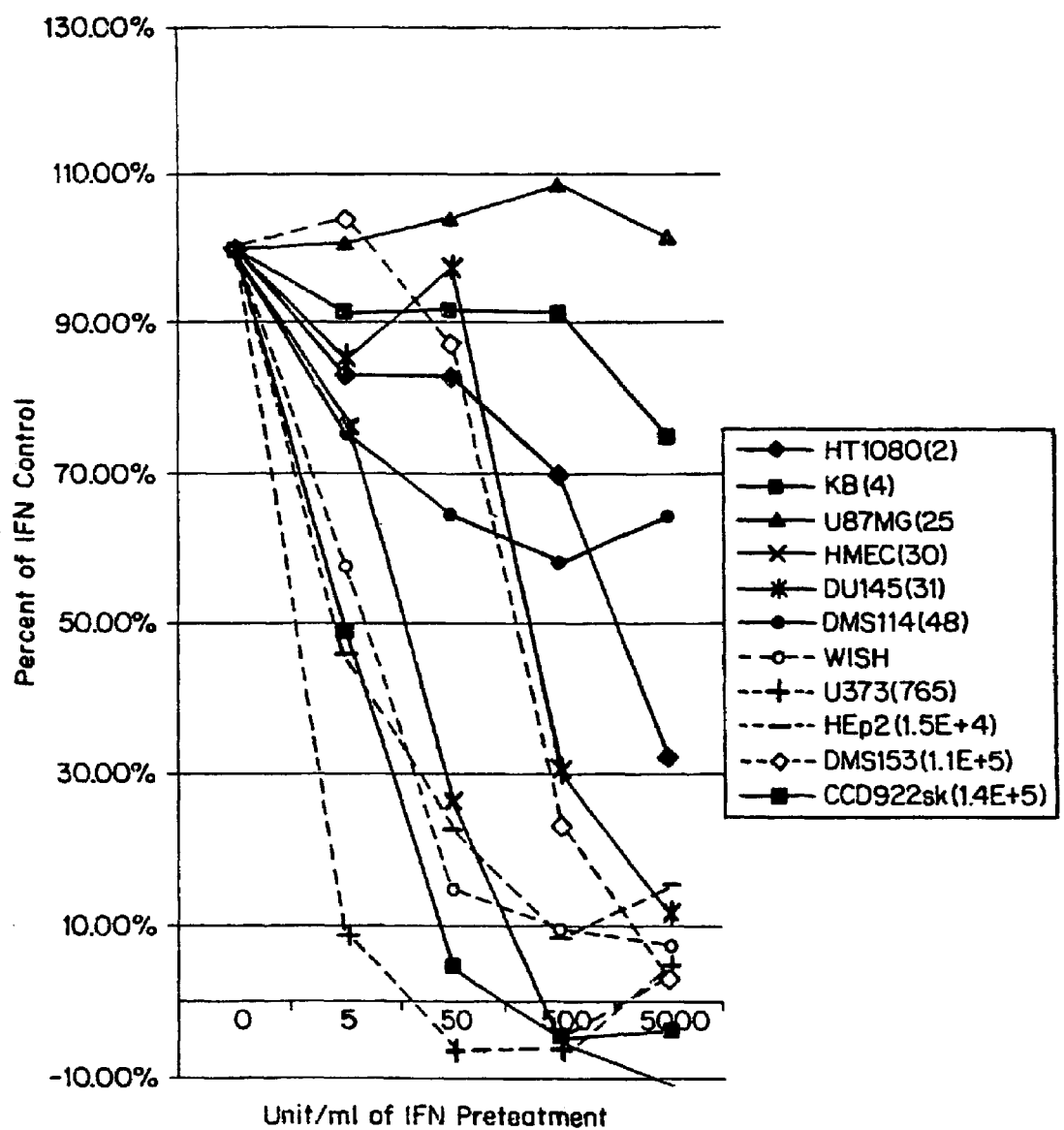
FIG. 5 shows the interferon responsiveness of a number of human tumor and normal cell lines.

Individual cell lines were grown to near confluence in 96 well microtiter plates and treated with between 5 and 5000 U/ml of IFNαA for 24 hours. The cultures were then infected with PPMK107 at an moi of 1.0 and cultured for an additional 24 hours. Following chemical fixation, the amount of viral expression was quantified by immunohistochemistry using a soluble indicator dye. The amount of virus growth is represented as the percent of P antigen expressed relative to control cells untreated with interferon (FIG. 5). In this assay, interferon responsive cells manifest at least a 50% decrease in the viral antigen in response to interferon.

The results of this experiment show a strong correlation between the resistance of the cell line to the antiviral effects of exogenous interferon and the relative sensitivity of the cell to killing by PPMK107 (indicated by the IC50 value shown in parentheses next to the cell line name in the graph legend, see FIG. 5). For example, following pretreatment with 5 U/ml of interferon, 6 to 7 (86%) cell lines nonresponsive to interferon are sensitive to killing by PPMK107; when pretreated with 500 U/ml of interferon, all (4 of 4) of the nonresponsive cell lines are sensitive to killing by PPMK107.

The data above also present an example of a screening assay to identify candidate cells that are likely to be sensitive to killing by PPMK107 or other interferon-sensitive viruses. For example, infected cells expressing significant (e.g., more than 50% of controls) viral antigen following pretreatment with exogenous interferon would be considered interferon deficient and thereby sensitive to viral oncolysis.

EXAMPLE 28

Use of a Desensitizing Intravenous Dose of PPMK107 to Reduce the Lethality of a Subsequent Intraperitoneal Dose of PPMK107

Mice were injected intravenously on day 0 with either saline or a desensitizing dose of PPMK107 ($3 \times 10^8$ PFU/mouse). Two days later each set of mice were further subdivided into groups for intraperitoneal dosing with saline or PPMK107 (at doses of $1 \times 10^9$, $2.5 \times 10^9$, $5 \times 10^9$, and $1 \times 10^{10}$ PFU/mouse). As shown in Table 27 below, when saline was used to pretreat the mice, deaths were recorded in the mice subsequently dosed with $2.5 \times 10^9$, $5 \times 10^9$, and $1 \times 10^{10}$ PFU.

The doses of $2.5\times10^9$, $5\times10^9$ and $1\times10^{10}$ PFU were 25%, 50% and 100% lethal, respectively, to the mice pretreated with saline. In contrast, using an IV desensitizing dose, no deaths were seen in the $2.5\times10^9$ and $5\times10^9$ PFU groups and only a 38% mortality was seen in the $1\times10^{10}$ PFU group of mice. These data indicate that PPMK107 given by the intravenous route can be used to desensitize the toxicity of subsequent dosing of another route (namely in this example, the intraperitoneal route) with this same agent. Furthermore, the maximal tolerated intraperitoneal dose of PPMK107 can be raised by approximately 5-fold when using this virus as a desensitizing agent.

TABLE 27

Use of a Desensitizing Intravenous Dose of PPMK107 to Reduce the Lethality of a Subsequent Intraperitoneal Dose of PPMK107.

| Group | IV Injection on Day 0 | IP Dose on Day 2 | # of Mice | # of Deaths | % Lethality |
|---|---|---|---|---|---|
| 1 | Saline | Saline | 8 | 0 | 0 |
| 2 | Saline | PPMK107, 1.0E+09 | 8 | 0 | 0 |
| 3 | Saline | PPMK107, 2.5E+09 | 8 | 2 | 25 |
| 4 | Saline | PPMK107, 5.0E+09 | 8 | 4 | 50 |
| 5 | Saline | PPMK107, 1.0E+10 | 8 | 8 | 100 |
| 6 | PPMK107, 3E+08 | Saline | 8 | 0 | 0 |
| 7 | PPMK107, 3E+08 | PPMK107, 1.0E+09 | 8 | 0 | 0 |
| 8 | PPMK107, 3E+08 | PPMl07, 2.5E+09 | 8 | 0 | 0 |
| 9 | PPMK107, 3E+08 | PPMK107, 5.0E+09 | 8 | 0 | 0 |
| 10 | PPMK107, 3E+08 | PPMK107, 1.0E+10 | 8 | 3 | 38 |

EXAMPLE 29

Use of a Desensitizing Intravenous Dose of PPMK107 to Increase the Antitumor Efficacy a Subsequent Intraperitoneal Dose of PPMK107

In this example, athymic mice with visually apparent ascites tumors derived from the ES-2 human ovarian carcinoma cell line were treated with intraperitoneally with PPMK107 either with our without prior intravenous desensitization two days previously with $3\times10^8$ PFU/mouse. As shown in Table 28, control mice treated intraperitoneally with saline rapidly died from ascites tumors with only 8% surviving by day 9 post treatment. Administering the maximum tolerated dose of PPMK107 intraperitoneally increased the survival percentage to 46% at day 9. Using IV desensitization, higher IP doses of PPMK107 such as $2.5\times10^9$ and $5.0\times10^9$ PFU can be tolerated and lead to almost a doubling of survival rate (83% and 79%, respectively) when compared to that achievable with the highest dose ($1.0\times10^9$ PFU) without desensitization.

TABLE 28

Survival of Mice with ES-2 Human Ovarian Carcinoma Ascites Tumors after Intraperitoneal PPMK107 Treatment

| IP Treatment Group (PFU/moue) | Survival (Day 9) Without IV Desensitization | Survival (Day 9) With IV Desensitization |
|---|---|---|
| Saline | 2 out of 24 (8%) | 3 out of 24 (13%) |
| 1.0 E+09 | 11 out of 24 (46%) | 11 out of 24 (46%) |
| 2.5 E+09 α | Dose Above MTD | 20 out of 24 (83%) |
| 5.0 E+09 α | Dose Above MTD | 19 out of 24 (79%) |

α-Dose above MTD without desensitization but below MTD with desensitization.

EXAMPLE 30

Anti-Recombinant Murine TNF-alpha Antiserum Blocks IV Lethality of PPMK107 in Mice In this example, groups of 16 female C57BL/6 mice were dosed intravenously with $5.0\times10^9$ PFU of PPMK107. Five hours previously different groups of 16 mice received either anti-recombinant murine TNF-alpha antiserum (100 ul from rabbits diluted 1:10 with saline), the equivalent amount of control rabbit serum or saline. As shown in Table 29 below, the lethality of PPMK107 at this dose is completed blocked using the rabbit antiserum against murine TNF-alpha.

TABLE 29

Mortality of Mice Pretreated with Anti-Recombinant Murine TNF-Alpha Antiserum Before IV Dosing with 5.0E+09 of PPMK107.

| PV701 Dose | Pretreatment | Mortality |
|---|---|---|
| 2.5 E+09 PFU/mouse | Saline | 5 out of 16 |
| | Control Rabbit Serum | 7 out of 16 |
| | Anti-rTNFalpha Antiserum | 0 out of 16-α |

α-Mortality significantly different from saline and rabbit serum control treatment groups ($P < 0.05$, Fisher's Exact Test).

EXAMPLE 31

Purification of Clonal Viruses

A number of clonal RNA viruses were purified by either ultracentrifugation of the virus without pelleting or by sequential tangential flow filtration. For purification by one of the following methods:

Method 1: As in Method A of Example 15.
Method 2: As in Method D of Example 15.
Method 3: Vero cells at approximately 70% confluence were infected at an moi of 0.01 and incubated at 37° C. for 18 hours. The flasks containing the infected cells were frozen at −70° C. The cell were thawed at room temperature and then maintained on ice until harvest. For harvest, the cells were scraped into the media present during the infection and clarified at 1750× g for 30 minutes at 4° C. The clarified supernatants were pooled and layered over a 20%/55% discontinuous gradient and centrifuged at approximately 100,000×g for 30 minutes. The purified virus was harvested from the sucrose 20%/55% interface and dialyzed against calcium- and magnesium-free PBS to remove the sucrose.

The activity of the virus preparations was determined by the plaque assay method using HT1080 cells for Newcastle disease virus and Vero cells for Vesicular stomatitis strains.

The protein content of the virus preparation was determined using the NanoOrange Protein Quantification Kit (Molecular Probes, Inc., Eugene, Oreg.) with bovine serum albumin as the protein standard.

TABLE 30

Specific Activity of a Number of Clonal RNA Viruses Purified by Ultracentrifugation without Pelleting or Tangential Flow Filtration.

| Virus | Virus Clone | Purification Method | Specific Activity (PFU/mg protein) |
|---|---|---|---|
| Newcastle disease-MK107 strain | PPMK107 | 1 | 1.3E+11 |
| Newcastle disease-MK107 strain | PPMK107 | 2 | 1.0E+11 |
| Newcastle disease-Roakin strain | PPNJROAKIN | 1 | 1.0E+11 |
| Newcastle disease-ConnH strain | PPCONN70726 | 1 | 2.1E+10 |
| Vesicular Stomatitis-Indiana strain | PPVSV | 3 | 4.5E+9 |

These results demonstrate the ability to purify different clonal RNA viruses to high specific activity using the methods described in this invention.

EXAMPLE 32

Sindbis Virus PPSINDBIS-Ar339 Causes Tumor Inhibition in Athymic Mice with Human Tumor Cell Xenografts Athymic mice were injected subcutaneously with 10 million SW620 human adenocarcinoma tumor cells. Five days later the tumors (average size=78 mm$^3$) were treated with a single injection of PPSINDBIS-Ar339 (10 mice, 5×10$^6$ PFU) or saline (9 mice). Tumor size and mouse weight were measured twice per week until study termination. By the twelfth day after treatment the average tumor size of the saline treated mice had increased by an average of 896% (from 71.3 mm$^3$ to 639.1 mm$^3$).

TABLE 31

Intratumoral treatment of SW620
Colon Adenocarcinoma Human Xenografts with PPSINDBIS-Ar339.

| Time Post Treatment | Tumor Growth Inhibition[a] |
|---|---|
| 5 days | 89% |
| 9 days | 90% |
| 12 days | 87% |

[a]tumor growth inhibition = $\dfrac{\% \text{ increase control group} - \% \text{ increase Tx group}}{\% \text{ increase control group}} \times 100$ These data show that a single injection of PPSINDBIS-Ar339 results in significant tumor growth inhibition compared to treatment with saline. Treatment with PPSINDBIS-Ar339 was also well tolerated by the mice as evidenced by the absence of weight loss in either the saline or virus treated groups.

EXAMPLE 33

Figure 6:
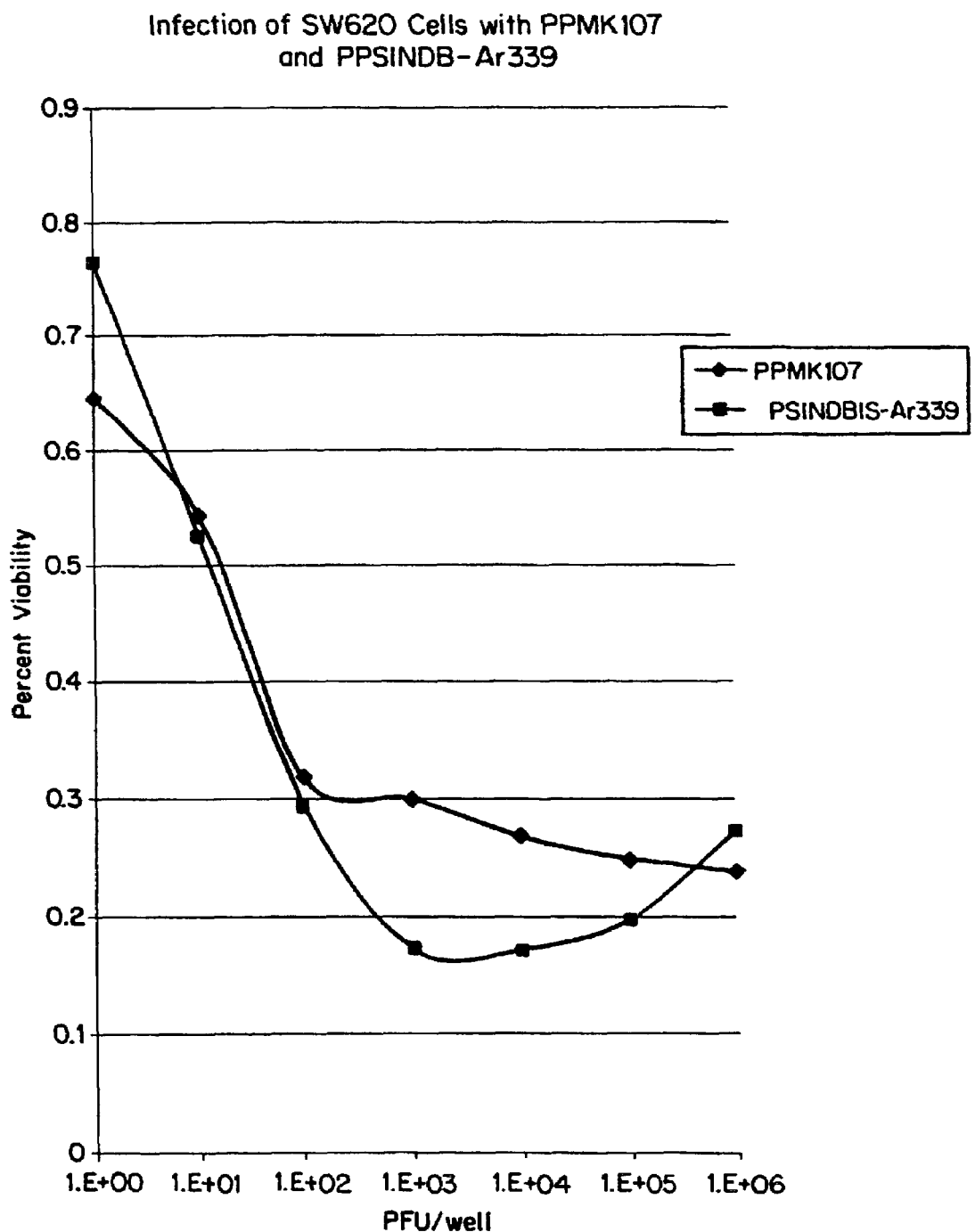
FIG. 6 shows the dose response of the SW620 tumor cell line to infection with PPMK107 and PPSINDBIS-Ar339.

Viruses Belonging to Unrelated Families Have Similar Activity on Human Tumor Cell Lines Cytotoxicity assays were performed with the SW620 adenocarcinoma cell line and PPMK107 (Paramyxovirus family) or PPSINDBIS-Ar339 (Togavirus family) as described in Examples 1 and 25 (see FIG. 6). These two unrelated viruses use distinct receptors to enter the host cell and replicate by mechanisms unique to each virus. Nevertheless, the response of the SW620 cell line to infection by these two viruses is remarkably similar indicating that the mechanisms of tumor cell killing by these viruses share common elements.

EXAMPLE 34

Use of PPMK107 in Combination with Chemotherapy for the Systemic Treatment of Human Tumor Xenografts in Athymic Mice Athymic mice were injected subcutaneously with 10 million human HT1080 fibrosarcoma cells. After tumors reached a size range from between 5 and 7 mm, mice were randomized into treatment groups. Mice received intraperitoneal injections saline vehicle on treatment days 0, 2 and 4. PPMK107 at a dose of 2×10$^7$ PFU or saline vehicle was administered by intravenous injection on treatment day 2 only, one hour after the intraperitoneal injection. Carboplatin (carbo) at a dose of 160 mg/kg was administered by intraperitoneal injection on treatment day 0, 2, or 4 as indicated. The percent of each group with complete regression (CR) and partial regression (PR) is shown. Each treatment group had 9 tumor-bearing mice.

TABLE 32

PPMK107 in Combination with Carboplatin
for the Systemic Treatment of Subcutaneous Human HT1080
Fibrosarcoma Xenografts in Athymic Mice.

| Treatment | CR + PR (%) |
|---|---|
| Saline, days 0, 2 and 4 | 0 |
| PPMK107, day 2 | 44 |
| Carbo, day 0 | 0 |
| Carbo, day 2 | 11 |
| Carbo, day 3 | 11 |
| PPMK107, day 2 Carbo, day 0 | 67 |
| PPMK107, day 2 Carbo, day 2 | 78 |
| PPMK107, day 2 Carbo, day 4 | 55 |

These results in Table 32 indicate that subcutaneous HT1080 tumors are responsive to IV treatment with PPMK107 and that addition of carboplatin two days before, the same day, or two days after PPMK107 treatment resulted in a higher percentage of tumor regression (CR+PR) than either PPMK107 alone or carboplatin alone.

EXAMPLE 35

Second Experiment on the Use of PPMK107 in Combination with Carboplatin for the Systemic Treatment of Human HT1080 Tumor Xenografts in Athymic Mice Athymic mice were injected subcutaneously with 10 million human HT1080 fibrosarcoma cells as in Example 34. Mice received intraperitoneal injections carboplatin (carbo) at a dose of 80 mg/kg or 120 mg/kg or saline vehicle on treatment day 0 followed by intravenous injection of PPMK107 (at $6\times10^6$ or $2\times10^7$ PFU) on treatment day 2. The percent of each group with complete regression (CR) and partial regression (PR) is shown. Each treatment group had 9 tumor-bearing mice.

TABLE 33

PPMK107 in Combination with Carboplatin for the Systemic Treatment of Subcutaneous Human HT1080 Fibrosarcoma Xenografts in Athymic Mice.

| Treatment | Dose | CR + PR (%) |
|---|---|---|
| Saline | | 0 |
| PPMK107 | 6E+06 PFU | 22 |
| PPMK107 | 2E+07 PFU | 56 |
| Carbo | 80 mg/kg | 33 |
| Carbo | 120 mg/kg | 22 |
| PPMK107 Carbo | 6E+06 PFU 80 mg/kg | 78 |
| PPMK107 Carbo | 6E+06 PFU 120 mg/kg | 44 |
| PPMK107 Carbo | 2E+07 PFU 80 mg/kg | 67 |
| PPMK107 Carbo | 2E+07 PFU 120 mg/kg | 100 |

These results in Table 33 indicate that subcutaneous HT1080 tumors are responsive to IV treatment with PPMK107 at each dose level and that addition of carboplatin at either dose level two days before PPMK107 treatment resulted in a higher percentage of tumor regression (CR+PR) than either PPMK107 alone or carboplatin alone.

EXAMPLE 36

Third Experiment on the Use of PPMK107 in Combination with Carboplatin for the Systemic Treatment of Human HT1080 Tumor Xenografts in Athymic Mice Athymic mice were injected subcutaneously with 10 million human HT1080 fibrosarcoma cells as in Example 34. Mice received intraperitoneal injections carboplatin (carbo) at a dose of 60 mg/kb or saline vehicle on treatment day 0 followed by intravenous injection of PPMK107 (at $6\times10^6$ PFU) on treatment day 2. The percent of each group with complete regression (CR) and partial regression (PR) is shown. Each treatment group had 9 tumor-bearing mice except for the carboplatin only group which had 8 mice.

TABLE 34

PPMK107 in Combination with Carboplatin for the Systemic Treatment of Subcutaneous Human HT1080 Fibrosarcoma Xenografts in Athymic Mice.

| Treatment | CR + PR (%) |
|---|---|
| Saline | 0 |
| PPMK107 | 44 |
| Carbo | 25 |
| PPMK107 Carbo | 89 |

These results in Table 34 indicate that subcutaneous HT1080 tumors are responsive to IV treatment with PPMK107 and that addition of carboplatin two days before PPMK107 treatment resulted in a higher percentage of tumor regression (CR+PR) than either PPMK107 alone or carboplatin alone.

EXAMPLE 37

Use of a Corticosteroid (Dexamethasone) to Reduce the Lethality of an Intravenous Dose of PPMK107

Female athymic mice (six to seven weeks old) were injected intraperitoneally on days 0, 1, 2, 3 and 4 with either dexamethasone (one group at a dose of 25 mg/kg and another group at 10 mg/kg) or saline. All animlas were given an intravenous dose of PPMK107 ($3\times10^9$ PFU/mouse) on day 2 (one hour following the IP dose of dexamethasone or saline). Mice were observed and the lethality tabulated in Table 33 below.

TABLE 35

Use of Dexamethasone to Reduce the Lethality of an Intravenous Dose of PPMK107

| Group | IP Treatment on Days 0, 1, 2, 3, and 4 | IV Treatment on Day 2 | Lethality (%) |
|---|---|---|---|
| 1 | Dexamethasone (25 mg/kg) | PPMK107, 3.0E+09 | 7 |
| 2 | Dexamethasone (10 mg/kg) | PPMK107, 3.0E+09 | 0 |
| 3 | Saline | PPMK107, 3.0E+09 | 67 |

The PPMK107 dose of $3\times10^9$ was lethal to 67% of the mice given saline control IP dosing. Dexamethasone markedly reduced lethaltiy due to PPMK107 with only 7% mortality observed in the animals given 25 mg/kg and 0% mortality observed in the animals given 10 mg/kg. These data indicated that a corticosteroid like dexamethasone can be used to reduce the toxicity of an intravenous dose of PPMK107.

The strain MK107 (no accession number) is deposited with the USDA Repository, 1800 Dayton Avenue, Ames, Iowa 50010.

The foregoing is intended as illustrative of the present invention but not limiting. Numerous variations and modifications may be affected without departing from the true spirit and scope of the invention.

What is claimed is:

1. A method of infecting a tumor with a volume of $\geq 300$ mm$^3$ in a mammal with a virus comprising systemically administering to said mammal an interferon-sensitive, replication-competent clonal ribonucleic acid (RNA) virus derived from a single infectious virus particle and for which eight individual molecular clones from the population of virions have an identical sequence over 300 contiguous nucleotides, wherein said virus is administered as a first dose and one or more subsequent doses, and wherein the first dose is a desensitizing dose, to thereby infect said tumor, wherein the virus is Newcastle Disease Virus (NDV).

2. A method of treating a tumor with a volume of ≧300 mm³ in mammal comprising systemically administering to said mammal a therapeutically effective amount of an interferon-sensitive, replication-competent clonal ribonucleic acid (RNA) virus derived from a single infectious virus particle and for which eight individual molecular clones for the population of virions have an identical sequences over 300 contiguous nucleotides, wherein said virus is administered as a first dose and one or more subsequent doses, and wherein the first dose is a desensitizing dose, to thereby treat said tumor, wherein the virus is Newcastle Disease Virus (NDV).

3. A method as in claim 1 wherein said NDV virus replicates at least 100-fold less in the presence of interferon compared to in the absence of interferon.

4. A method of claim 1 wherein said NDV virus replicates at least 1000-fold less in the presence of interferon compared to in the absence of interferon.

5. A method as in claim 1 wherein said mammal is a human.

6. A method as in claim 1 wherein said clonal NDV virus is plaque purified.

7. A method as in claim 1 wherein said clonal NDV virus is of recombinant clonal origin.

8. A method as in claim 1 wherein said Newcastle Disease Virus is purified to a level of at least $2 \times 10^9$ plaque-forming units (PFU) per mg of protein.

9. A method as in claim 1 wherein said Newcastle Disease Virus is purified to a level of at least $1 \times 10^{10}$ PFU per mg of protein.

10. A method as in claim 1 wherein said Newcastle Disease Virus is purified to a level of at least $6 \times 10^{10}$ PFU per mg of protein.

11. A method as in claim 1 wherein said Newcastle Disease Virus is purified to a level in which the particle per PFU ratio is no greater than 5.

12. A method as in claim 1 wherein said Newcastle Disease Virus is purified to a level in which the particle per PFU ratio is no greater than 3.

13. A method as in claim 1 wherein said Newcastle Disease Virus is purified to a level in which the particle per PFU ratio is no greater than 1.2.

14. A method as in claim 1 wherein said tumor is selected from the group consisting of a lung tumor, a colon tumor, a prostate tumor, a breast tumor and a brain tumor.

15. A method as in claim 14 wherein said brain tumor is a glioblastoma.

16. A method as in claim 1 further comprising administering interferon (IFN), before, during or after administration of said virus.

17. A method as in claim 16 wherein said IFN is selected from the group consisting of α-IFN, β-IFN, ω-IFN, γ-IFN, and syntheitc consensus forms of IFN.

18. A method as in claim 1 further comprising administering a compound selected from the group of compounds comprising a purine nucleoside analog, tyrosine kinase inhibitor, cimetidine, and mitochondrial inhibitors.

19. A method as in claim 1 further comprising administrating a chemotherapeutic agent before, during or after administration of said virus.

20. A method as in claim 1 further comprising administering a cytokine before, during or after administration of said virus.

21. A method as in claim 1 further comprising administering an immunosuppressant before, during or after administration of said virus.

22. A method as in claim 1 further comprising administering a viral replication controlling amount of a compound selected from the group consisting of IFN and ribavirin.

23. A method as in claim 1 wherein said administration is intravenous.

24. A method as in claim 1 wherein said virus is selected from the group consisting of the Newcastle disease virus strain MK107 and Newcastle disease virus strain NJRoakin.

25. A method as in claim 1 wherein said first dose is administered intravenously and a subsequent dose administered intravenously.

26. A method as in claim 1 wherein said one or more subsequent doses are higher than the first dose.

27. A method as in claim 2 wherein said one or more subsequent doses are higher than the first dose.

28. A method of infecting a neoplasm in a mammal with a virus comprising systemically administering an interferon-sensitive, replication-competent clonal ribonucleic acid (RNA) virus derived from a single infectious virus particle and for which eight individual molecular clones from the population of virions have an identical sequence over 300 contiguous nucleotides, wherein said virus is administrated as a first dose and one or more subsequent doses, wherein the first dose is a desensitizing dose, and wherein said one or more subsequent doses are higher than the first dose, to thereby infect said neoplasm, wherein the virus is Newcastle Disease Virus (NDV).

29. A method of treating a tumor in a mammal comprising systemically administering to said mammal a therapeutically effective amount of an interferon-sensitive, replication-competent clonal ribonucleic acid (RNA) virus derived from a single infectious virus particle and for which eight individual molecular clones from the population of virions have an identical sequence over 300 contiguous nucleotides, wherein said virus is administered as a first dose and one or more subsequent doses, wherein the first dose is a desensitizing dose and wherein said one or more subsequent doses are higher than the first dose, to thereby treat said tumor, wherein the virus is Newcastle Disease Virus (NDV).

30. A method as in claim 28 wherein said NDV virus replicates at least 100-fold less in the presence of interferon compared to in the absence of interferon.

31. A method as in claim 28 wherein said NDV virus replicates at least 1000-fold less in the presence of interferon compared to in the absence of interferon.

32. A method as in claim 28 wherein said neoplasm is a cancer.

33. A method as in claim 28 wherein said mammal is a human.

34. A method as in claim 28 wherein said clonal NDV virus is plaque purified.

35. A method as in claim 28 wherein said clonal NDV virus of recombinant clonal origin.

36. A method as in claim 28 wherein said Newcastle Disease virus is purified to a level of at least $2 \times 10^9$ plaque forming units (PFU) per mg of protein.

37. A method as in claim 28 wherein said Newcastle Disease Virus is purified to a level of at least $1 \times 10^{10}$ PFU per mg of protein.

38. A method as in claim 28 wherein said Newcastle Disease Virus is purified to a level of at least $6 \times 10^{10}$ PFU per mg of protein.

39. A method as in claim 28 wherein said Newcastle Disease Virus is purified to a level in which the particle per PFU ratio is no greater than 5.

40. A method as in claim 28 wherein said Newcastle Disease Virus is purified to a level in which the particle per PFU ratio is no greater than 3.

41. A method as in claim 28 wherein said Newcastle Disease Virus is purified to a level in which the particle per PFU ratio is no greater than 1.2.

42. A method as in claim 28 wherein said neoplasm is a cancer selected from the group consisting of lung, colon, prostate, breast and brain cancer.

43. A method as in claim 28 wherein said neoplasm is a solid tumor.

44. A method as in claim 42 wherein said brain cancer is a glioblastoma.

45. A method as in claim 28 wherein said virus contains a gene encoding interferon to permit the viral expression of interferon.

46. A method as in claim 28 wherein said virus contains a gene encoding a pro-drug activating enzyme.

47. A method as in claim 28 further comprising administering interferon (IFN), before, during or after administration of said virus.

48. A method as in claim 47 wherein said IFN is selected from the group consisting of α-IFN, β-IFN, ω-IFN, γ-IFN, and synthetic consensus forms of IFN.

49. A method as in claim 28 further comprising administering a compound selected from the group of compounds comprising a purine nucleoside analog, tyrosine kinase inhibitor, cimetidine, and mitochondrial inhibitors.

50. A method as in claim 28 further comprising administering a chemotherapeutic agent before, during or after administration of said virus.

51. A method as in claim 28 further comprising administering a cytokine before, during or after administration of said virus.

52. A method as in claim 28 further comprising administering an immunosuppressant before, during or after administration of said virus.

53. A method as in claim 28 further comprising administering a viral replication controlling amount of a compound selected from the group consisting of IFN and ribavirin.

54. A method as in claim 28 wherein said administration is intravenous.

55. A method as in claim 28 wherein said first dose is administered intravenously and a subsequent dose administered intravenously.

56. A method as in claim 2 further comprising administering a chemotherapeutic agent before, during or after administration of said virus.

57. A method as in claim 29 further comprising administering a chemotherapeutic agent before, during or after administration of said virus.

58. A method of infecting a neoplasm in a mammal with a virus comprising systemically administering an interferon-sensitive, replication-competent clonal ribonucleic acid (RNA) virus derived from a single infectious virus particle and for which eight individual molecular clones from the population of virions have an identical sequence over 300 contiguous nucleotides, wherein said virus is administered as a first dose and one or more subsequent doses, wherein the first dose is a desensitizing dose, and wherein said one or more subsequent doses are higher than the first dose, to thereby infect said neoplasm, wherein said virus is selected from the group consisting of the Newcastle disease virus strain MK107 and Newcastle disease virus strain NJRoakin, Sindbis virus, and Vesicular stomatitis virus.

\* \* \* \* \*

UNITED STATES PATENT AND TRADEMARK OFFICE
CERTIFICATE OF CORRECTION

PATENT NO. : 7,470,426 B1  
APPLICATION NO. : 09/958809  
DATED : December 30, 2008  
INVENTOR(S) : Roberts et al.

Page 1 of 1

It is certified that error appears in the above-identified patent and that said Letters Patent is hereby corrected as shown below:

Column 57, Claim 2, line 7, please delete "in mammal" and insert --in a mammal--.

Column 57, Claim 2, line 12, please delete "sequences" and insert --sequence--.

Column 57, Claim 4, line 20, please delete "of" and insert --as in--.

Column 57, Claim 17, line 57, please delete "syntheitc" and insert --synthetic--.

Signed and Sealed this

Seventeenth Day of March, 2009

JOHN DOLL  
*Acting Director of the United States Patent and Trademark Office*